United States Patent
Lewis et al.

(10) Patent No.: US 6,693,076 B1
(45) Date of Patent: *Feb. 17, 2004

(54) TREATING DISORDERS BY APPLICATION OF INSULIN-LIKE GROWTH FACTORS AND ANALOGS

(75) Inventors: Michael E. Lewis, West Chester, PA (US); James C. Kauer, Kennett Square, PA (US); Kevin R. Smith, Gap, PA (US); Kathleen V. Callison, Merchantville, NJ (US); Frank Baldino, Chadds Ford, PA (US)

(73) Assignee: Cephalon, Inc., West Chester, PA (US)

( * ) Notice: Subject to any disclaimer, the term of this patent is extended or adjusted under 35 U.S.C. 154(b) by 819 days.

This patent is subject to a terminal disclaimer.

(21) Appl. No.: 09/318,001

(22) Filed: May 25, 1999

Related U.S. Application Data

(63) Continuation of application No. 09/064,159, filed on Apr. 22, 1998, which is a continuation of application No. 08/823,245, filed on Mar. 24, 1997, now Pat. No. 5,776,897, which is a continuation of application No. 07/958,903, filed on Oct. 7, 1992, now Pat. No. 5,652,214, which is a continuation-in-part of application No. 07/869,913, filed on Apr. 15, 1992, now abandoned, which is a continuation-in-part of application No. 07/534,139, filed on Jun. 5, 1990, now abandoned, which is a continuation-in-part of application No. 07/361,595, filed on Jun. 5, 1989, now Pat. No. 5,093,317.

(51) Int. Cl.$^7$ ............................... A61K 38/30
(52) U.S. Cl. ........................ 514/12; 514/21
(58) Field of Search .................. 514/2, 3, 9, 11, 514/12, 21; 530/303, 317, 324

(56) References Cited

U.S. PATENT DOCUMENTS

| | | | |
|---|---|---|---|
| 4,356,314 A | * 10/1982 | Cragoe, Jr. et al. | 560/53 |
| 4,511,390 A | 4/1985 | Kauer | 71/88 |
| 4,699,875 A | 10/1987 | Appel | 435/4 |
| 4,783,524 A | 11/1988 | Larsen et al. | 530/350 |
| 4,801,575 A | * 1/1989 | Pardridge | 514/4 |
| 4,837,226 A | * 6/1989 | Coughenour et al. | 514/443 |
| 5,093,317 A | * 3/1992 | Lewis et al. | 514/12 |
| 5,652,214 A | * 7/1997 | Lewis et al. | 514/12 |
| 5,714,460 A | * 2/1998 | Gluckman et al. | 514/3 |
| 5,776,897 A | * 7/1998 | Lewis et al. | 514/12 |
| 5,861,373 A | * 1/1999 | Gluckman et al. | 514/3 |

FOREIGN PATENT DOCUMENTS

| | | |
|---|---|---|
| EP | 0 227 619 A2 | 7/1987 |
| EP | 0 289 314 A2 | 11/1988 |
| EP | 0 308 386 A1 | 3/1989 |
| JP | 59-065058 | 4/1984 |
| JP | 63-196524 | 8/1988 |
| WO | WO 88/08848 | 11/1988 |
| WO | WO 88/09171 | 12/1988 |
| WO | WO 89/01343 | 2/1989 |
| WO | WO 89/05822 | 6/1989 |
| WO | WO 90/14838 | 12/1990 |

OTHER PUBLICATIONS

Philipps et al. The Effects of Biosynthetic Insulin–Like Growth Factor–1 . . . Pediatric Research, vol. 23, No. 3, pp. 298–305, 1988.*

Sara et al, The role of the insulin–like growth factors . . . Prog. Brain Research, vol. 73, pp. 87–99, 1988.*

Aizenman et al., "Brain neurons develop in a serum and glial free environment: effects of transferrin, insulin, insulin–like growth factor–I and thyroid hormone on neuronal survival, growth and differentiation", *Brain Res.*, 1987, 406, 32–42.

(List continued on next page.)

*Primary Examiner*—Jeffrey E. Russel
(74) *Attorney, Agent, or Firm*—Woodcock Washburn LLP

(57) ABSTRACT

A method of enhancing the survival of neuronal cells in a mammal, the cells being at risk of dying, the method comprising administering to the mammal an effective amount of one of the following substances: IGF-I; a functional derivative of IGF-I; IGF-II; a functional derivative of IGF-II; IGF-III; or a functional derivative of IGF-III.

8 Claims, 23 Drawing Sheets

OTHER PUBLICATIONS

Audus et al., "Bovine Brain Microvessel Endothelial Cell Monolayers as a Model System for the Blood–Brain Barrier", *Ann. N.Y. Acad. Sci.,* 1987, 507, 9–18.

Baskin et al., "Insulin and insulin–like growth factors in the CNS", *TINS,* 1988 11(3), 107–111.

Baxter et al., "The Insulin–Like Growth Factors and Their Binding Proteins", *Comp. Biochem. Physiol.,* 1988, 91B(2), 229–235.

Blundell et al., "Tertiary structures, receptor binding, and antigenicity of insulinlike growth factors", *Feb. Proc.,* 1983, 42(9), 2592–2597.

Bodor et al., "Site–Specific, Sustained Release of Drugs to the Brain", *Science,* 1981, 214, 1370–1372.

Bohannon et al., "Identification of Binding Sites for an Insulin–like Growth Factor (IGF–1) in the Median Eminence of the Rat Brain by Quantitative Autoradiography", *Endocrinology,* 1986, 119(2), 943–945.

Bothwell, "Insulin and Somatemedin MSA Promote Nerve Growth Factor–Independent Neurite Formation by Cultured Chick Dorsal Root Ganglionic Sensory Neurons", *J. Neurosci.,* 1982, 8, 225–231.

Bottenstein et al., "Growth of a rat neuroblastoma cell line in serum–free supplemented medium", *Proc. Natl. Acad. Sci. USA,* 1979, 76(1), 514–517.

Coy et al., "Synthesis and Opioid Activities of Stereoisomers and Other D–Amino Acid Analogs of Methionine–Enkephalin", *Biochem. Biophys. Res. Commun.,* 1976, 73(3), 632–638.

Creveling et al., "Labile Lipophilic Derivatives of Norepinephrine Capable of Crossing the Blood–Brain Barrier", *Experientia,* 1969, 25, 26–27.

Daughaday et al., "Insulin–Like Growth Factors I and II. Peptide, Messenger Ribonuycleic Acid and Gene Structures, Serum, and Tissue Concentrations", *Endocrine Rev.,* 1989, 10(1), 68–91.

D'Ercole, "Somatomedins/insulin–like growth factors and fetal growth", *J. Devel. Physiol.,* 1987, 9, 481–495.

Fellows et al., "IGF–1 Supports Survival and Differentiation of Fetal Rat Brain Neruons in Serum–Free Hormone–Free Defined Medium", *Soc. Neurosci. Abstr.,* 1987, 13, 1615.

Fonnum, "A rapid radiochemical method for the determination of choline acetyltransferase", *J. Neurochem.,* 1975, 24, 407–409.

Francis et al., "Long R3 IGF–1—A Potent Insulin–like Growth Factor–I Analog that Supports Cell Growth", *Art to Science in Tissue Culture, HyClone Laboratories,* 1992, 11(1), 3–7.

Francis et al., "Insulin–like growth factors 1 and 2 in bovine colostrum", *Biochem. J.,* 1988, 251, 95–103.

Goodman et al., "On the Concept of Linear Modified Retro–Peptide Structures", *Acc. Chem. Res.,* 1979, 12(1), 1–7.

Hansson et al., "Evidence indicating trophic importance of IGF–1 in regenerating peripheral nerves", *Acta Physiol. Scand.,* 1986, 126, 609–614.

Hansson et al., "Transient increase in insulin–like growth factor I immunoreactivity in rat peripheral nerves exposed to vibrations", *Acta Physiol. Scand.,* 1988, 132, 35–41.

Hassner et al., "Direct Room Temperature Esterification of Carboxylic Acids", *Tetra. Lett.,* 1978, 46, 4475–4478.

Hartikka et al., "Development of Septal Cholinergic Neurons in Culture: Plating Density and Glial Cells Modulate Effects of NGF on Survival, Fiber Growth, and Expression of Transmitter–Specific Enzymes", *J. Neurosci.,* 1988, 8(8), 2967–2985.

Hayashi et al., "An interaction between thyroid hormone and nerve growth factor in the regulation of choline acetyltransferase activity in neuronal cultures, derived from the septal–diagonal band region of the embryonic rat brain", *Dev. Brain Res.,* 1987, 36, 109–120.

Hayward et al., "The Effect of Reversal of the Direction of Peptide Bonds on the Interaction Between Peptide Hormones and Receptors", *Peptides,* Proc. 13th Eur. Peptide Symp., Wolman, Y. (Ed.), 1974, 287–297.

Herkenham et al., "Light microscopic localization of brain opiate receptors: A general autoradiographic method which preserves tissue quality", *J. Neurosci.,* 1982, 2(8), 1129–1149.

Hintz et al., "A Radioimmunoassay for Insulin–like Growth Factor II Specific for the C–Peptide Region", *J. Clin. Endocr. Metab.,* 1982, 54, 442–446.

Hintz et al., "A Sensitive Radioimmunoassay for Somatomedin–C/Insulin–Like Growth–Factor I Based on Synthetic Insulin–Like Growth Factor 57–70", *Horm. Metab. Res.,* 1988, 20, 344–347.

Hudson, "Methodological Implications of Simultaneous Solid–Phase Peptide Synthesis. 1. Comparison of Different Coupling Procedures", *J. Org. Chem.,* 1988, 53, 617–624.

Kanje et al., "Ornithine Decarboxylase Activity in Dorsal Root Ganglia of Regenerating Frog Sciatic Nerve", *Brain Res.,* 1986, 381, 24–28.

Kastin et al., "Analgesia After Peripheral Administration of Enkephalin and Endorphin Analogues", *Pharma. Biochem. Behav.,* 1979, 11, 713–716.

Knusel et al., "Selective and Nonselective Stimulation of Central Cholinergic and Dopaminergic Development in vitro by Nerve Growth Factor. Basic Fibroblast Growth Factor, Epidermal Growth Factor, Insulin and the Insulin–like Growth Factors I and II", *J. Neurosci.,* 1990, 10(2), 558–570.

Kumagai et al., "Absorptive–mediated Endocytosis of Cationized Albumin and a β–Endorphin–cationized Albumin Chimeric Peptide by Isolated Brain Capillaries", *J. Biol. Chem.,* 1987, 262(31), 15214–15219.

Lewis et al., "Nerve growth factor increases activity of ornithine decarboxylase in rat brain", *Proc. Natl. Acad. Sci. USA,* 1978, 75(2), 1021–1023.

Littlewood et al., "Neuropeptides and Their Peptidases: Functional Considerations", *Neurochem. Int.,* 1988, 12(3), 383–389.

McManaman et al., "Low–Molecular–Wieght Peptide Stimulates Cholinergic Development in Ventral Spinal Cord Cultures", *Devel. Biol.,* 1985, 112, 248–252.

McManaman et al., "Development Discord among Markers for Cholinergic Differentiation: In Vitro Time Courses for Early Expression and Responses ot Skeletal Muscle Extract", *Devel. Biol.,* 1988, 125, 311–320.

McManaman et al., "Rescue of Motoneurons from Cell Death by a Purified Skeletal Muscle Polypeptide: Effects of the ChAT Development Factor, CDF", *Neuron.,* 1990, 4, 891–898.

McMorris et al., "Insulin–like growth factor I/somatomedin C: a potent inducer of oligodendrocyte development", *Proc. Natl. Acad. Sci. USA,* 1986, 83, 822–826.

McMorris et al., "Regulation of Oligodendrocyte Development by Insulin–Like Growth Factors and Cyclic Nucleotrides", *Myelination Dysmyelination,* 1990, 605, 101–109.

MacDonnell et al., "Nerve growth factor increases activity of ornithine decarboxylase in superior cervical ganglia of young rats", *Proc. Natl. Acad. Sci. USA,* 1977, 74(10), 4681–4684.

Maly et al., "The Binding Sites of Insulin–like Growth factor I (IGF I) to Type I IGF Receptor and to a Monoclonal Antibody", *J. Biol. Chem.,* 1988, 263(15), 7068–7072.

Mattsson et al., "Mitogenic Response of Human SH–SY5Y Neuroblastoma Cells to Insulin–like Growth Factor I and II Is Dependent on the Stage of Differentiation", *J. Cell Biol.,* 1986, 102, 1949–1954.

Mihara et al., "Syntheses of AM–toxin I analogs containing L–lactic acid of L–2–hydroxy–4–methylpentanoic acid residue", *Int. J. Peptide Protein Res.,* 1986, 28, 141–145.

Mozell et al., "Insulin–Like Growth Factor–I Stimulates Regeneration of Oligodendrocytes in Vitro", *Advances Neuroimmunology,* 1988, 540, 430–432.

Nilsson et al., "Insulin–like growth factor I stimulates the release of acetylcholine from rat cortical slices", *Neurosci. Lett.,* 1988, 88, 221–226.

Onifer et al., "Effects of Insulin–Like Growth Factor II (IGF–II) on Hippocampal and Septal Neurons Maintained in Tissue Culture", *Soc. Neurosci. Abstr.,* 1987, 13, 1615.

Oppenheim, "Cell Death During Development of the Nervous System", *Annu. Rev. Neurosci.,* 1991, 14, 453–501.

Oppenheim et al., "Control of Embryonic Motoneuron Survival in Vivo by Ciliary Neurotrophic Factor", *Science,* 1991, 251, 1616–1617.

Pardridge et al., "Chimeric Peptides as a Vehicle for Peptide Pharmaceutical Delivery Through the Blood–Brain Barrier", *Biochem. Biophys. Res. Commun.,* 1987, 146(1), 307–313.

Pardridge, "Receptor–Mediated Peptide Transport through the Blood–Brain Barrier", *Endocrine Rev.,* 1986, 7(3), 314–330.

Philipps et al., "The Effects of Biosynthetic Insulin–Like Growth Factor–1 Supplementation on Somatic Growth, Maturation, and Erythropoiesis on the Neonatal Rat", *Pediatr. Res.,* 1988, 23, 298–305.

Rapoport et al., "Entry of Opioid Peptides into the Central Nervous System", *Science,* 1980, 207, 84–86.

Recio–Pinto et al., "Insulin and insulin–like growth factor II permit nerve growth factor binding and the neurite formation response in cultured human neuroblastoma cells", *Proc. Natl. Acad. Sci. USA,* 1984, 81, 2562–2566.

Recio–Pinto et al., "Effects of Insulin, Insulin–Like Growth Factor–II, and Nerve Growth factor on Neurite Formation and Survival in Cultured Sympathetic and Sensory Neurons", *J. Neurosci.,* 1986, 6(5), 1211–1219.

Recio–Pinto et al., "Insulin and Insulinlike Growth Factor Receptors Regulating Neurite Formation in Cultured Human Neuroblastoma Cells", *J. Neurosci. Res.,* 1988, 19, 312–320.

*Remington's Pharmaceutical Sciences,* Mack Publishing Co., Easton, PA, 1980.

Riekkinen et al., "Penetration of DGAVP (Org 5667) Across the Blood–Brain Barrier in Human Subjects", *Peptides,* 1987, 8, 261–265.

Rinehart et al., "Induction of ornithine decarxoylase activity by insulin and growth factors is mediated by amino acids", *Proc. Natl. Acad. Sci. USA,* 1985, 82, 4365–4368.

Russell et al., "Proposed Model of Major Sequential Biochemical Events of a Trophic Response", *Life Sci.,* 1976, 19, 1297–1306.

Sara et al., "Somatomedins in Down's Syndrome", *Biol. Psychiatry,* 1983, 18(7), 803–811.

Sara et al., "Characterization of somatomedins from human fetal brain: Identification of a variant form of insulin–like growth factor I", *Proc. Natl. Acad. Sci. USA,* 1986, 83, 4904–4907.

Sara et al., "Evidence for the Presence of Specific Receptors for Insulin–Like Growth Factors 1 (IGF–1) and 2 (IGF–2) and Insulin Throughout the Adult Human Brain", *Neurosci. Lett.,* 1982, 34, 39–44.

Sara et al., "The influence of early nutrition on growth and the circulating levels of immunoreactive somatomedin A", *J. Dev. Physiol.,* 1979, 1, 343–350.

Sara et al., "The role of the insulin–like growth factors in the regulation of brain development", *Prog. Brain Res.,* 1988, 73, 87–99.

Sara et al., "Somatomedins in Aging and Dementia Disorders of the Alzheimer Type", *Neurobiol. Aging,* 1982, 3, 117–120.

Schwartz et al., "Proteins Containing Reductively Aminated Disaccharides", *Arch. Biochem. Biophys.,* 1977, 181, 542–549.

Schwartz et al., "Ornithine Decarboxylase Activity in Retinal Explants of Goldfish Undergoing Optic Nerve Regeneration", *Dev. Brain Res.,* 1981, 1, 403–413.

Shen et al., "Conjugation of poly–L–lysine to albumin and horseradish peroxidase: A novel method of enhancing the cellular uptake of proteins", *Proc. Natl. Acad. Sci. USA,* 1978, 75(4), 1872–1876.

Sjöberg et al., "Insulin–like growth factor (IGF–1) as a stimulator of regeneration in the freeze–injured rat sciatic nerve", *Brain Res.,* 1989, 485, 102–108.

Smith, K.R. et al., "Permeability and Mechanism of Albumin, Cationized Albumin, and Glycosylated Albumin Transcellular Transport Across Monolayers of Cultured Bovine Brain Capillary Endothelial Cells", *Pharm. Res.,* 1989, 6(6), 466–473.

Taylor et al., "Small Peptides and Nerve Growth: Therapeutic Implications", *Drug Develop. Res.,* 1987, 11, 75–86.

Williams et al., "Continuous infusion of nerve growth factor prevents basal forebrain neuronal death after fimbria fornix transection", *Proc. Natl. Acad. Sci. USA,* 1986, 83, 9231–9325.

Williams et al., "Micropinocytic ingestion of glycosylated albumin by isolated microvessels: Possible role in pathogenesis of diabetic microangiopathy", *Proc. Natl. Acad. Sci. USA,* 1981, 78(4), 2393–2397.

IUPAC–IUB Joint Commission on Biochemical Nomenclature (JCBN), "Nomenclature and Symbolism for Amino Acids and Peptides", Recommendations 1983, *J. Biol. Chem.,* 1985, 260(1), 14–42.

Smith, "Molecular Cell Biology" in *Textbook of Biochemistry, 3rd Ed;* eds. Devlon et al; Wiley & Sons, Inc. Publishers (New York), pp. 927–938, 1993.

Raine, "Neurocellular Anatomy" in *Basic Neurochemistry, 4th Ed.* Raven Press (New York), Ch. 1, pp. 3–33, 1989.

Silver, "Transplantation Strategies Using Ebryonic Astoglial Cells to Promote CNS Axon Regeneration in Neonatal and Adult Mammals", *Clin. Res.,* vol. 36, pp. 196–199, 1988.

Arenella, L.S. et al., "Mature Oligodendrocytes. Division Following Experimental Demyelination in Adult Animals", *Arch. Neurol.,* vol. 41, pp. 1162–1165, 1984.

*Principles of Neural Science, 3rd Ed;* eds. E.R. Kandel et al; Prentic Hall International Inc., 1991.

McGreer et al., "Amino Acid Neurotransmitters" in *Basic Neurochemistry: Molecular, Cellular and Medical Aspects;* Raven Press (New York), Ch. 15, pp. 311–331, 1989.

Cooper et al., "Amino–Acid Transmitters" *The Biochemical Basis of Neuropharmacology, 5th Ed;* Oxford Press (New York), pp. 124–202, 1986.

Cuello, A.C. et al., "The Anatomy of the CNS cholinergic neurons", *Trends in Neroscience,* pp. 74–78, Mar. 1984.

Katzman et al., "Neurochemistry of Alzheimer's Disease" in *Basic Neurochemistry: Molecular, Cellular and Medical Aspects, 4th Ed.;* Raven Press, (New York), Ch. 43, pp. 827–838, 1989.

Saper, C.B., "Cholinergic System" in *The Human Nervous System;* Paxinos, G., (ed.), Academic Press (San Diego), Ch. 33, pp. 1095–1113, 1990.

Sourkes, T.L., "Disorders of the Basal Ganglia" in *Neurochemistry: Molecular, Cellular and Medical Aspects, 4th Ed.;* Siedel G.J. (Eds.), Raven Press (New York), Ch. 42, pp. 811–825, 1989.

Nyberg, P. et al., "Age–Dependent Vulnerability of Brain Choline Acetyltransferase Activity to Transient Cerebral Ischemia in Rats", *Stroke,* vol. 20, No. 4, pp. 495–500, Apr. 1989.

Kataoka, K. et al., "Cholinergic Deafferentation After Focal Cerebral Infarct in Rats",*Stroke,* vol. 22, No. 10, pp. 1291–1296, Oct. 1991.

Weiner, N. et al., (eds.), *Basic Neurochemistry: Molecular, Cellular and Medical Aspects,* Raven Press (New York), Ch. 11, pp. 233–251, 1989.

McMorris, F.A. et al., "Insulin–Like Growth Factor I Promotes Cell Proliferation and Oligodendroglial Commitment in Rat Glial Progenitor Cells Developing In Vitro", *J. Neurosci. Res.,* vol. 21, pp. 199–209, 1988.

Behar, T. et al., "Growth and Differentiation Properties of O–2A Progenitors Purified From Rat Cerebral Hemispheres", *J. Neurosci. Res.,* vol. 21, pp. 168–180, 1988.

van der Pal, R.H.M. et al., "Effects of Insulin and Insulin–Like Growth Factor (IGF–1) on Oligodendrocyte–Enriched Glial Cultures", *J. Neurosci. Res.,* vol. 19, pp. 483–490, 1988.

Carson, M. et al., "Myelin and 2',3'–Cyclic Nucleotide 3'–Phosphohydrolase Levels Are Elevated in Transgenic Mice Producing Increased Levels of Insulin–Like Growth Factor–1 (IGF–1)", *Trans. Am. Soc. Neurochem.,* vol. 19, p. 82, Mar. 7, 1988.

Carson, M., et al., "Myelin Content Increased in Transgenic Mice Producing Elevated Levels of Insulin–like Growth Factor–1 (IGF–1)", *Neurosci. Absts.,* vol. 14, p. 119, 1988.

Carson, M., et al., "Hypomyelination Caused by Growth Hormone Deficiency is Reversed by Insulin–Like Growth Factor 1 in Transgenic Mice", *Trans. Am. Soc. Neurochem.,* vol. 20, No. 1, p. 286, Mar. 1989.

Adams and Victor (eds.), *Principles of Neurology, 4th Ed.,* McGraw–Hill, New York, Ch. 37, pp. 755–774, 1989.

Ballotti, R. et al., "Insulin–like growth factor I in cultured rat astrocytes: expression of the gene, and receptor tyrosine kinase", *EMBO J.,* vol. 6, No. 12, pp. 3633–3639, 1987.

Franklin, R.J.M. et al., "Transplanted type–1 astrocytes facilitate repair of demyelinating lesions by host oligodendrocytes in adult rat spinal cord", *J. Neurocytology,* vol. 20, pp. 420–430, 1991.

Rosenberg, P., "Hundred–fold increase in neuronal vulnerability to glutamate toxicity in astrocyte–poor cultures of rat cerebral cortex", *Neurosci. Lett.,* vol. 103, pp. 162–168, 1989.

Paty et al., "Management of Multiple Sclerosis and Interpretation of Clinical Trials" in *Multiple Sclerosis,* Paty D.W., Ebers, G.C. (eds.), FA Davis, Philadelphia, Ch. 12, pp. 427–545, 1997.

Rechler, M. et al., "The Nature and Regulation of the Receptors for Insulin–Like Growth Factors", *Ann. Rev. Physiol.,* vol. 47, pp. 425–442, 1985.

Hepler, J.E. et al., "Molecular Biology of the Insulin–like Growth Factors", *Mol. Neurobiol.,* vol. 4, pp. 93–127, 1990.

Werner et al., "The Insulin–Like Growth Factor Receptor: Molecular Biology, Heterogeneity, and Regulation" in *Insulin–Like Growth Factors: Molecular and Cellular Aspects,* ed. D. Leroith, Boca Raton: CRC Press, Ch. 2, pp. 17–47, May 1991.

Ludwin, S., "Evolving Concepts and Issues in Remyelination", *Dev. Neurosci.,* vol. 11, pp. 140–148, 1989.

Ludwin, S. et al., "Can Oligodendrocytes Attached to Myelin Proliferate?", *J. Neurosci.,* vol. 8, No. 4, pp. 1239–1244, 1988.

Gluckman et al., "A role of IGF–1 in the resuce of CNS Neurons following hypoxic–ischemic injury", *Biochem., Biophys. Res. Commun.,* vol. 182, No. 2, pp. 593–599, Jan. 31, 1992.

Barres et al., "Cell Death and Control of Cell Survival in the Oligodendrocyte Lineage", *Cell,* vol. 70, pp. 31–46, Jul. 10, 1992.

McMorris et al., "Regulation of Oligodendrocyte Development and Central Nervous System Myelination by Insulin–like Growth Factors", *Ann. N.Y. Acad. Sci.,* vol. 692, pp. 321–334, 1993.

McKhann, G.M., "Multiple Sclerosis", *Ann. Rev. Neurosci.,* vol. 5, pp. 219–239, 1982.

* cited by examiner

A: 2nM NGF

B: 25 nM IGF I

C: IGF I + NGF, 5 DAYS

D: IGF I, 5 DAYS + NGF ADDED ON DAY 3

TREATING DISORDERS BY APPLICATION OF INSULIN-LIKE GROWTH FACTORS AND ANALOGS

This application is a continuation of U.S. application Ser. No. 09/064,159, filed, Apr. 22, 1998, which is a continuation of Ser. No. 08/823,245, filed Mar. 24, 1997, (now U.S. Pat. No. 5,776,897) which is a continuation of Ser. No. 07/958, 903, filed Oct. 7, 1992 (now U.S. Pat. No. 5,652,214), which is a continuation-in-part of Ser. No. 07/869,913, filed Apr. 15, 1992 (now abandoned), which is a continuation-in-part of Ser. No. 07/534,139, filed Jun. 5, 1990 (now abandoned), which is a continuation-in-part of Ser. No. 07/361,595, filed Jun. 5, 1989 (now U.S. Pat. No. 5,093,317), the entire contents of each of said applications are incorporated herein by reference.

BACKGROUND OF THE INVENTION

The present invention relates to therapeutic polypeptides useful, e.g., for the treatment of neurological and other disorders.

Insulin-like growth factors (IGFs) have been identified in various animal species as polypeptides that act to stimulate growth of cells in a variety of tissues (see Baxter et al., Comp. Biochem. Physiol. 91B:229–235 (1988); and Daughaday et al., Endocrine Rev. 10:68–91 (1989) for reviews), particularly during development (see D'Ercole, J. Devel. Physiol. 9:481–495 (1987) for review). The IGFs each of which has a molecular weight or about 7,500 daltons, are chemically related to human proinsulin: i.e. they possess A and B domains that (1) are highly homologous to the corresponding domains of proinsulin, and (2) are connected by a smaller and unrelated C domain. A carboxyl-terminal extension, the D domain, is also present in IGFs but is not found in proinsulin.

Certain polypeptide fragments of the IGFs have proven to be useful as antigens to raise antibodies specific for each of the IGFs (see, e.g., Japanese Patent Application No. 59065058; Hintz and Liu, J. Clin. Endocr. Metab. 54:442–446 (1982); Hintz et al., Horm. Metab. Res. 20:344–347 (1988)). Using labelled IGF-specific antibodies as a probe, IGF-I and IGF-II (sometimes respectively termed "somatomedin C" and "somatomedin A") have been found in a variety of tissues, including the mammalian central nervous system (CNS); the presence in the CNS of mRNAs encoding these polypeptides suggests local synthesis in the CNS (see Baskin et al., TINs 11:107–111 (1988) for review). In addition, IGF-III (or "brain IGF"), a truncated form of IGF-I lacking the latter protein's three N-terminal amino acid residues, has been found in fetal and adult human brain (Sara et al., Proc. Natl. Acad. Sci. USA 83:4904–4907 (1986), as well as in colostrum (Francis et al., Biochem. J. 251:95–103 (1988)). Two different IGF receptors have been identified in the adult human CNS (Baskin et al., 1988, supra), including in the brain (Sara et al., Neurosci. Let. 34:39–44 (1982)). In addition, European Patent No. 227,269 describes evidence for a third type of IGF receptor located in human fetal membranes. Complicating research in this area are (1) evidence that the insulin receptor of brain membranes recognizes not only insulin but also the IGFs; (2) the finding that one of the two types of adult IGF receptors exhibits some affinity for insulin as well as for both IGF-I and II, and (3) current uncertainty as to the physiological significance of binding of IGF-II to the second type of adult IGF receptor (Baskin et al., 1988, supra).

IGF-I and IGF-II appear to exert a stimulatory effect on development of proliferation of a wide range of susceptible cell types (see Daughaday et al., 1989, supra, for review). Treatment with the IGFs or with certain polypeptide fragments thereof has been variously suggested as a bone repair and replacement therapy (European Patent Application No. 289 314), as a means to counteract certain harmful side effects of carcinostratic drugs (Japanese Patent No. 63196524), and as a way to increase lactation and meat production cattle and other farm animals (Larsen et al., U.S. Pat. No. 4,783,524). Each of the IGFs also appears to enhance the survival, proliferation and/or neurite outgrowth of cultured embryonic neurons (which, unlike mature neurons, have not yet lost their ability to undergo cell division) from various parts of the CNS (Aizenman et al., Brain Res. 406:32–42 (1987); Fellows et al., Soc. Neurosci. Abstr. 13:1615 (1987); Onifer et al., Soc. Neurosci. Abstr. 13:1615 (1987); European Patent No. 227,619 and from the peripheral nervous system (Bothwell, J. Neurosci Res. 8:225–231 (1982); Recio-Pinto et al., J. Neurosci 6:1211–1219 (1986)). In addition, the IGFs have been shown to affect the development of undifferentiated neural cells: human neuroblastoma tumor cells were shown to respond to added IGFs by extending neurites (Recio-Pinto and Ishii, J. Neurosci. Res. 19:312–320 (1988)) as well as by undergoing mitosis (Mattson et al., J. Cell Biol. 102:1949–54 (1986). As the induction of the enzyme ornithine decarboxylase has been shown to correlate with the stimulation of mitotic activity of these cells, an assay for cell proliferation has been developed based upon measuring the level of activity of this enzyme (Mattsson et al., 1986).

Developing forebrain cholinergic neurons (cultured rat septal neurons) are sensitive to a variety of growth factors in vitro. Addition of nerve growth factor (NGF) to the culture medium increases the number of cells positive for the expression of transmitter-specific enzymes (acetyl choline esterase (AChE) and choline acetyl transferase (ChAT)) (Hartikka and Hefti, J. Neuroscience 8:2967–2985 (1988). Thyroid hormone also increase the level of ChAT in cultured septal neurons and thyroid hormone in combination with NGF results in a stimulation of ChAt activity much greater than the sum of the effects of individual addition of these two substances (Hayashi and Patel, Dev. Brain Res. 36:109–120 (1987)). IGF-I, IGF-II, and insulin also induce ChAT activity in cultured septal neurons (Knusel et al., J. of Neuroscience 10:558–570 (1990)). When NGF and insulin are both added to the culture medium the effect on ChAT activity is additive, but the effects of IGF-I or IGF-II in combination with insulin are not additive (Knusel et al., 1990, supra).

In vivo studies also support the hypothesis that the IGFs play a role in development and differentiation of the immature peripheral and central nervous systems (Sara et al., J. Dev. Physiol. 1:343–350 (1979); Phillips et al., Pediatr. Res. 23:298–305 (1988); Sara et al., Prog. Brain Res. 73:87–99 (1988)), although the physiological nature of this Role remains uncertain. Once the neuronal cells of the CNS reach maturity, they do not undergo further cell division.

Neurotrophic factors other than the IGFs have been proposed as a potential means of enhancing neuronal survival, for example as a treatment for the neurodegenerative disease amyotrophic lateral sclerosis (using skeletal muscle-derived proteins having apparent molecular weights in the 20,000–22,000 dalton and 16,000–18,000 dalton ranges: PCT Application No. PCT/US88/01393), and Alzheimer's disease (using phosphoethanolamine: PCT Application No. PCT/US/88/01693). Sara et al., although finding a "significant elevation" in serum and cerebrospinal fluid somatomedin (IGF) levels in patients suffering from Alzheimer's disease compared to normal controls, nevertheless conclude:

Whether somatomedins play a casual (sic) role in the etiology of the dementia disorders of the Alzheimer type remains to be determined. However, since somatomedins stimulate the uptake of amino acids into brain tissue, their administration may provide beneficial therapeutic effects. Finally, the fall in somatomedins observed in normal elderly patients raises the general question of their role in cell aging. (citation omitted; Sara et al., Neurobiol. Aging 3:117–120, 119 (1982)).

In a report that IGF-I, but not IGF-II, stimulates the immediate (i.e. within 20 min.) release of acetylcholine from slices of adult rat brain, a process thought to be related to transitorily increased neurotransmission of acetylcholine rather than to increased cholinergic enzyme activity, Nilsson et al., Neurosci. Let. 88:221–226, 221, 224 (1988), point out that

[One] of the major deficits in Alzheimer's disease concerns the cholinergic system of the brain, where a reduced synthesis and release of [acetylcholine] has been found. . . . It is of considerable importance to further investigate the role of IGFs in neurodegenerative disorders such as Alzheimer's disease . . . (citations omitted).

Using antibody specific for IGF-I to detect an increase in the presence of IGF-I in injured peripheral nerves, notably in the non-neuronal cells named "Schwann cells", Hansson et al., Acta Physiol. Scand. 132:35–41, 38, 40 (1988), suggest that Thus, increased IGF-I immunoreactivity is observed in regenerating peripheral nerves after any injury and seems to form part of a general reaction pattern, most evident in the Schwann cells. Our ultrastructural studies have revealed that the Schwann cells undergo hypertrophy after vibration trauma, and show signs of activation, i.e. the granular endoplasmic reticulum and Golgi complex increased in extent. We thus interpret the increase in IGF-I immunoreactivity in the Schwann cells, documented in this study on vibration-exposed nerves, as part of a transient, reactive response beneficial for the early stages of repair processes. . . . We consider the increase in IGF-I immunoreactivity to reflect mainly the initial reactions in a chain of events resulting in repair of the injured tissue or organ [although this increase] may be interpreted to reflect disturbed axoplasmic transport [of IGF-I molecules], due in part to the diminution of microtubules reported to occur after vibration exposure. (citation omitted)

Further, Sjoberg et al., Brain Res. 485:102–108 (1989), have found that local administration of IGF-I to an injured peripheral nerve stimulates regeneration of the nerve as well as proliferation of associated non-neuronal cells.

Several methods have been employed to decrease the susceptibility of polypeptides to degradation by peptidases, including, e.g., substitution of D-isomers for the naturally-occurring L-amino acid residues in the polypeptide (Coy et al., Biochem. Biophys. Res. Commun. 73:632–8 (1976)). Where the polypeptide is intended for use as a therapeutic for disorders of the CNS, an additional problem must be addressed: overcoming the so-called "blood-brain barrier," the brain capillary wall structure that effectively screens out all but selected categories of molecules present in the blood, preventing their passage into the brain. While the blood-brain barrier may be effectively bypassed by direct infusion of the polypeptide into the brain, the search for a more practical method has focused on enhancing transport of the polypeptide of interest across the blood-brain barrier, such as by making the polypeptide more lipophilic, by conjugating the polypeptide of interest to a molecule which is naturally transported across the barrier, or by reducing the overall length of the polypeptide chain (Pardridge, Endocrine Reviews 7:314–330 (1986); U.S. Pat. No. 4,801,575.

SUMMARY OF THE INVENTION

In general, the invention features a method of enhancing the survival of neuronal cells at risk of death, preferably non-mitotic neuronal cells and/or cholinergic neuronal cells, in a mammal, preferably in the context of a therapeutic treatment of neuronal tissues which are suffering from the effects of aging, of injury, or of a disease e.g., Alzheimer's disease, stroke, epilepsy, amyotrophic lateral sclerosis, or Parkinson's disease, by administering to the mammal an effective amount of at least one of the following: IGF-I, a functional derivative of IGF-I, IGF-II, or a functional derivative of IGF-II, IGF-III, or a functional derivative of IGF-III, with or without the administration of an effective amount of NGF, ciliary neurotrophic factor (CNTF), or a functional derivative thereof.

The invention also features a method of enhancing the survival of neuronal cells at risk of death, preferably non-mitotic neuronal cells and/or cholinergic neuronal cells, in a mammal, preferably in the context of a therapeutic treatment of neuronal tissues which are suffering from the effects of aging, or injury, or of a disease, e.g., Alzheimer's disease, stroke, epilepsy, amyotrophic lateral sclerosis, or Parkinson's disease, by treating said mammal with a first treatment including administration of a cell survival promoting amount of a growth factor, e.g., IGF-I, IGF-II, or IGF-III, or a functional derivative of the growth factor (e.g., a fragment, analog, or analog of a fragment of the first growth factor), alone, or in a biologically active combination with another such growth factor or functional derivative, and then treating said mammal with a second treatment including administration of a nerve transmitter increasing amount of a transmitter enhancer e.g., NGF, CNTF, or a functional derivative of the transmitter enhancer (e.g., a fragment, analog, or analog of a fragment of the transmitter enhancer). In preferred embodiments, fragments, analogs, or analogs of fragments of IGF-I, IGF-II, IGF-III, or NGF are administered.

The invention also features a method of enhancing the cholinergic activity (i.e., acetylcholine-synthesizing capacity) of cholinergic neuronal cells in a mammal, preferably non-mitotic neuronal cells, and preferably in the context of a therapeutic treatment of neuronal tissues which are suffering from the effects of aging, of injury, or of a disease, e.g., Alzheimer's disease, stroke, epilepsy, amyotrophic lateral sclerosis, or Parkinson's disease, by administering to the mammal in effective amount of one or more of the following: IGF-I, IGF-II, IGF-III, a functional derivative of IGF-I, or a functional derivative of IGF-II or a functional derivative of IGF-III (preferably administering a fragment of IGF-I, IGF-II, or IGF-III, or, alternatively, administering an analog of IGF-I, of IGF-II, or an analog of a fragment of IGF-I or IGF-II), with or without the administration of an effective amount of NGF, CNTF, or a functional derivative thereof, provided that if IGF-I or IGF-II is administered, NGF or a functional derivative thereof is also administered.

The invention also features a method of enhancing the cholinergic activity (i.e., acetylcholine-synthesizing capacity) of cholinergic neuronal cells in a mammal, preferably non-mitotic neuronal cells, and preferably in the context of a therapeutic treatment of neuronal tissues which are suffering from the effects of aging, or injury, or of a disease, e.g., Alzheimer's disease, stroke, epilepsy, amyotrophic lateral sclerosis, or Parkinson's disease, by treating said mammal with a first treatment including administration of a cell survival promoting amount of a growth factor, e.g., IGF-I, IGF-II, or IGF-III, or a functional derivative of the growth factor (e.g., a fragment, analog, or analog of a fragment), alone, or in a biologically active combination with another such growth factor or functional derivative, and then treating said mammal with a second treatment including an administration of a nerve transmitter increasing amount of a transmitter enhancer, e.g., a factor that increases the level of a transmitter specific enzyme in the cell, e.g., NGF, CNTF, or a functional derivative of a transmitter enhancer (e.g., a fragment, analog, or analog of a fragment).

Another method of the invention features treating a head or spinal cord injury of a mammal, or a disease condition of a mammal, e.g., stroke, epilepsy, age-related neuronal loss, amyotrophic lateral sclerosis, Alzheimer's disease, or Parkinson's disease, by (1), administering to the mammal an effective amount of at least one of the following substances: IGF-I, a functional derivative of IGF-I, IGF-II, a functional derivative of IGF-II, IGF-III, or a functional derivative of IGF-III, with or without the administration of NGF, CNTF, or a functional derivative thereof, or by (2), treating said mammal with a first treatment including administration of a cell survival promoting amount of one or more of a first group of substances, e.g., IGF-I, a functional derivative of IGF-I, IGF-II, a functional derivative of IGF-II, IGF-III, or a functional derivative of IGF-III, and then treating said mammal with a second treatment including administration of a nerve transmitter increasing amount of a transmitter enhancer or a functional derivative thereof, e.g., NGF, CNTF, or a functional derivative thereof.

A particular advantage of the use of combined treatments as described above is the ability to reduce the required dose of one component, e.g., CNTF, which alone in a higher dose may exhibit unwanted side effects, i.e., toxicity.

The invention also features a method of modifying a ligand, preferably a neuroactive polypeptide, capable of binding to a receptor located on a cell surface, by first binding the ligand to a preparation of said receptor, then performing the modification procedure (preferably cationization, glycosylation, or increasing the lipophilicity of the polypeptide), and then releasing the modified ligand from the receptor.

The invention also features a method of enhancing neurite regeneration in a mammal; the method involving treating the mammal with a first treatment involving administration of a neurite regenerating amount of a growth factor, or a functional derivative thereof, and then treating the mammal with a second treatment involving administration of a nerve transmitter increasing amount of a transmitter enhancer, or a functional derivative thereof. The functional derivative of the growth factor may preferably be IGF-II (54–67) (SEQ ID NO:3), IGF-II(58–67) (SEQ ID NO:2), TYCAPAKSE (SEQ ID NO:1), IGF-I(55–70) (SEQ ID NO:4), or an analog of the growth factor, or an analog of a fragment of the growth factor, more preferably IGF-II(54–67; D-Y)(SEQ ID NO:45), or IGF-II(58–67; D-Y)(SEQ ID NO:46), or any of the other peptides listed herein.

Polypeptides administered in methods of the invention may be chemically modified in such a way as to increase the transport of the polypeptide across the blood-brain barrier, e.g., by modifications of the polypeptide that increases lipophilicity, alter glycosylation, or increase net positive charge.

Embodiments of the invention include the administration of more than one neuroactive polypeptide. In preferred embodiments the combined desired effect of administration of the polypeptide is additive, and in more preferred embodiments the effect is synergistic.

In other preferred embodiments, where a fragment of IGF-II is administered, preferred IGF-II fragments include, but are not limited to, IGF-II(54–67) (SEQ ID NO:3), IGF-II(58–67) (SEQ ID NO:2), or may include analogs of IGF-II fragments, e.g., TYCAPAKSE (SEQ ID NO:1), IGF-II(54–67; D-Y) (SEQ ID NO:45), or IGF-II(58–67; D-Y) (SEQ ID NO:46). Where a fragment of IGF-I or IGF-III is administered, preferred IGF-I,III fragments may include IGF-I(55–70) (SEQ ID NO:4).

The invention also features a composition including a first component taken from the group of purified IGF-I, a purified functional derivative of IGF-I, purified IGF-II, a purified functional derivative of IGF-II, purified IGF-III, or a purified functional derivative of IGF-III, and a second component taken from the group of purified NGF, or a purified functional derivative of NGF. Purified means that the substance is of 95% or greater (by weight) purity, i.e., that it is substantially free of proteins, lipids, and carbohydrates with which it is naturally associated.

In another aspect, the invention includes a substantially pure peptide, wherein the peptide includes a sequence selected from the group consisting of the amino acid sequence TYCATPAK (SEQ ID NO:51), LETYCATP (SEQ ID NO:52), CATPAKSE (SEQ ID NO:53), YCAPAKSE (SEQ ID NO:54), YCAPA (SEQ ID NO:55), TYCAPA (SEQ ID NO:56), CAPARSE (SEQ ID NO:24), EALLETYCATPAKSE (SEQ ID NO:36), ALLEKYCAKPAKSE (SEQ ID NO:37), and APSTCEYKA (SEQ ID NO:38). As a preferred embodiment, these peptides can be used in any of the various methods of the invention.

The invention also includes the substantially pure peptides TYCAPAKSE (SEQ ID NO:1), TDYCAPAKSE (SEQ ID NO:50)DY and D-Y, as used herein, refer to the D-isomer of Tyrosine, IGF-II(54–67)(SEQ ID NO:3), IGF-II(58–67) (SEQ ID NO:2), IGF-I(55–70)(SEQ ID NO:4), EPYCAPPAKSE (SEQ ID NO:5), or analogs of the above peptides, preferably wherein tyrosine-59 is a D-isomer of tyrosine, e.g., IGF-II(54–67; D-Y) (SEQ ID NO:45) or IGF-II(58–67); D-Y) (SEQ ID NO:46). Where a fragment of IGF-I or IGF-III is administered, preferred IGF-I and IGF-III fragments may include IGF-I(55–70) (SEQ ID NO:4).

The invention also includes a cyclic peptide, preferably of 5–40 amino acids, and most preferably of 6–25 amino acids. Preferably the cyclic peptide includes a fragment of the respective IGF-I, IGF-II, or IGF-III as at least a portion of its amino acids sequence. The cyclic peptide can include a disulfide bond between two cysteines of the peptide, the cysteines being located at either terminal or internal positions of the peptide. Alternatively or in addition to the disulfide bond, the cyclic peptide may include an amide bond between the amino and carboxyl ends of the peptide. Preferred cyclic peptides include, but are not limited to, those derived by cyclization, e.g., by disulfide bond formation or by amide bond formation, of the following peptides: CALLETYCATPAKSEC (SEQ ID NO:6), CTYCATPAKSEC (SEQ ID NO:7), CEPYCAPPAKSEC (SEQ ID NO:8), CTYCAPAKSEC (SEQ ID NO:9), CALLETDYCATPAKSEC (SEQ ID NO:47), CTDYCATPAKSEC (SEQ ID NO:48), CTDYCAPAKSEC (SEQ ID NO:49), CTYTAPAKSEC (SEQ ID NO:10), CALLETYATPAKSEC (SEQ ID NO:11), CRRLEMYCAPLKPAKSAC (SEQ ID NO:12), CGYGSSSRRAPQTC (SEQ ID NO:13), CYFNKPTGYGC (SEQ ID NO:14), CYFNKPTGYGSSSRRAPQTC (SEQ ID NO:15), CKPTGYGSSSRC (SEQ ID NO:16), the amino acid sequence CGCELVDALQFVC (SEQ ID NO:18), the amino acid sequence CDLRRLEMYCCPLKPAKSE (SEQ ID NO:21), CGPETCL (SEQ ID NO:26), CGYGSSSR-RCPQTGIVDEC (SEQ ID NO:27), CGDRGFYFNKPTC (SEQ ID NO:28), CCPLKPAKSAC (SEQ ID NO:29), CDL-RRLEMYAPLKPAKSAC (SEQ ID NO:30), the amino acid sequence CDLCLLETYC (SEQ ID NO:33), the amino acid sequence CDLCLLETYCATPAKSE (SEQ ID NO:35), CCYRPSETLC (SEQ ID NO:40), CRPCSRVSRRSR-GIVEEC (SEQ ID NO:41), CGDRGFYFSRPC (SEQ ID NO:42), CCTPAKSEC (SEQ ID NO:43), AND CDLCLLE-TATPAKSEC (SEQ ID NO:44). Amino acid residues of the cyclic peptides can be in the form of either L-amino acids, or in the form of an amino acid analog listed in Table 2, e.g., D-amino acids. The residues flanking the amino acid sequence are preferably homologous to the naturally occurring sequence of IGF-I or to the naturally occurring sequence of IGF-II.

The invention also includes a substantially pure peptide, wherein the peptide is selected from the group consisting of the amino acid sequence CDLRRLEMYC (SEQ ID NO:19), the amino acid sequence CCFRSCDLRRLEMYC (SEQ ID NO:20), the amino acid sequence CCFRSC (SEQ ID NO:22), and the amino acid sequence CFRSC (SEQ ID NO:23), wherein the peptide is cyclized by a covalent bond between two residues of the peptide.

The invention also includes a substantially pure peptide, wherein the peptide is selected from the group consisting of the amino acid sequence CGGELVDTLQFVC (SEQ ID NO:32), the amino acid sequence CCFRSCDDLALLETYC (SEQ ID NO:34), wherein the peptide is cyclized by a covalent bond between two residues of the peptide.

The invention also includes a substantially pure cyclized peptide consisting essentially of the amino acid sequences CGCELVDALQFVC (SEQ ID NO:18) and CCFRSCDLR-RLEMYC (SEQ ID NO:20), wherein the cyclized peptide includes at least one covalent bond between two residues of the looped peptide.

The invention also includes a substantially pure cyclized peptide consisting essentially of the amino acid sequences CGGELVDTLQFVC (SEQ ID NO:32) and CCFRSCDL-CLLETYC (SEQ ID NO:39), wherein the cyclized peptide includes at least one covalent bond between two residues of the cyclized peptide.

As a preferred embodiment to any of the various methods of the invention, the functional derivative is a retro-inverso peptide, preferably a retro-inverso peptide that is homologous to IGF-I, or a fragment thereof, or a retro-inverso peptide that is homologous to IGF-II, or a fragment thereof. A "retro-inverso peptide", as used herein, refers to a peptid with a reversal of the direction of the peptide bond at at least one position, i.e., a reversal of the amino- and carboxy-termini with respect to the side chain of the amino acid. Retro-inverso peptides may contain L-amino acids or D-amino acids, or a mixture of L-amino acids and D-amino acids.

With respect to any of the IGF-I or IGF-II peptides listed herein, most preferred are linear and cyclic peptides that contain at least one cysteine residue that is not involved in disulphide bond formation. In some cases where a naturally-occurring alanine has been changed to a cysteine, the invention embodies both the peptide containing the naturally-occurring alanine, which has at least partial activity, as well as the peptide containing the substituted cysteine, which has the preferred activity. Any of the peptides of the invention may be iodinated.

"Homologous" refers to the sequence similarity between two polypeptide molecules or between two nucleic acid molecules. When a position in both of the two compared sequences is occupied by the same base or amino acid monomeric subunit, e.g., if a position in each of two polypeptide molecules is occupied by leucine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the amino acid sequences Leu-gly-val-ala-gly-pro and Leu-his-tyr-ala-gly-leu share 50% homology.

In addition to substantially full-length polypeptides, the invention also includes fragments of the IGF-I, IGF-II, or IGF-III polypeptides. As used herein, the term "fragment", as applied to a polypeptide, will ordinarily be at least about 5 contiguous amino acids, typically at least about 20 contiguous amino acids, usually at least about 40 contiguous amino acids, and preferably at least about 60 or more contiguous amino acids in length. Fragments of IGF I, II, or III can be generated by methods known to those skilled in the art.

The methods of the invention use IGF-I, IGF-II, IGF-III, functional derivatives of IGF-I, IGF-II, and of IGF-III, combinations thereof, and combinations thereof which also include NGF or functional derivatives of NGF to enhance the survival rate and/or the cholinergic activity of mammalian cells at increased risk of death due to some factor such as disease, injury, or natural aging processes, or where stimulation of cholinergic activity could have a beneficial effect on the mammal's condition. Some of the functional derivatives utilized by the method of the invention are known; others may be discovered by applying the routine methods disclosed herein. For instance, a functional derivative to be used in any of the various methods of the invention can be any fragment of analog of IGF-I, IGF-II, IGF-III, or any peptide that mimics the biological activity of IGF-I, IGF-II, or IGF-III, as determined by an assay described herein. Examples of such peptides can include IGF fragments containing conservative amino acid insertions, deletions or modified amino acids, cyclic peptides, retro-inverso peptides, or radiolabeled or iodinated peptides, as described herein. The peptides described herein are provided as examples, and are not to be construed as limiting the range of peptides useful for the methods of the invention.

Methods (and compositions) of the invention, e.g., the joint administration of IGF-I and NGF, enhance the survival and neurotransmitter-synthesizing capacity of cholinergic neurons in a previously unknown, complimentary manner.

Survival of a treated neuronal cell denotes maintenance of the cell's viability to an extent greater than that of untreated control cells. Since the preponderance of neuronal cells of the mature CNS are commonly believed to be incapable of cell division, the ability of an agent to promote the survival of such cells may be measured by an assay indicative of cellular trophic response, such as the ornithine decarboxylase assay disclosed herein. Alternatively, one can utilize any other assay which reproducibly indicates relative numbers of surviving cells, such as directly counting cells which stain as viable cells or which possess other characteristics of viable neurons, or assaying incorporation of appropriate labeled precusors into mRNA or protein. Where the effect of an added growth factor, functional derivatives, or a combination of growth factors and/or functional derivatives on the functioning of cholinergic neurons is of particular interest, an alternative assay that measures that functioning, such as the choline acetyltransferase or acetyl choline esterase assays disclosed herein, may be utilized.

Any of these approaches may be adapted to test the effect of treatment with growth factors, functional derivatives, or combinations of growth factors and/or functional derivatives on particular subsets of neurons known to be vulnerable in specific degenerative diseases, such as spinal cord cholinergic neurons in amyotrophic lateral scelerosis. A preliminary screen for polypeptides which bind to the IGF or NGF receptors may first be employed to indicate likely candidates for the assays described above, e.g., the cell survival or cholinergic activity assay; disclosed herein is an IGF-I-receptor displacement assay designed for such a purpose. Methods for measuring the ability of NGF or its functional derivatives to bind its receptors are known to those skilled in the arts. Those polypeptides which appear to promote cell survival or cholinergic activity under one or more of the above assays may be further tested, by appropriate in vivo administration, for their ability to counteract the degenerative effects of aging, injury or disease in the nervous system or other tissue of an animal.

The use of any polypeptide as a therapeutic raises the issue of stability of the polypeptide after administration to the organism, when it is exposed to the action of various peptides both within and without the target tissue. Where lack of such stability is expected to be a problem, certain stability-enhancing modifications disclosed herein may be made to the polypeptide. Other modifications designed to facilitate transport of the polypeptide across the blood-brain barrier may be made to the polypeptide, as disclosed herein.

The method of the invention is useful for therapeutically treating a disorder of a human or other mammal characterized by the death of cells, particularly neural cells, including disorders attributable to a disease or aging of, or injury to, such neuronal cells. The neurotrophic peptides, including the IGFs and/or their functional derivatives, and combinations of IGFs and/or their functional derivative with NGF or its functional derivatives are useful for the treatment of neurodegenerative diseases such as Alzheimer's disease, stroke, epilepsy, amyotrophic lateral sclerosis and Parkinson's disease, as well as general age-related neuronal loss, conditions which have proven particularly intractable to treatment by alternative methods.

Other features and advantages of the invention will be apparent from the following description of the preferred embodiments thereof, and from the claims.

DESCRIPTION OF THE PREFERRED EMBODIMENT(S)

The drawings are first described.
Drawings

The Peptides

Figure 1:
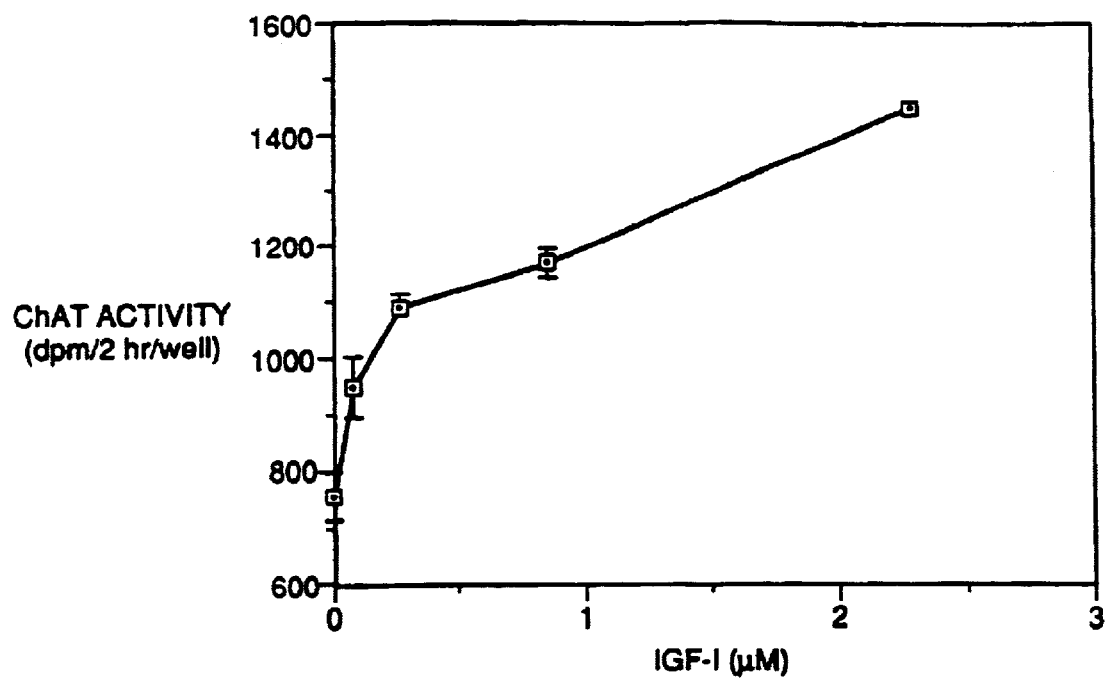
FIG. 1 is a graph illustrating the effect of IGF-I on the survival of cholinergic neurons in rat spinal cord cultures.

The present invention is directed, inter alia, to the modification of neuroactive polypeptides such as IGF-I and IGF-II and their functional derivatives, and their use, both with and without accompanying administration of NGF or functional derivatives of NGF, as therapeutics for certain neurological diseases or disturbances characterized by increased vulnerability of neurons to dying. A "neuroactive polypeptide" or "growth factor" is defined as a polypeptide which exerts a survival enhancing effect on neuronal cells: e.g., the IGFs, e.g., IGF-I and IGF-II, Nerve Growth Factor, (NGF), Epidermal Growth Factor, Fibroblast Growth Factor, and insulin. A "functional derivative" of a polypeptide is a compound which is a fragment, an analog, or an analog of a fragment of that molecules and which possesses the desired biological activity, herein defined as the ability to promote survival and/or cholinergic activity of neuronal cells. A "fragment" of a polypeptide refers to any polypeptide subset of that polypeptide. An "analog" of a polypeptide refers to a molecule having biological activity but possessing some structural differences compared to the polypeptide: e.g., an altered amino acid sequence, or the presence of additional chemical moieties not normally a part of the molecule. Such moieties (introduced, for example, by acylation, alkylation, cationization, or glycosylation reactions) may improve the molecule's solubility, absorption, transport, biological half-life, etc. Alternatively, or in addition, some moieties may decrease the toxicity of the molecule, or eliminate or attenuate any undesirable side effect of the molecule. Moieties capable of mediating such effects are disclosed in *Remington's Pharmaceutical Sciences* (Mack Pub. Co., Easton, Pa. 1980). Although some derivatives of IGF-I, IGF-II, and NGF may be inoperative alone or in combination, a person skilled in the art disclosed herein can recognize which are operative and which are not, as will be explained in more detail below. A "transmitter enhancer" is a polypeptide that causes an increases in the level of a transmitter. NGF is an example of a transmitter enhance. A "transmitter" is a neurotransmitter, e.g., acetyl choline. A "transmitter-specific enzyme" is an enzyme present in neurons and involved in transmitter metabolism, e.g., in the case of cholinergic neurons, acetyl choline esterase (AChE) or choline acetyl transferase (ChAT). A "neuronal cell" is a neuron.

Some of the compounds within the scope of this invention are depicted in Table 1, which shows the amino acid sequences (expressed using single-letter abbreviations as defined in Table 2) of IGF-I, IGF-II, and a number of functional derivatives of IGF-I and IGF-II. These derivatives were selected for study on the basis of one or more of the following criteria, which are related to the ability to bind to IGF-I or IGF-II receptors, and thus are useful for identifying additional functional derivatives of the invention: (1) conservation of amino acid sequence among species; (2) presence of "conservative" amino acid substitutions among species (i.e., amino acids with similar shape, charge or other salient characteristics); (3) receptor shielding of tyrosine residues from radioiodination (Maly and Luthi, J. Biol. Chem. 263:7068–7072 (1988); (4) predominance of hydrophilic residues, suggesting the location of a receptor-binding domain on the surface of the polypeptide, a presumptive requirement for receptor interaction; and (5) consideration of hydrophobic and polar regions of three-dimensional models (e.g., Blundell et al., Fed. Proc. 42:2592–2597 (1983)) and identifying therefrom regions which are possible binding sites. Analogous factors can be applied in the design of NGF functional derivatives.

TABLE 1

IGF PEPTIDE SEQUENCES

| Peptide Name | Sequence | Source | Cat. # |
|---|---|---|---|
| Human IGF-I (Somatomedin-C) | GPETL CGAEL VDALQ FVCGD RGFYF NKPTG YGSSS-- RRAPQ TGIVD ECCFR SCDLR RLEMY CAPLK PAKSA | AMGEN[1] | 14010 |
| Human IGF-I (Somatomedin-C) | GPETL CGAEL VDALQ FVCGD RGFYF NKPTG YGSSS-- RRAPQ TGIVD ECCFR SCDLR RLEMY CAPLK PAKSA | PENINSULA[2] | 9010 Lot 15578 |
| IGF-I(4–70) (Human Brain IGF) | TLCGAEL VDALQ FVCGD RGFYF NKPTG YGSSS-- RRAPQ TGIVD ECCFR SCDLR RLEMY CAPLK PAKSA | KABIGEN[3] KABIGEN[3] | Lot 88: 101G Lot S: 25 |
| IGF-I(24–41) | YFNKP TGYGS SSRRA PQT | PENINSULA[2] | 7308 Lot 007942 |
| | YFNKP TGYGS SSRRA PQT | BACHEM[4] | PGRO 080 Lot F297 |
| | YFNKP TGYGS SSRRA PQT | Synthetic[5] | |
| IGF-I(30–41) | GYGSS SRRAP QT | PENINSULA[2] | 7306 Lot 003251 |
| IFG-I(62–70) | APLKP AKSA | PENINSULA[2] | 7318 Lot 015726 |
| IGF-I(24–32) | YFNKP TGYG | Synthetic[5] | |
| IGF-I(24–41)-AMIDE | YFNKP TGYGS SSRRA PQT-NH$_2$ | Synthetic[6] | |
| IGF-I(33–41)-AMIDE | SSSRR APQT-NH$_2$ | Synthetic[6] | |
| 48-Acm-IGF-I(42–57)-AMIDE | Acm GIVDE CCFRS CDLRR L-NH$_2$ | Synthetic[7] | |
| IGF-I(33–41) | SSSRR APQT | Synthetic[5] | |
| IGF-I(28–41) | PTGYG SSSRR APQT | Synthetic[5] | |
| IGF-I(27–36) | KPTGY GSSSR | Synthetic[5] | |
| IGF-II(54–67) | ALLET YCATP AKSE | PENINSULA[2] | 7308 Lot 010718 |
| IGF-II(62–67) | TPAKS E | | |
| IGF-II(33–40) | SRVSR RSR | PENINSULA[2] | 7304 Lot 016905 |
| IGF-II | AYRPS ETLCG GELVD TLQFV CGDRG FYFSR PASRV | COLLA-BORATIVE[8] | LOT 89-0172 |
| Somatomedin-A | SRRSR GIVEE CCFRS CDLAL LETYC ATPAK SE | COLLA-BORATIVE[8] | LOT 89-0401 |

[1]Amgen, Thousand Oaks, CA 91320
[2]Peninsula Laboratories, Belmont, CA 94002
[3]Kabigen AB, S-112 87, Stockholm, Sweden
[4]Bachem, Inc., Torrance, CA 90505
[5]Synthesized on a Biosearch Solid Phase Peptide Synthesizer Model 9600 using Fmoc-Amino Acids linked to p-alkoxybenzyl alcohol resins supplied by Bachem Bioscience, Inc. Philadelphia, PA 19104.
[6]Synthesized on a Biosearch Solid Phase Peptide Synthesizer Model 9600 using 4-(2',4'-Dimethoxyphenyl-Fmoc-aminomethyl)-phenoxy Resin (Ae4719) supplied by Novabiochem, AG Laufelfingen, Switzerland.
[7]Synthesized on a Biosearch Solid Phase Peptide Synthesizer Model 9600 using the resin identified in footnote [6] Acm = Acetamidomethyl substituent on the cysteine side-chain sulfur atom.
[8]Collaborative Research, Inc., Bedford, MA 01730

Since the ability of peptides to penetrate the blood-brain barrier is related to their lipophilicity or their net ionic charge, suitable modifications of these peptides (e.g., by substituting pentafluorophenylalanine for phenylalanine, or by conjugation to cationized albumin) to increase their transportability (Kastin et al, Pharmac Biochem. Behav. 11:713–716 (1979); Rapoport et al., Science 207:84–86 (1980); Pardridge et al., Biochem. Biophys. Res. Commun. 146:307–313 (1987); Riekkinen et al., Peptides 8:261–265 (1987)) may be important for their bioavailability following administration outside the blood-brain barrier, and these modifications are within the scope of the invention. In addition, since bioavailability of peptides may be limited by their susceptibility to degradation by proteases and peptidases (Littlewood, et al., Neurochem Int. 12:383–389 (1988)), modifications of these peptides (e.g., replacement of L-amino acids with D-amino acids) to increase their metabolic stability (Coy et al., 1976) may also be important for their therapeutic efficacy, and these modified peptides are also within the scope of the invention.

Functional derivatives of the invention include, among others, peptides that vary from the native IGF or NGF molecules in any one or more of the following ways:

1. Chemical modification of the amino and carboxyl groups present at the respective ends of the peptides.
2. Replacement of one or more of the amino acid residues in the native sequence with biologically compatible other amino acid residues.
3. Replacement of one or more of the amino acid residues in the native sequence with chemically modified, biologically compatible other amino acid residues.
4. Deletion of one or more of the amino acid residues in the native sequence.
5. Repetition of one or preferably a sequence of several amino acid residues in the native sequence, with or without chemical modification to, or replacement or deletion of, one or more of the members of the sequence.
6. Cyclization, that is, joining the amino and carboxyl ends of the linear peptide.
7. Linkage of a IGF-I, IGF-II, IGF-III, CTNF, NGF, or functional derivatives of any of IGF-I, IGF-II, IGF-III, CTNF, or NGF with another molecule such as a polypeptide (e.g., another fragment of IGF-I, IGF-II, IGF-III, CTNF, or NGF) or a carbohydrate, by means of a disulfide, peptide, ester or other covalent bond.
8. Depsi peptide analogs.
9. Retro-Inverso peptides.

Examples of some of the functional derivatives of the invention are shown in Table 3, and further described in Table 4. The amino acid and molecular mass analyses of the Table 3 peptides are summarized in Table 4.

The invention also utilizes as a preferred subgroup within the IGF functional derivatives described above, those functional derivatives having the sequence: $R_1$—$AA_1$—$AA_2$—$AA_3$—$AA_4$ ... $AA_n$—$R_2$, wherein $AA_1$, $AA_2$, $AA_3$, $AA_4$ ... $AA_n$ are amino acid residues of IGF or of the IGF-peptide subsets or are conservative replacements for them as defined in Table 2, and n is any integer from 5 to 70 for IGF-I functional derivatives and 5–67 for IGF-II functional derivatives. $R_1$ is attached to the amino group of $AA_1$ and selected from the group of hydrogen, lower ($C_{1-6}$) alkyl, lower alkyl carbonyl, lower alkenyl, lower alkynyl, formyl, lower (C6–10) aryl, aroyl, aryloxy-carbonyl, aralkoxy-carbonyl, lower alkyloxycarbon, benzoyl, 1- or 2-thenoyl, nicotinoyl, dihydronicotinoyl, N-alkyldihydronicotinoyl, isonicotinoyl, and N-alkyldihydroisonicotinoyl. The carboxyl-terminal substituent ($R_2$) of the peptides is selected from the following: OH; $NH_2$; $OR_3$, wherein $R_3$ is a lower alkyl or a lower aryl; $OR_3OH$, wherein $R_3$ is defined as above; and NH—$R_3$ or $N(CH_3)R_3$, wherein $R_3$ is defined as above. Alternatively, the carboxyl group of the carboxyl-terminal amino acid may be replaced by any one of —$PO_3H_2$, $B(OH)_2$, —$CH_2OH$, —$SO_3H$ or a 5-tetrazole group.

TABLE 2

CONSERVATIVE AMINO ACID REPLACEMENTS

| For Amino Acid | Code | Replace with |
|---|---|---|
| Alanine | A | D-Ala, Gly, Aib, β-Ala, Acp, L-Cys, D-Cys, or delete |
| Arginine | R | D-Arg, Lys, D-Lys, homo-Arg, D-homo-Arg, Met, Ile, D-Met, D-Ile, Orn, D-Orn or delete |
| Asparagine | N | D-Asn, Asp, D-Asp, Glu, D-Glu, Gln, D-Gln, or delete |
| Aspartic Acid | D | D-Asp, D-Asn, Asn, Glu, D-Glu, Gln, D-Gln, or delete |
| Cysteine | C | D-Cys, S-Me-Cys, Met, D-Met, Thr, D-Thr, or delete |
| Glutamine | Q | D-Gln, Asn, D-Asn, Glu, D-Glu, Asp, D-Asp or delete |
| Glutamic Acid | E | D-Glu, D-Asp, Asp, Asn, D-Asn, Gln, D-Gln, or delete |
| Glycine | G | Ala, D-Ala, Pro, D-Pro, Aib, β-Ala, Acp or delete |
| Isoleucine | I | D-Ile, Val, D-Val, AdaA, AdaG, Leu, D-Leu, Met, D-Met, or delete |
| Leucine | L | D-Leu, Val, D-Val, AdaA, AdaG, Leu, D-Leu, Met, D-Met or delete |
| Lysine | K | D-Lys, Arg, D-Arg, homo-Arg, D-homo-Arg, Met, D-Met, Ile, D-Ile, Orn, D-Orn or delete |
| Methionine | M | D-Met, S-Me-Cys, Ile, D-Ile, Leu, D-Leu, Val, D-Val or delete |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa or delete |
| Proline | P | D-Pro, L-I-thiazolidine-4-carboxylic acid, D-or L-1-oxazolidine-4-carboxylic acid (Kauer, U. S. Pat. No. (4,511,390) or delete |
| Serine | S | D-Ser, Thr, D-Thr, allo-Thr, Met, D-Met, Met(O), D-Met(O), L-Cys, D-Cys, or delete |
| Threonine | T | D-Thr, Ser, D-Ser, allo-Thr, Met, D-Met, Met(O), D-Met(O), Val, D-Val or delete. |
| Tyrosine | Y | D-Tyr, Phe, D-Phe, L-Dopa, His, D-His or delete |
| Valine | V | D-Val, Leu, D-Leu, Ile, D-Ile, Met, D-Met, AdaA, AdaG or delete |

The invention also utilizes as a preferred subgroup within the NGF functional derivatives described above, those functional derivatives having the sequence: $R_1$—$AA_1$—$AA_2$—$AA_3$—$AA_4$ ... $AA_n$—$R_2$, wherein $AA_1$, $AA_2$, $AA_3$, $AA_4$ ... $AA_n$ are amino acid residues of NGF or its functional derivatives or are conservative replacements for them as defined in Table 2, and n is an integer corresponding to the number of amino acid residues in NGF or in a functional derivative thereof. $R_1$ is attached to the amino group of $AA_1$ and selected from the group of hydrogen, lower ($C_{1-6}$) alkyl, lower alkyl carbonyl, lower alkenyl, lower alkynyl, formyl, lower ($C_{6-10}$) aryl, aroyl, aryloxy-carbonyl, aralkoxy-carbonyl, lower alkyloxycarbonyl, benzoyl, 1- or 2-thenoyl, nicotinoyl, dihydronicotinoyl, N-alkyldihydronicotinoyl, isonicotinoyl, and N-alkyldihydroisonicotinoyl. The carboxyl-terminal substituent ($R_2$) of the peptides is selected from the following: OH; $NH_2$; $OR_3$, wherein $R_3$ is a lower alkyl or a lower aryl; $OR_3OH$, wherein $R_3$ is defined as above; and NH-$R_3$ or $N(CH_3)R_3$, wherein $R_3$ is defined as above. Alternatively, the carboxyl group of the carboxyl-terminal amino acid may be replaced by any one of —$PO_3H_2$, —$B(OH)_2$, —$CH_2OH$, —$SO_3H$ or a 5-tetrazole group.

The amino-terminal amino group and/or the lysine, serine or threonine side chains occurring within the peptide may optionally be acylated by formyl, acetyl, propionyl, and similar lower alkylacyl residues or by aryl or heterocyclic acyl residues such as benzoyl, thenoyl, nicotinoyl, isonicotinoyl, N-alkylnicotinoyl and their dihydro and tetrahydro derivatives. Such modifications would be expected to enhance the blood-brain barrier permeability of the therapeutic agent (Creveling et al., Experientia 25:26–27 (1969); Bodor et al., Science 214:1370–1372 (1981)).

In peptide sequences containing proline, glutamic acid, or aspartic acid at the amino-terminus, the amino terminal amino acid may optionally be replaced by L-pyroglutamic acid.

The fragment polypeptides of IGF-I, IGF-II, and NGF are subsets of the IGF-I, IGF-II, and NGF molecules (respectively) containing fewer amino acid residues than the native molecules. Preferred IGF sequences are of 5–50 residues and most preferred are sequences of 6–25 residues. A portion of the amino acids of the fragments may be substituted with conservative replacements, deletions, or insertions that improve the chemical or biological stability of the product peptides or improve their transport across the blood-brain barrier. Preferably, no more than 30% and more preferably no more than 20%, of the amino acid residues are replaced or deleted. A listing of suitable conservative replacements is given in Table 2, along with a key to the single-letter abbreviations for the common, naturally-occurring amino acid residues found in proteins. Certain other abbreviations used in Table 2 are herein defined: by Nle is meant norleucine, by Aib is meant aminoisobutyric acid, by AdaA is meant β-adamantylalanine, by AdaG is meant α-adamantylglycine, by homo-Arg is meant L-homoarginine, by D-homo-Arg is meant D-homoarginine, by Acp is meant ε-aminocaproic acid, by Chg is meant L-α-cyclohexylglycine, by D-Y is meant D-Tyrosine, and by allo-Thr is meant L-allothreonine. Additionally, by Cha is meant β-cyclohexylalanine, by Me is meant methyl (CH₃), by Orn is meant ornithine, by pyro-Glu is meant the pyroglutamyl group, by Met(O) and D-Met(O) are meant the sulfoxides derived from L- and D-methionine, respectively, by β-Ala is meant β-alanine, by Acm is meant acetamidomethyl, by L-Dopa is meant 3-(3,4-dihydroxyphenyl)-L-alanine, and by Bpa is meant 4-benzoylphenylalanine.

The symbolism and abbreviations used are otherwise those recommended by the IUPAC-IUB Joint Commission on Biochemical Nomenclature, "Nomenclature and Symbolism for Amino Acids and Peptides, Recommendations 1983" J. Biol. Chem. 260:14–42 (1985). As is conventional, these same symbols are used to define the corresponding residues of the amino acids when they are linked into a peptide chain. Where the amino acid residue has isomeric forms, it is the L-form of the amino acid that is represented unless otherwise expressly indicated. In accordance with conventional representation, the amino group at the N-terminus of each peptide appears to the left and the carboxyl group at the C-terminus to the right.

Besides the amino acid substitutions suggested above, other methods of improving transport of the polypeptide across the blood-brain barrier, such as chemical modification of the polypeptide, may be employed. In any chemical modification procedure, the polypeptide may first be attached to its receptor in order to protect and maintain the receptor-binding site structure during the chemical modification process, which can comprise, for example, cationization (according to the method, for example, of Pardridge et al., 1987) or glycosylation (according to the method of Schwartz et al., Arch. Biochem. Biophys. 181:542–549 (1977)).

Cyclic Peptides

The invention also utilizes as a preferred subgroup within the IGF functional derivatives described above, cyclic peptides, preferably of 5–40 amino acid residues, and most preferably of 6–25 amino acid residues. Such peptides are preferably modeled after the looped domains of the IGF molecules. Such loops may be a consequence of natural disulfide bond formation, while others are a consequence of the folding of the protein as it achieves a minimal energy conformation or a receptor-induced conformation to permit binding. As stated above, cyclization can be effected by joining the amino and carboxyl ends of a linear peptide, either directly to form an amide (lactam) bond (Example 25B), or by disulfide bond formation employing terminal cysteine groups. Any internal cysteine groups present are preferably selectively blocked before cyclization and may be unblocked afterward using well-established procedures (Example 25A). Alternatively, internal cysteines may be replaced by an amino acid which would be expected to have a minimal influence on peptide conformation, e.g. alanine, which is frequently used in scanning mutagenesis studies.

Examples of preferred cyclic peptides include those derived by cyclization of the following monomeric peptides via disulfide bond formation of the terminal cysteine groups:
CALLETYCATPAKSEC (SEC ID NO:6)
CYYCATPAKSEC (SEQ ID NO:7)
CEPYCAPPAKSEC (SEQ ID NO:8)
CTYCAPAKSEC (SEQ ID NO:9)
CALLETDYCATPAKSEC (SEQ ID NO:47)
CTDYCATPAKSEC (SEQ ID NO:48)
CTDYCAPAKSEC (SEQ ID NO:49)
CTYTAPAKSEC (SEQ ID NO:10)
CALLETYATPAKSEC (SEC ID NO:11)
CRRLEMYCAPLKPAKSAC (SEC ID NO:12)
CGYGSSSRRAPQTC (SEC ID NO:13)
CYFNKPTGYGC (SEQ ID NO:14)
CYFNKPTGYGSSSRRAPQTC (SEQ ID NO:15)
CKPTGYGSSSRC (SEQ ID NO:16)

An example of a cyclic peptide formed by amide bond formation is the following:
Cyclic (TYCAPAKSE) (SEQ ID NO:1)

Examples of preferred cyclic peptides based on looped domains of the IGF-I and IGF-II molecules are the following:

IGF I
(SEQ ID NO: 17)
GPETLCGAELVDALQFVCGDRGFYFNKPTGYGSSSRRAPQTG
|                    \
IVDECCFRSCDLRRLEMYCAPLKPAKSA
|_____|

LOOP PEPTIDES PROPOSED:

1. Using Cys present in IGF I.

a) CGCELVDALQFVC       6–18[2]      (SEQ ID NO: 18)
   |_____| b) CDLRRLEMYC          52–61        (SEQ ID NO: 19)
   |_____| c) CCFRSCDLRRLEMYC     47–61        (SEQ ID NO: 20)
   |_____| d) CDLRRLEMYCCPLKPAKSE  52–70       (SEQ ID NO: 21)
   |_____| e) CCFRSC              47–52        (SEQ ID NO: 22)
   |____|

-continued

| | | | |
|---|---|---|---|
| f) | CFRSC | 48–52 | (SEQ ID NO: 23) |
| g) | CGCELVDALQFVC | 6–18 | (SEQ ID NO: 18) |
| | CCFRSCDLRRLEMYC | 47–61 | (SEQ ID NO: 20) |

2. Using extra Cys.

| | | | |
|---|---|---|---|
| h) | CGPETLC | C + 1–6 | (SEQ ID NO: 26) |
| i) | CGYGSSSRRCPQTGIVDEC | C + 30–47 | (SEQ ID NO: 27) |
| j) | CGDRGFYFNKPTC | 21–31 + C | (SEQ ID NO: 28) |
| k) | CCPLKPAKSAC | 61–70 + C | (SEQ ID NO: 29) |
| l) | CDLRRLEMY*APLKPAKSAC[3] | 52–70 + C | (SEQ ID NO: 30) |

IGF II
(SEQ ID NO: 31)
AYRPSETLCGGELVDTLQFVCGDRGFYFSRPASRVSRRSR
GIVEECCFRSCDLALLETYCATPAKSE

LOOP PEPTIDES PROPOSED[4]:

1. Using Cys present in IGF II.

| | | | |
|---|---|---|---|
| a) | CGGELVDTLQFVC | 9–21[5] | (SEQ ID NO: 32) |
| b) | CDLCLLETYC | 51–60 | (SEQ ID NO: 33) |
| c) | CCFRSCDLALLETYC | 46–60 | (SEQ ID NO: 34) |
| d) | CDLCLLETYCATPAKSE | 51–67 | (SEQ ID NO: 35) |
| e) | CCFRSC | 46–51 | (SEQ ID NO: 22) |
| f) | CFRSC | 47–51 | (SEQ ID NO: 23) |
| g) | CGGELVDTLQFVC | 9–21 | (SEQ ID NO: 32) |
| | CCFRSCDLCLLETYC | 46–60 | (SEQ ID NO: 39) |

2. Using extra Cys.

| | | | |
|---|---|---|---|
| h) | CCYRPSETLC | C + 1–9 | (SEQ ID NO: 40) |
| i) | CRPCSRVSRRSRGIVEEC | C + 30–46 | (SEQ ID NO: 41) |
| j) | CGDRGFYFSRPC | 21–31 + C | (SEQ ID NO: 42) |
| k) | CCTPAKSEC | 60–67 + C | (SEQ ID NO: 43) |
| l) | CDLCLLET*ATPAKSEC | 51–67 + C | (SEQ ID NO: 44) |

[2]Numbers refer to position of amino acids in corresponding naturally occurring IGF-I.
[3]*denotes deletion of an amino acid from the corresponding position of naturally occurring IGF-I or IGF-II.
[4]Some of the following peptides contain an Ala ---> Cys substitution.
[5]Numbers refer to position of amino acids in corresponding naturally occurring IGF-II.

Retro-inverso Peptides

A retro-isomer of a peptide is defined by a reversal of the direction of the peptide bond while maintaining the side-chain topochemistry. In retro-inverso peptides, D-amino acids are substituted for L-amino acids to retain the overall conformation for biological response and receptor binding similar to the native peptides (Hayward et al., Peptides 1974: Proc. 13th Eur. Peptide Symp., ed. Y. Wolman, pp. 287–297; Goodman et al., Acc. Chem. Res. 12:1–7 (1979)). It has been shown that the retro-inverso peptides introduced well defined conformational constraints and showed limited biodegradation by endopeptidases.

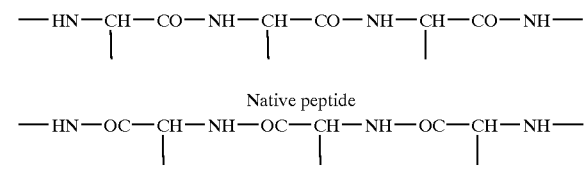

The reversal of the amino- and carboxyl termini in the retro D-peptides reduces the activity in cases where the terminal group was involved in activity. Modifications may be made at the carboxy- terminus by introducing a 2-alkylmalonate derivative and a 2-alkyl substituted geminal diamine at the amino- terminus. These groups may also be used as bridging residues when a partial or single amide modified retro-inverso segment is incorporated in a native sequence. Partial and selected single amide modified retro peptides may be used to modify the biological activity. Examples of different retro-inverso peptides are depicted here in a general sequence.

gAA---AA---AA---AA---AA---mAA

End to end modification gAA---AA---AA---mAA----AA---AA

Partial modification gAA---mAA---AA---AA---AA---AA

Single amide modification gAA=2-substituted geminal diamine amino acid surrogate
mAA=2-alkyl malonate amino acid surrogate AA=L-, D- or unusual amino acid based on the design Retro-inverso peptides are synthesized both by the solution phase segment condensation method and the solid phase method. A general procedure for preparing a geminal diamino and malonyl derivative of alanine is given below.

Synthesis of gAla:

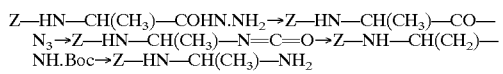

Synthesis of mAla:

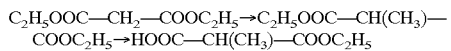

Proposed sequence: the retro-inverso peptides of the following fragments of IGF-I and IGF-II can be made following generally known peptide procedures. Numbers denote the corresponding amino acid positions of full-length IGF-I (SEQ ID NO:17), or of full-length IGF-II (SEQ ID NO:31), respectively.

IGF-I:

| | | | | | |
|---|---|---|---|---|---|
| GPETL | CGAEL | VDALQ | FVCGD | RGFYF | 1–25 |
| | AEL | VDALQ | FVCGD | RGFYF | 8–25 |
| GPETL | CGAEL | VDALQ | | | 1–15 |
| GPETL | CGAEL | | | | 1–10 |
| | | VDALQ | FVCGD | RGFYF | 1–25 |
| | | | FVCGD | RGFYF | 16–25 |
| RGFYF | NKPTG | YGSSS | RRAPQ | TGIVD | 21–45 |
| | | | RRAPQ | TGIVD | 36–45 |
| | | YGSSS | RRAPQ | TGIVD | 31–45 |
| | NKPTG | YGSSS | RRAPQ | TGIVD | 26–45 |
| | NKPTG | YGSSS | RRAPQ | | 26–40 |
| RGFYF | NKPTG | YGSSS | | | 21–35 |
| | SCDLR | RLEMY | CAPLK | PAKSA | 51–70 |
| | | RLEMY | CAPLK | PAKSA | 56–70 |
| | | | CAPLK | PAKSA | 61–70 |
| | SCDLR | RLEMY | CAPLK | | 51–65 |
| | SCDLR | RLEMY | | | 51–60 |
| | | RLEMY | CAPLK | | 56–65 |

IGF-II:

| | | | | | |
|---|---|---|---|---|---|
| VCGDR | GFYFS | RPSSR | INRRS | RGIV | 20–44 |
| | GFYFS | RPSSR | INRRS | RGIV | 26–44 |
| | | RPSSR | INRRS | RGIV | 31–44 |
| | GFYFS | RPSSR | INRRS | | 26–40 |
| VCGDR | GFYFS | RPSSR | | | 20–35 |
| CFRSC | DLALL | ETYCA | TPAKS | E | 47–67 |
| | LALL | ETYCA | TPAKS | E | 53–67 |
| | | TYCA | TPAKS | E | 58–67 |
| CFRSC | DLALL | ETYCA | | | 47–61 |
| | DLALL | ETYCA | | | 52–61 |

TABLE 3

| Sequence | Resin used | Purification method* (RT) | Wt. of pure peptide (mg) | SEQ ID NO |
|---|---|---|---|---|
| TYCAT PAK | Fmoc-Lys(Boc)-resin (1.0 g, 0.63 meq/g) | I (13.8 min) | 35.9 | 51 |
| LETYC ATP | Fmoc-Pro-resin (0.5 g, 0.36 meq/g) | I (20.7 min) | 6.1 | 52 |
| CATPA KSE | p-alkoxybenzylalcohol (1.0 g, 0.97 meq/g) | II (22.8 min) | 11.6 | 53 |
| TdYCAP AKSE | Fmoc-CAPAKSE-resin (0.2 g, 0.97 meq/g) | III (13.3 min) | 9.7 | 50 |
| YCAPA KSE | Fmoc-CAPAKSE-resin (0.2 g, 0.97 meq/g) | IV (13.4 min) | 14.3 | 54 |
| YCAPA | p-alkoxybenzylalcohol (1.0 g, 0.97 meq/g) | V (9.7 min) | 16.0 | 55 |
| TYCAP A | Fmoc-YCAPA-resin (0.3 g, 0.97 meq/g) | VI (16.6 min) | 25.0 | 56 |
| CAPAK SE | p-alkoxybenzylalcohol (0.4 g, 0.97 meq/g) | IV (9.1 min) | 16.2 | 24 |
| TY(I$_2$)CAP AKSE | Fmoc-APAKSE-resin (0.31 g, 0.97 meq/g) | VII (13.4 min) | 17.9 | 25 |
| EALLE TYCAT PAKSE | Fmoc-Glu(t-Bu)-resin (0.5 g, 0.36 meq/g) | VIII (12.7 min) | 10.8 | 36 |
| ALLEK YCAKP AKSE | Fmoc-Glu(t-Bu)-resin (0.5 g, 0.36 meq/g) | IX (14.3 min) | 35.0 | 37 |
| APSTC EYKA | p-alkoxybenzylalcohol (0.5 g, 0.97 meq/g) | III | 9.9 | 38 |

*Purification methods by HPLC:
RT = Retention time
Solvent A = water with 0.1% TFA** and B = acetonitrile with 0.1% TFA
Flow rate = 9.5 mL/min.(Waters) and 3.5 mL/min.(Vydac)
I. 0–40% of B in 40 min. Column: Waters C8
II. 0–10% of B in 40 min. Column: Waters C8
III. 5–15% of B in 15 min. Column: Vydac C8
IV. 0–10% of B in 10 min. Column: Vydac C8
V. 5–60% of B in 40 min. Column: Vydac C18
VI. 5–60% of B in 60 min. Column: Waters C18
VII. 5–40% of B in 25 min. Column: Vydac C18
VIII. 10–25% of B in 40 min. Column: Waters C8
IX. 10–30% of B in 40 min. Column: Vydac C8
**TFA = trifluoroacetic acid
(I) = iodination

TABLE 4

| Sequence | Amino acid analysis Theory (Found)* | Molecular mass Calculated (Found) | SEQ ID NO: |
|---|---|---|---|
| TYCATPAK | Thr 2 (1.96); Ala 2 (2.28) Pro 1 (0.98); Tyr 1 (1.00) Lys 1 (1.04); Cys 1 | 854.14 (854) | 51 |
| LETYCATP | Glx 1 (1.02); Thr 2 (1.74) Ala 1 (1.23); Pro 1 (1.10) Tyr 1 (1.00); Leu 1 (1.14) Cys 1 | 897.16 (898) | 52 |
| CATPAKSE | Glx 1 (1.05); Ser 1 (0.99) Thr 1 (1.15); Ala 2 (2.09) Pro 1 (0.99); Lys 1 (0.87) Cys 1 | 805.00 (806) | 53 |
| TdYCAPAKSE | Glu 1 (0.86); Ser 1 (0.90) Thr 1 (1.30); Ala 2 (2.04) Pro 1 (0.86); Tyr 1 (1.00) Lys 1 (1.07) | 969.00 (970) | 50 |
| YCAPAKSE | Glu 1 (0.94); Ser 1 (0.86) Ala 2 (1.96); Pro 1 (0.93) Tyr 1 (0.93); Lys 1 (1.30) Cys 1 | 867.99 (868) | 54 |
| YCAPA | Ala 2 (2.09); Pro 1 (0.96) Tyr 1 (0.98); Cys 1 | 523.00 (524) | 55 |
| TYCAPA | Thr 1 (1.18); Ala 2 (2.00) Pro 1 (0.95); Tyr 1 (0.96) Cys | 624.00 (625) | 56 |
| CAPAKSE | Glu 1 (0.92); Ser 1 (0.88) Ala 2 (2.22); Pro 1 (1.08) Lys 1 (1.09); Cys 1 | 704.00 (705) | 24 |
| TY(L$_2$) CAPAKSE | Glx 1 (0.75); Ser 1 (0.99) Thr 1 (1.02); Ala 2 (2.00) Pro 1 (1.02); Tyr 1 (0.99) Lys 1 (1.28); Cys 1 | 1220.00 (1221) | 25 |
| EALLETYCA-TPAKSE | Glx 3 (3.04); Ser 1 (0.91) Thr 2 (1.84); Ala 3 (3.03) Pro 1 (0.92); Tyr 1 (0.98) Leu 2 (2.18); Lys 1 (1.19) Cys 1 | 1625.00 (1626) | 36 |
| ALLEKYCA-KPAKSE | Glx 2 (2.00); Ser 1 (0.81) Ala 3 (2.96); Pro 1 (0.99) Tyr 1 (0.95); Leu 2 (2.00) Lys 3 (3.07); Cys 1 | 1551.06 (1552) | 37 |
| APSTCEYKA | Glx 1 (1.02); Ser 1 (0.97) Thr 1 (0.89); Ala 2 (2.21) Pro 1 (0.89); Tyr 1 (0.94) Lys 1 (1.14); Cys 1 | 969.00 (969) | 38 |

*Cysteine was not determined

Uses of the Peptides

As described more fully below, the present invention provides novel uses of IGF-I and IGF-II and their functional derivatives, and of IGF-I, IGF-II, and their functional derivatives in combination with NGF and its functional derivatives, as agents for the treatment of diseases or disturbances characterized by an increased risk of cell death, including in particular, neuronal cell death. The bioactivity of each polypeptide (or combination of polypeptides) of the invention may be conveniently assayed by a brain ornithine decarboxylase assay, a spinal cord choline acetyl transferase assay, a cultured septal cell assay, or a cultured cortical cell assay, all of which are described in detail below. Alternatively, the polypeptides may first be screened by a receptor-growth factor displacement assay, e.g., the receptor-IGF-I displacement assay described below, which measures the polypeptide's ability to displace labelled IGF-I bound to receptors in homogenized brain tissue. This assay has been demonstrated to correlate with the polypeptide's bioactivity as measured by the two enzymatic assays. As described in the examples below, these assays disclose previously unknown bioactivity of IGF-I, IGF-II, IGF-III and some functional derivatives of these molecules both alone, and in combination with NGF or functional derivatives of NGF. Thus, the peptides of this invention should be useful for administration to humans or other mammals who suffer from neurological diseases or disturbances characterized by increased risk of neuronal cell death, as described above. These neurological diseases or disturbances include but are not limited to: Alzheimer's disease, Parkinson's disease, amyotrophic lateral sclerosis, stroke, and concussive or penetrating injuries of the brain or spinal cord.

The formulations of this invention are useful for parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol, scarification, and also for oral, buccal, rectal or vaginal administration. The compositions can be formulated for parenteral administration to humans or other mammals in therapeutically effective amounts (e.g., amounts which eliminate or reduce the patient's pathological condition) to provide therapy for the neurological diseases described above.

The compounds provided herein can be formulated into pharmaceutical compositions by admixture with pharmaceutically acceptable nontoxic excipients and carriers. As noted above, such compositions may be prepared for use as parenteral administration, particularly in the form of liquid solutions or suspensions; for oral administration, particularly in the form of tablets or capsules; or intranasally, particularly in the form of powders, nasal drops, or aerosols. The compositions may conveniently be administered in unit dosage form and may be prepared by any of the methods well known in the pharmaceutical art, for example, as described in *Remington's Pharmaceutical Sciences*. Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the peptides. Other potentially useful parenteral delivery systems for these peptides include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

The materials of this invention can be employed as the sole active agent in a pharmaceutical or can be used in combination with other active ingredients, e.g., other growth factors which could facilitate neuronal survival in neurological diseases, or peptidase or protease inhibitors.

The concentration of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 μg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the neurological disease, the overall health status of the particular patient, the relative biological efficacy of the compound selected, the formulation of the compound excipients, and its route of administration.

The present invention will be further illustrated by the following examples. These examples are not to be construed as limiting the scope of the invention, which is to be determined solely by the appended claims.

EXAMPLE 1

Recombinant human IGF-I, IGF-II, and IGF-III, as well as several chemically synthesized peptides consisting of partial sequences of IGF-I or IGF-II, were obtained from commercial sources as indicated in Table 1. $^{125}$I-labeled [Threonine$^{59}$]IGF-I was obtained from Amersham (Arlington Heights, Ill.). Other peptides consisting of partial sequences of IGF-I or IGF-II were chemically synthesized using Fmoc chemistry on a Milligen Biosearch Model 9600 Peptide Synthesizer, and purified on Hewlett-Packard Models 1050 and 1090M HPLCs according to the method of Hudson, J. Org. Chem. 53:617–624 (1988). Fmoc amino acids, BOP (Castro's reagent), and resins were purchased from Biosearch (San Raphael, Calif. 94901) and Bachem Bioscience, Inc. (Philadelphia, Pa. 19104). Solvents were purchased from Burdick and Jackson (Muskegon, Mich. 49442). Other reagents were purchased from Sigma Chemical Co. (St. Louis, Mo. 63178).

Brain tissue containing the cerebral cortex and cerebellum was dissected from adult Sprague-Dawley rats (Hilltop Lab Animals, Inc. Scottsdale, Pa.) and homogenized at low power for 5 minutes in a Brinkmann Polytron homogenizer (Westbury, N.Y.) containing 50 volumes of ice-cold buffer consisting of 10 mM HEPES, 0.5% BSA, 0.0125% NEM, 0.025% bacitracin, and 100 KIU/ml aprotinin, pH 7.6 (Bohannon et al., Endocrinology 119:943–945 (1986). Following homogenization, the tissue was collected after centrifugation at 7800× g for 20 minutes and resuspended in 10 volumes of assay buffer. Tissue (50 μl), 100 μl $^{125}$I-[Threonine$^{59}$]IGF-I (20 pM), and 50 μl of buffer or peptides of varying concentration were added to 96-well plates and incubated on ice for 3 hours. After the incubation period, the tissue was collected on Whatman GF/C filters that had been pre-soaked in 0.01% polyethylenimine and washed four times with ice-cold assay buffer using a Brandel cell harvester (Gaithersburg, Md.). The filters were removed and the bound $^{125}$I-[Threonine$^{59}$]IGF-I was measured using a Beckman Model 5500B Gamma Counter.

Table 5 summarizes the results of the $^{125}$I-[Threonine$^{59}$] IGF-I displacement assay utilizing native IGFs and IGF fragments. The results demonstrate that, while IGF-I and IGF-III are potent displacers of $^{125}$I-[Threonine$^{59}$]IGF-I, IGF-II is essentially inactive, indicating that the assay is selective for the identification of IGF-I-like molecules. In this assay, IGF-I(24–41) alone or in combination with IGF-II(54–67) were active in displacing $^{125}$I-[Threonine$^{59}$]IGF-I. IGF-II(54–67) alone, and several other fragments listed in Table 5 were not significantly effective displacers of $^{125}$I-[Threonine$^{59}$]IGF-I.

EXAMPLE 2

Brains were removed intact from adult Sprague-Dawley rats, frozen on powdered dry ice, and cut into 20 μm sections (at the level of the cerebellum and brain stem) which were

TABLE 5

IGF-I RECEPTOR COMPETITION ASSAY SUMMARY

| PEPTIDE (CONC.) | | PERCENT MAX. BOUND (SD) | |
|---|---|---|---|
| IGF-I | (10 pM) | 100 | (1.1) |
| IGF-I | (40 nM) | 9.6 | (0.7) |
| IGF-II | (40 nM) | 92.1 | (0.7) |
| IGF-III | (40 nM) | 17.6 | (2.6) |
| IGF-I(24–41) | (100 μM) | 44 | (7) |
| IGF-I(24–41) | (50 μM) | 99 | (6) |
| IGF-I(24–41) | (50 μM) + | 49 | (11) |
| IGF-II(54–67) | (50 μM) | | |
| IGF-II(54–67) | (100 μM) | 94 | (6) |
| IGF-I(62–70) | (100 μM) | 83 | (20) |
| IGF-I(30–41) | (100 μM) | 94 | (1.4) |
| IGF-II(62–67) | (100 μM) | 83 | (21) |
| IGF-II(33–40) | (1 mM) | 92 | (1.8) | thaw-mounted onto gelatin-coated glass microscope slides (Herkenham and Pert, J. Neurosci. 2:1129–1149 (1982)). Using a modification of the method of Bohannon et al. (1986), the tissue sections were covered with 250 μl of HEPES assay buffer (see Example 1) containing 0.01 nM $^{125}$I-[Threonine$^{59}$]IGF-I alone or in combination with unlabeled IGF-I, IGF-II, or synthetic peptide fragments thereof. The sections were incubated at 4° C. for 24 hours and then rinsed in three 1-minute changes (200 ml each) of ice-cold HEPES assay buffer. The tissue sections were then wiped off the slides with filter paper, and the tissue-bound radioactivity was measured in a Beckman Model 5500B Gamma Counter.

In this assay, in contrast to the assay described in Example 1, $^{125}$I-[Threonine$^{59}$]IGF-I binding was potently displaced by both IGF-I and IGF-II, indicating the utility of this assay for detecting potentially active derivatives of both of these molecules (Table 6). $^{125}$I-[Threonine$^{59}$]IGF-I binding was displaced by IGF-II(33–40), but not by IGF-II(54–67).

EXAMPLE 3

The activity of IGF-I, IGF-II, or synthetic peptide derivatives of these molecules was assayed on dissociated cultures of 14-day embryonic rat spinal cord neurons. The spinal cord neurons were obtained from trypsin-dissociated spinal cords, plated, incubated with peptides, and subsequently (48 hr later) assayed for choline acetyltransferase activity as described by McManaman et al., Dev. Biol. 125:311–320 (1988).

In this assay, IGF-I was found to produce a substantial, dose-dependent increase in choline acetyltransferase activity (FIG. 1), suggesting that IGF-I

TABLE 6

Figure 2:
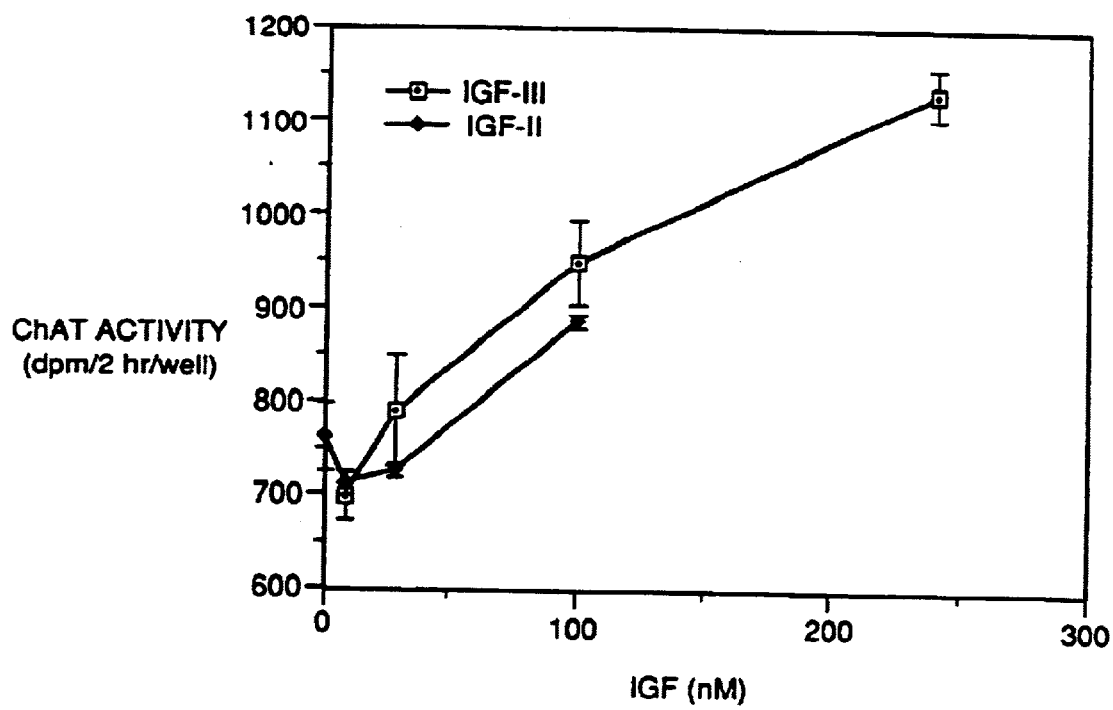
FIG. 2 is a graph showing the effect of IGF-II and IGF-III on the survival of cholinergic neurons in rat spinal cord cultures.
Figure 3:
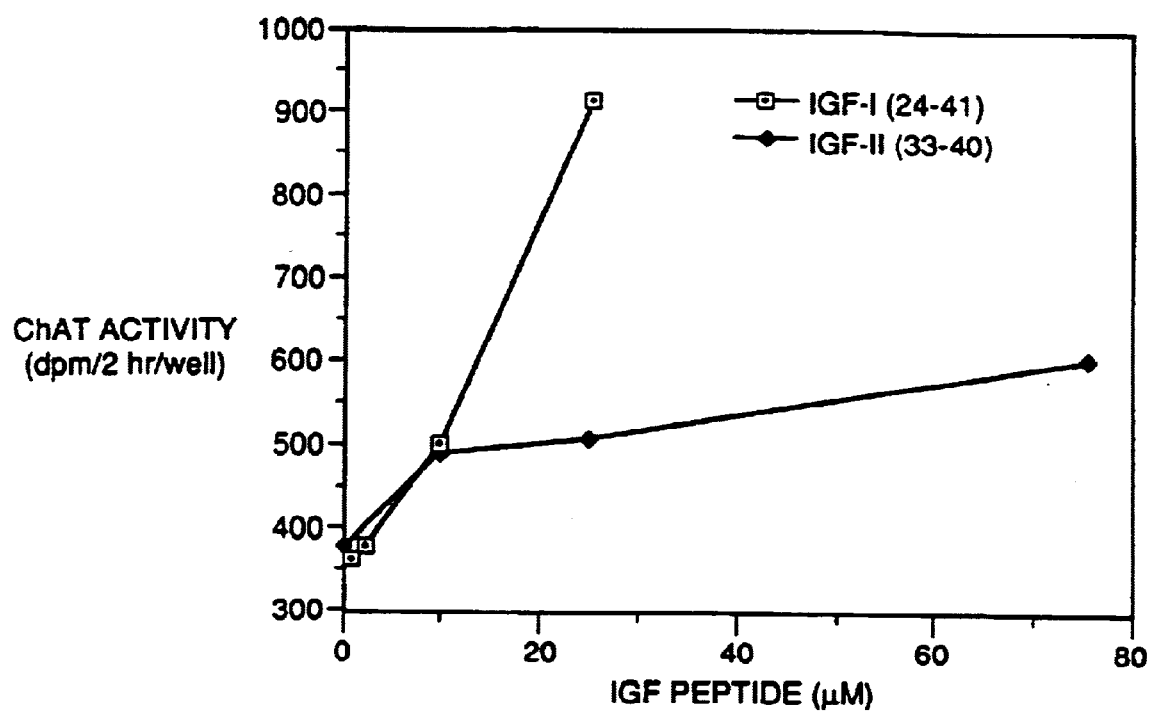
FIG. 3 is a graph illustrating the effect of certain synthetic peptide fragments of IGF-I and IGF-II on the survival of cholinergic neurons in rat spinal cord cultures.

| PEPTIDE | PERCENT MAX. BOUND |
|---|---|
| IGF-I (4 pM) | 91 |
| IGF-I (400 pM) | 30 |
| IGF-II (200 nM) | 50 |
| IGF-II (400 nM) | 23 |
| IGF-II (33–40) (1 mM) | 76 |
| IGF-II (33–40) (.10 mM) | 82 |
| IGF-II (54–67) (.25 mM) | 167 |
| IGF-II (54–67) (.025 mM) | 132 | can dramatically enhance the cholinergic activity and/or survival of spinal cord cholinergic neurons. Furthermore, IGF-II and IGF-III were found to be active in the spinal cord assay (FIG. 2). In addition, IGF-I(24–41) and IGF-II(33–40) were also found to produce a dose-dependent increase in choline acetyltransferase activity, indicating that each peptide is an active IGF functional derivative (FIG. 3).

EXAMPLE 4

The in vivo activity of IGF-I, IGF-II or synthetic peptide derivatives of these molecules was tested using a biochemical marker for CNS neurotrophic activity, the induction of brain ornithine decarboxylase. The induction (i.e. increased activity) of ornithine decarboxylase has been reported to be a general marker for the actions of a variety of trophic factors. (Schwartz et al., Dev. Brain Res. 1:403–413 (1981); Kanje et al., Brain Res. 381:24–28 (1986); Russell et al., Life Sci. 19:1297–1306 (1976); MacDonnell et al. Proc. Natl. Acad. Sci. USA 74, 4681–4684 (1977); Rinehart et al. Proc. Natl. Acad. Sci. USA 82, 4365–4368 (1985)).

Sprague-Dawley rats, 4 days old, were injected intracerebrally (in the area of the lateral ventricle) with 5 µl of 0.1 M phosphate-buffered saline (PBS) containing IGF-I, IGF-II or a synthetic peptide derivative (1.25–2.5 µg dose, with 6 animals per treatment group). After 6 hours, the brains were removed, and ornithine decarboxylase was assayed essentially as described by Lewis et al., Proc. Natl. Acad. Sci. USA 75:1021–1023 (1978).

Figure 4:
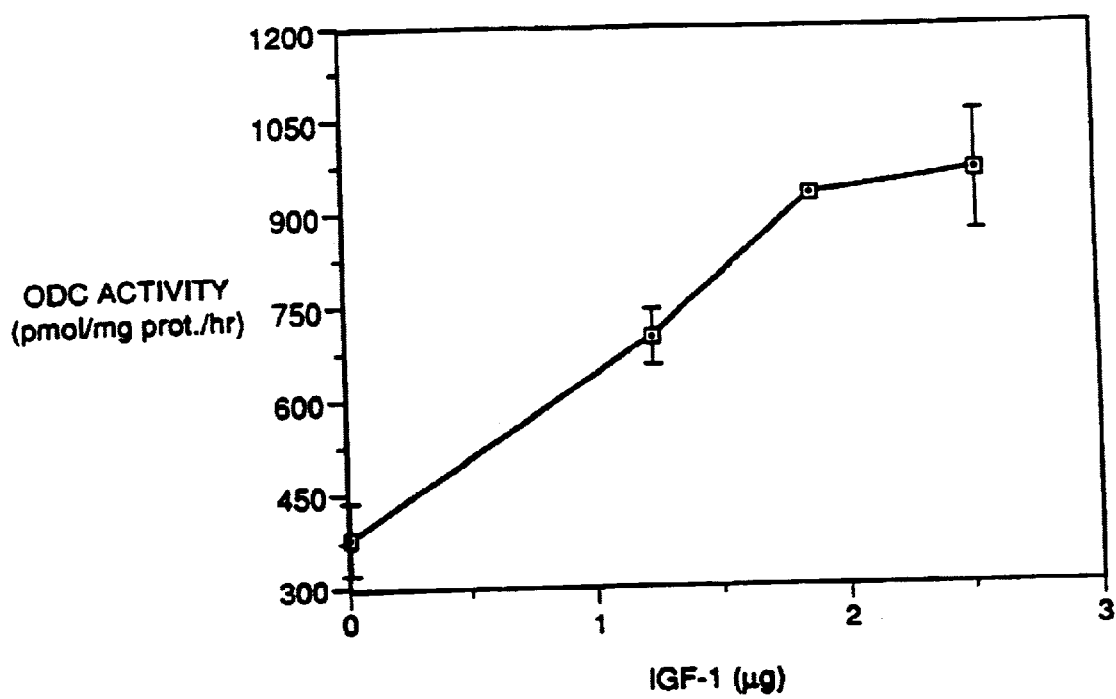
FIG. 4 is a graph depicting the effect on brain ornithine decarboxylase activity of increasing doses of IGF-I injected into the brains of immature rats.
Figure 5:
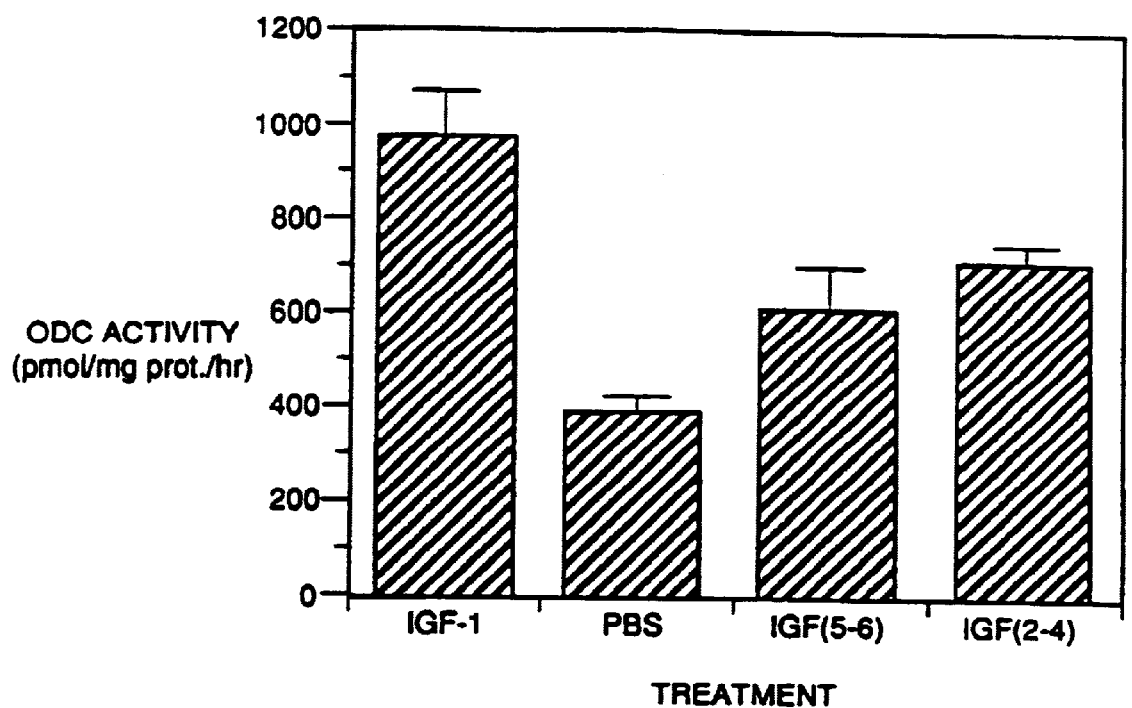
FIG. 5 is a graph showing the effect on brain ornithine decarboxylase activity of injection of IGF-I or synthetic peptide fragments of IGFs into the brains of immature rats.

Administration of IGF-I produced a dose-dependent increase in brain ornithine decarboxylase activity (FIG. 4). In addition, both IGF-I(24–41) and IGF-II(54–67) increased brain ornithine decarboxylase activity (FIG. 5; these peptides are referred to in FIG. 5 as IGF-I (2–4) and IGF-I(5–6), respectively).

EXAMPLE 5

Figure 6:
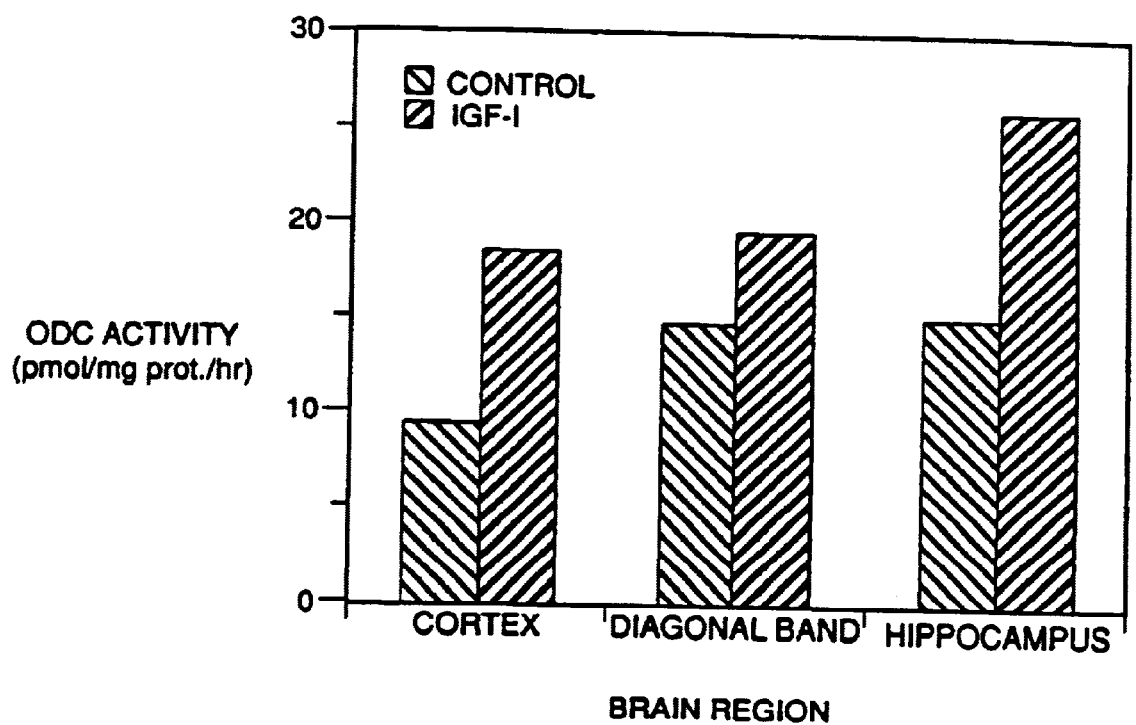
FIG. 6 is a graph depicting the effect on brain ornithine decarboxylase activity of injection of IGF-I into the brains of mature rats.

To determine whether the induction of brain ornithine decarboxylase by IGF-I was limited to developing animals, IGF-I was also injected intraventricularly into the lateral ventricles of adult Sprague-Dawley rats. After 6 hours, the brains were removed, dissected into several regions (cerebral cortex, medial septum, and hippocampus), and then assayed for ornithine decarboxylase activity as described in Example 4. As shown in FIG. 6, IGF-I stimulated ornithine decarboxylase activity in all brain regions assayed. This result indicates that IGF-related molecules have potential utility in widespread regions of the brain.

EXAMPLE 6

Figure 7:
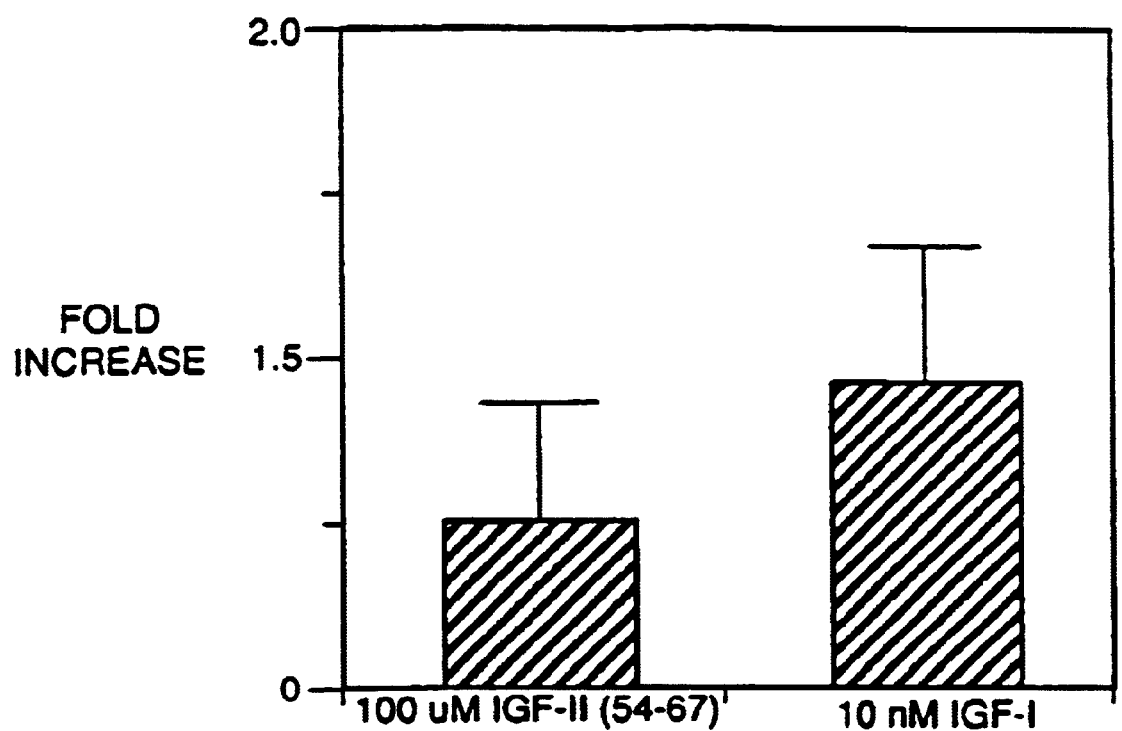
FIG. 7 is a graph illustrating the effect of an IGF-II derivative and of IGF-I on survival of cortical cells, as assessed by leucine incorporation.
Figure 8:
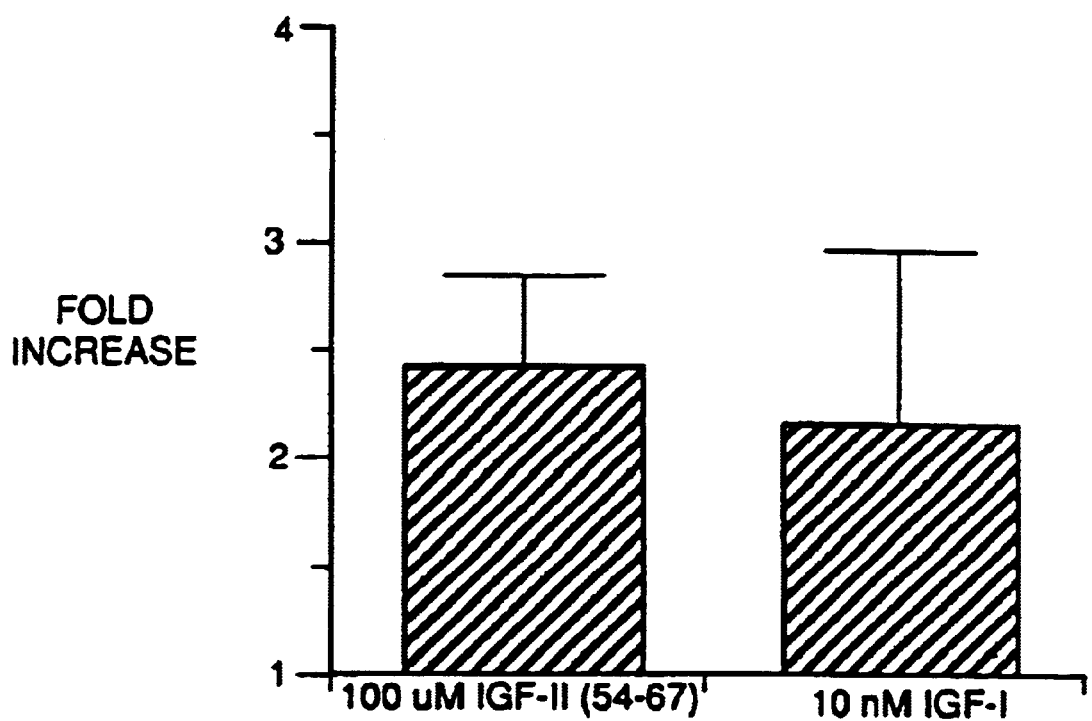
FIG. 8 is a graph illustrating the effect of an IGF-II derivative and IGF-I on the survival of cortical neurons, as assessed by morphological characteristics.

The ability of IGF-I and a synthetic derivative of IGF-II (IGF-II(54–67)) to increase the incorporation of [$^3$H]-leucine and to promote the survival of neurite bearing cells was examined in cultured rat cortical cells (the numbers "54–67" in IGF-II indicate the fragment includes amino acid residues 54–67 of native IGF-II). IGF-II(54–67), like IGF-I, increased [$^3$H]-leucine incorporation in low density 24 hour mixed cortical cultures, as shown in FIG. 7. IGF-II(54–67) also displayed IGF-I-like survival-promoting activity in that it increased the survival of cortical neurons (as determined by the presence of neurite bearing cells), as shown in FIG. 8.

Measurements were performed, using standard techniques known to those skilled in the art, on dissociated cortical cells obtained from day 18–19 embryonic rats. Cells were seeded at $1.5 \times 10^4/cm^2$ on poly-1-ornithine-laminin coated plastic tissue culture cells in serum-free N2 medium (Bottenstein et al. Proc. Natl. Acad. Sci. U.S.A. 76: 514–517 (1978)). [$^3$H]-leucine was added to cells at plating for the incorporation assay. Cultures were terminated 24 hours after plating and measured for either [$^3$H]-leucine incorporation or for the number of neuritic cells by microscopic examination.

EXAMPLE 7

Figure 9:
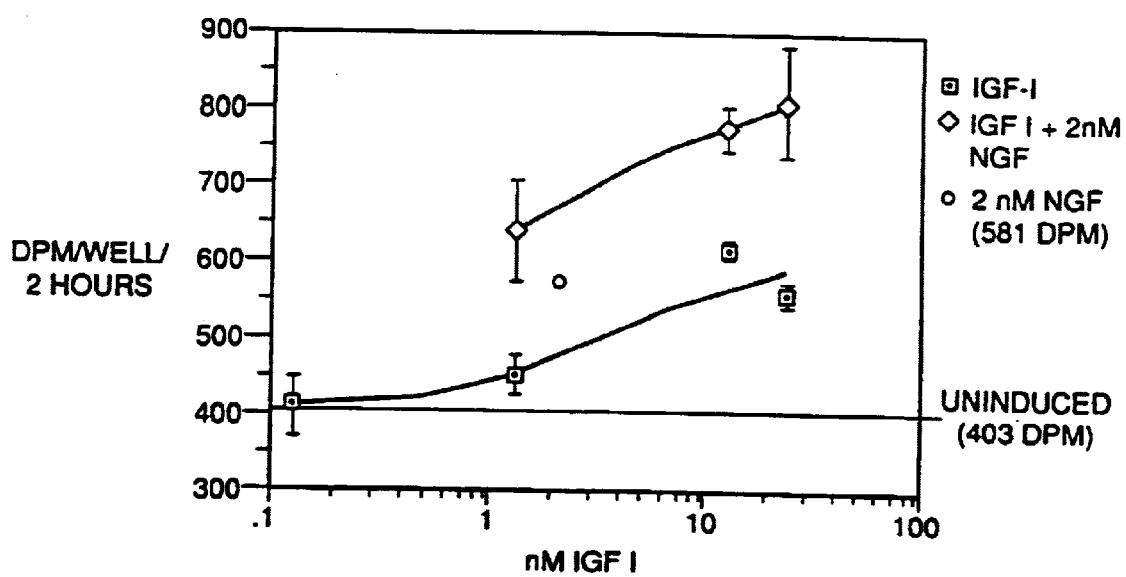
FIG. 9 is a graph illustrating the additive effect of NGF (at saturating concentration) and IGF-I on ChAT activity in cultured rat septal cells.
Figure 10:
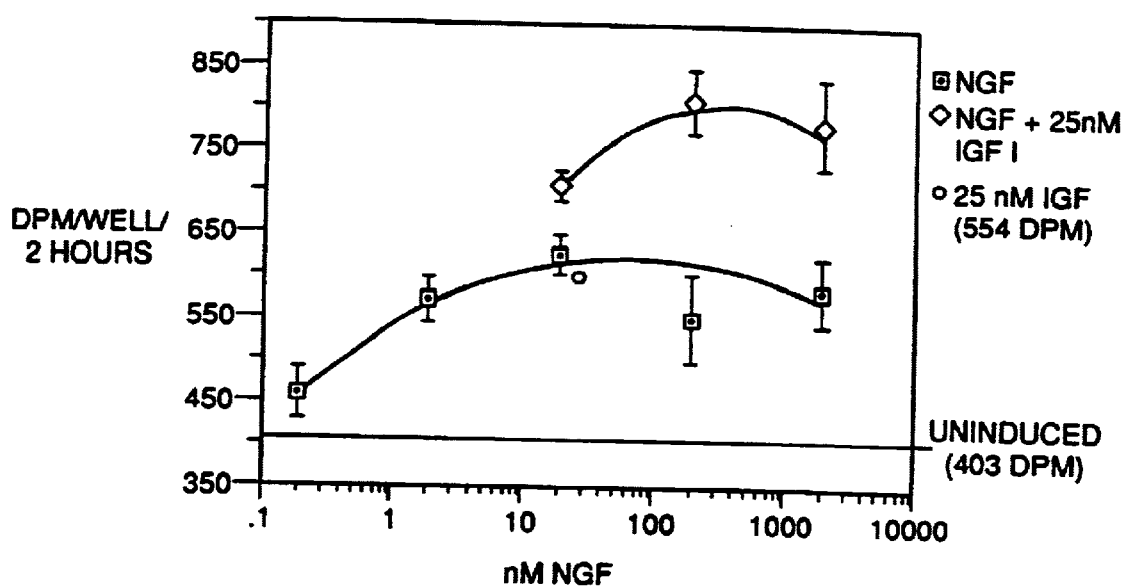
FIG. 10 is a graph illustrating the additive effect of NCF and IGF (at saturating concentration) on ChAT activity in cultured rat special cells.

The effect of simultaneous administration of IGF-I and NGF on ChAT activity was assayed in cultured septal neurons. ChAT is the initial enzyme in the synthesis of the neurotransmitter, acetylcholine, and is a specific biochemical marker for cholinergic neurons. Assay of this enzyme may be used as an indication of the effects of IGF (and other factors) on the survival of cholinergic neurons and/or regulation of this enzyme. An additive increase in ChAT activity was seen with saturating concentrations of NGF combined with saturating or sub-maximal concentrations of IGF-I, as shown in FIG. 9. In FIG. 9 open squares represent IGF-I, diamonds indicate IGF-I+2 nM NGF, open circles indicate 2 nM NGF, and the horizontal line at 403 DPM represents uninduced cells. A similar additive effect was seen when saturating concentrations of IGF-I were combined with saturating or sub-maximal concentrations of NGF, as shown in FIG. 10. In FIG. 10 open squares indicate NGF, diamonds indicate NGF+25 nM IGF-I, open circles represent 25 nM IGF-I, and the horizontal line at 554 DPM represents uninduced cells. The percent increases in ChAT activity over control uninduced cells are summarized in Table 7.

Cultured rat septal cell experiments were performed generally as described in Hartikku and Hefti, J. Neuroscience, 8:2967–2985 (1985), Hayashi and Patel, Dev. Brain Res., 36:109–120 (1987), and as follows.

TABLE 7

ADDITIVE EFFECTS OF NGF AND IGF-I ON
CHAT ACTIVITY IN CULTURED RATE SEPTAL CELLS

| Growth Factor | Concentration nM | % increase over control |
|---|---|---|
| NGF | 2.0 | 44 |
| IGF-I | 1.3 | 20 |
|  | 12.5 | 50 |
|  | 25.0 | 37 |
| 2 nM NGF + IGF-I | 1.3 | 58 |
|  | 12.5 | 93 |
|  | 25.0 | 100 |
| IGF-I |  | 44 |
| NGF | 0.02 | 56 |
|  | 0.2 | 36 |
|  | 2.0 | 44 |
| 25 nM IGF-I + NGF | 0.02 | 75 |
|  | 0.2 | 100 |
|  | 2.0 | 94 |

Dissociated cell cultures of the septal region of day 17 embryonic rats were prepared by standard techniques known to those skilled in the art, using enzymatic (Dispase, Collaborative Research) dissociation of tissue. Cells were seeded (plated) at $6 \times 10^5$ cells/cm$^2$ in poly-1-ornithine-laminin coated plastic tissue culture wells, and cultured in serum-free N2 medium (Bottenstein et al., 1978) for 5 days without feeding. Control (uninduced) cultures received no added growth factors; induced cultures received the concentrations of IGF-I and NGF indicated in FIGS. 9 and 10 at the time of plating. NGF is commercially available. ChAT was assayed by the method described in McManaman, et al. Dev. Biol. 125:311–320 (1988). AChE staining was performed according to the method of Hartikka and Hefti, J. Neuroscience 8:2967–2985 (1988).

Positive cytochemical staining for the enzyme acetylcholinesterase (AChE) has been shown to be a reliable marker for choline acetyltransferase positive neurons in rat septal cell cultures (Hartikka and Hefti, J. Neuroscience 8:2967–2985 (1988).

EXAMPLE 8

Figure 11:
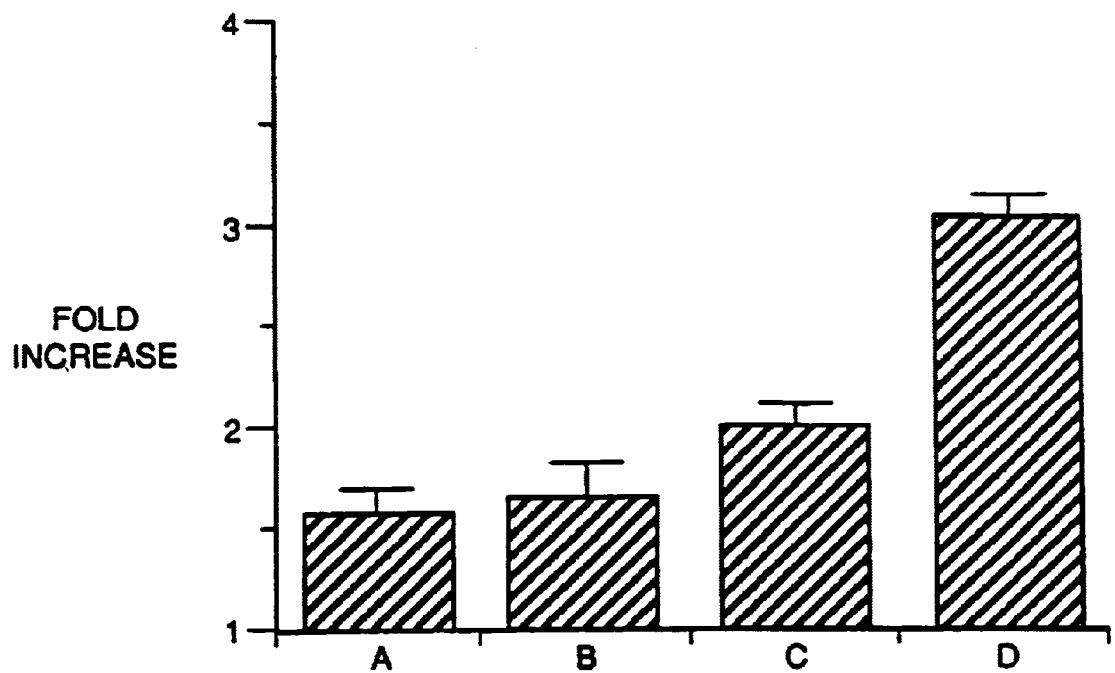
FIG. 11 is a graph illustrating the effect of timed addition of NGF and IGF-I on ChAT activity in cultured septal cells.

The sequence in which NGF and IGF-I are added to the culture medium has a significant effect on the magnitude of the increase of ChAT activity in cultured rat septal cells, as shown in FIG. 11. In FIG. 11, A represents 2 nM IGF, B represents 25 nM IGF-I, C represents IGF-I+NGF, both added 5 days before assay, and D IGF-I added at the beginning of the experiment+NGF added on day 3 of the experiment, with assay on day 5 of the experiment. When added separately, NGF or IGF-I increased ChAT activity 50 to 60% in a 5 day old culture. When NGF and IGF-I were present together for the entire 5 days the NGF and IGF-I effects on ChAT activity were additive (a 100% increase), as shown in FIGS. 9, 10, and 11.

When IGF-I was present from the beginning of the experiment and NGF was added on day 3, the ChAT activity on day 5 was increased by 300% over uninduced cultures, as shown in FIG. 11. Thus it has been discovered that IGF-I and NGF act in a previously unknown, complimentary manner to enhance the survival and neurotransmitter-synthesizing capacity of cholinergic neurons.

Cultured rat septal cell experiments were performed as described above.

EXAMPLE 9

Figure 12:
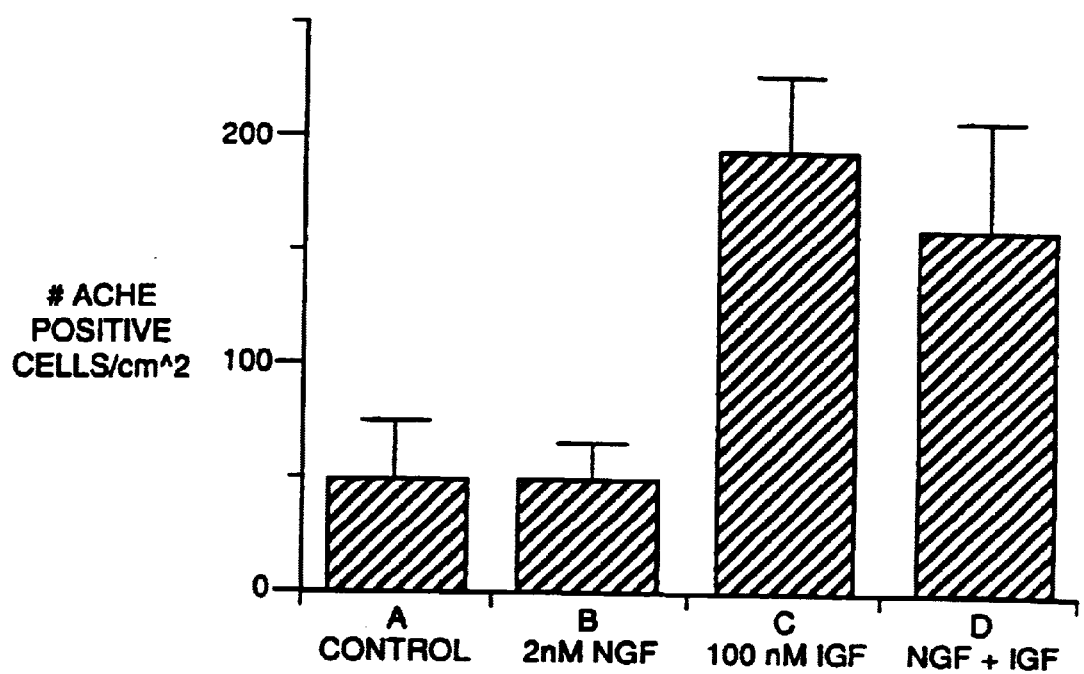
FIG. 12 is a graph illustrating the effect of NGF and IGF-I on the number of AChE positive cells in septal cultures.

We have shown that under specific culture conditions ($4 \times 10^5$ cells/cm$^2$ in the presence of medium containing 10% bovine calf serum), IGF-I increased the number of AChE positive cells by 3–4 fold over control, growth factor-free cultures, FIG. 12. In FIG. 12 A represents uninduced cells, B represents cells treated with 2 nM NGF, C represents cells treated with 100 nM IGF-I, and D represents cells treated with NGF+IGF-I. (DPM=radioactive disintegrations per minute.) NGF under the same conditions, did not affect the number of AChE positive cells. These results indicate that IGF-I has a greater effect on cholinergic cell survival (i.e. increases cholinergic survival), while NGF regulates (increases) ChAT activity in existing cholinergic neurons.

EXAMPLE 10

Cationization is a process by which free carboxyl groups of acidic amino acid residues on a polypeptide (i.e., aspartic acid and glutamic acid residues) are modified in order to increase the net positive charge on the polypeptide. The process of cationization has been used to enhance the cellular uptake of large molecules such as albumin and horseradish peroxidase into mouse fibroblast cells (Shen et al., Proc. Nat. Acad. Sci. USA 75:1872–1876 (1978)). Kumagai et al., J. Biol. Chem. 262:15214–15219 (1987), using intact microvessels from bovine brain that are reportedly a model system for measuring transport across the blood-brain barrier, showed that uptake of cationized albumin by isolated bovine brain microvessels was enhanced when compared with uptake of native albumin.

For global modification of free carboxyl groups, the polypeptide (e.g., NGF, IGF-I, IGF-II or a functional derivative) would be reacted with excess hexamethylenediamine (HMD) (15.5 g/g total protein) for 30 minutes at room temperature, followed by covalent coupling of HMD with 1-ethyl-3[-3-dimethyl-aminopropyl]carbodiimide hydrochloride (EDAC) (1.0 g/g total protein) for 3 hours at room temperature. Unreacted species may be removed by filtration using Centricon-3 MPS-1 separation devices (Amicon, Danvers, Mass.) or ion exchange chromatography. The purified polypeptide may be analyzed using isoelectric focusing to determine the amount of cationization.

If the global modification is used on a polypeptide that is a ligand which binds to a cell surface receptor, and the modification produces a molecule lacking biological activity, the cationization process may be repeated as described above except that the polypeptide would be pre-bound to an appropriate receptor prior to cationization, in order to protect the receptor-binding site on the polypeptide. This protection procedure would be carried out as follows: Tissue, e.g., brain, containing receptors for the polypeptide of interest (e.g., IGF-I) is prepared as described above in Example 1. After incubation with the polypeptide ligand for 2 hours at 4° C. to permit receptor binding, the reaction mixture is brought to room temperature, and the cationization procedure carried out using HMD and EDAC as described above. The reaction mixture is then centrifuged at 16,000 rpm at 4° C. for 30 sec in an SS-34 rotor in a Sorvall RC5B centrifuge. The supernatant is discarded and the pellet washed three times in PBS with bovine serum albumin (1 mg/ml). The pellet is resuspended in 100 mM acetic acid and incubated for 10 min at 4° C. to release the cationized polypeptide from its receptors. After centrifugation again at 16,000 rpm, the supernatant, which contains the released cationized polypeptide, is pH-neutralized with NaOH. It may then be analyzed by isoelectric focusing, by a receptor-binding assay as described in Example 1, or by any appropriate assay for biological activity.

EXAMPLE 11

An alternative to the global modification method is to couple polylysine to at least one free carboxyl group on a polypeptide (such as IGF-I, IGF-II, or a functional derivative of either) with or without receptor protection as described above in Example 10. The procedure follows the method of Shen et al., 1978. For example, polylysine, IGF-I and carbodiimide are added in a 1:1:1 ratio in water or buffer for 3 hours at room temperature. The modified protein would be separated and analyzed as described above in Example 10.

EXAMPLE 12

A third method for modifying protein carboxyl groups to enhance blood brain barrier transport is to form esters with diazomethane or N,N-dimethylformamide R acetals (DMF acetals), where R is dimethyl, diethyl, dibutyl, dibenzyl, etc. This type of modification rapidly forms esters from negatively charged carboxylic acid groups, thus increasing the overall positive charge. An additional benefit from this modification is that these added ester groups may be such that they increase the overall lipophilicity of the polypeptide and may be removed by intrinsic esterases in vivo to yield intact growth factor. The procedure for this modification, with or without receptor protection as described above in Example 10, is to react diazomethane or DMF acetals with the polypeptide in a 1:1 ratio in solution for 30 min. at room temperature, followed by purification and characterization as described above in Example 10.

EXAMPLE 13

A fourth method of cationization, with or without receptor protection as described above in Example 10, combines the advantages of polylysine cationization with the formation of cleavable esters to enhance blood-brain barrier transport, as well as to yield intact growth factor following transport. Polylysine may be made reactive by reaction with benzyloxylacetyl chloride followed by hydrogenation and mild esterification procedures (Hassner et al., Tet. Let. 46:4475–4478 (1978); Mihara et al., Int. J. Peptide Protein Res. 28:141–145 (1986)). Alternatively, DMF acetal derivatives capable of reacting with polylysine could be used to link polylysine to free carboxyl groups using ester linkages.

EXAMPLE 14

A further type of polypeptide modification is glycosylation: the introduction of glucose or similar residues by reductive amination using, for example, glucose and sodium cyanoborohydride ($NaCNBH_3$). Glycosylation of proteins has been shown to enhance the cellular uptake of these proteins and may prove useful for improving blood-brain barrier transport (Smith et al., Pharm. Res., in press). The procedure for glycosylation, with or without receptor protection as described above in Example 10, is based on the method of Schwartz et al., 1977, wherein a polypeptide such as IGF-I, IGF-II, or a functional derivative of either is combined with glucose and $NaCNBH_3$ in a molar ratio of 1:300:1600 in 200 mM phosphate buffer at pH 7 for at least 24 hr at 37° C. Unreacted entities may be removed as described in Example 10, or with lectin affinity chromatography. In previous studies using glycosylated albumin, the modified albumin was taken up by rat epididymal microvessels at a greater rate than was native albumin (Williams et al., Proc. Nat. Acad. Sci. USA 78:2393–2397 (1981)).

EXAMPLE 15

Blood-Brain Barrier Transport Model: Method of Audus et al., Ann.N.Y.Acad.Sci. 507:9–18 (1987).

Microvessel endothelial cells are isolated from the cerebral gray matter of fresh bovine brains. Brains are obtained from a local slaughter house and transported to the laboratory in ice cold minimum essential medium (MEM) with antibiotics. Under sterile conditions the large surface blood vessels and meninges are removed. The cortical gray matter is removed by aspiration, then minced into <1 mm cubes. The minced gray matter is then incubated with 0.5% dispase (BMB, Indianapolis, Ind.) for 3 hours at 37° C. in a shaking water bath. Following the 3 hour digestion, the mixture is concentrated by centrifugation (1000× g for 10 min.), then resuspended in 13% dextran and centrifuged for 10 min. at 5800× g. Supernatant fat, cell debris and myelin are discarded and the crude microvessel pellet is resuspended in 1 mg/ml collagenase/dispase and incubated in a shaking water bath for 5 hours at 37° C. After the 5-hour digestion, the microvessel suspension is applied to a pre-established 50% Percoll gradient and centrifuged for 10 min at 1000× g. The band containing purified endothelial cells (second band from the top of the gradient) is removed and washed two times with culture medium (50% MEM/50% F-12 nutrient mix). The cells are frozen (−80° C.) in medium containing 20% DMSO and 10% horse serum for later use.

After isolation, approximately $5 \times 10^5$ cells/cm² are plated on culture dishes or 5–12 @m pore size polycarbonate filters that are coated with rat collagen and fibronectin. 10–12 days after seeding the cells, cell monolayers are inspected for confluency by microscopy.

Characterization of the morphological, histochemical and biochemical properties of these cells has shown that these cells possess many of the salient features of the blood-brain barrier. These features include: tight intercellular junctions, lack of membrane fenestrations, low levels of pinocytotic activity, and the presence of gamma-glutamyl transpeptidase, alkaline phosphatase, and Factor VIII antigen activities.

The cultured cells can be used in a wide variety of experiments where a model for polarized binding or transport is required. By plating the cells in multi-well plates, receptor and non-receptor binding of both large and small molecules can be conducted. In order to conduct transendothelial cell flux measurements, the cells are grown on porous polycarbonate membrane filters (Nucleopore, Pleasanton, Calif.). Large pore size filters (5–12 μm) are used to avoid the possibility of the filter's becoming the rate-limiting barrier to molecular flux. The use of these large-pore filters does not permit cell growth under the filter and allows visual inspection of the cell monolayer.

Once the cells reach confluency, they are placed in a side-by-side diffusion cell apparatus (Crown Glass, Sommerville, N.J.). For flux measurements, the donor chamber of the diffusion cell is pulsed with a test substance, then at various times following the pulse, an aliquot is removed from the receiver chamber for analysis. Radioactive or fluorescently-labelled substances permit reliable quantitation of molecular flux. Monolayer integrity is simultaneously measured by the addition of a non-transportable testsubstance such as sucrose or insulin and replicates of at least 4 determinations are measured in order to ensure statistical significance.

EXAMPLE 16

Figure 13:
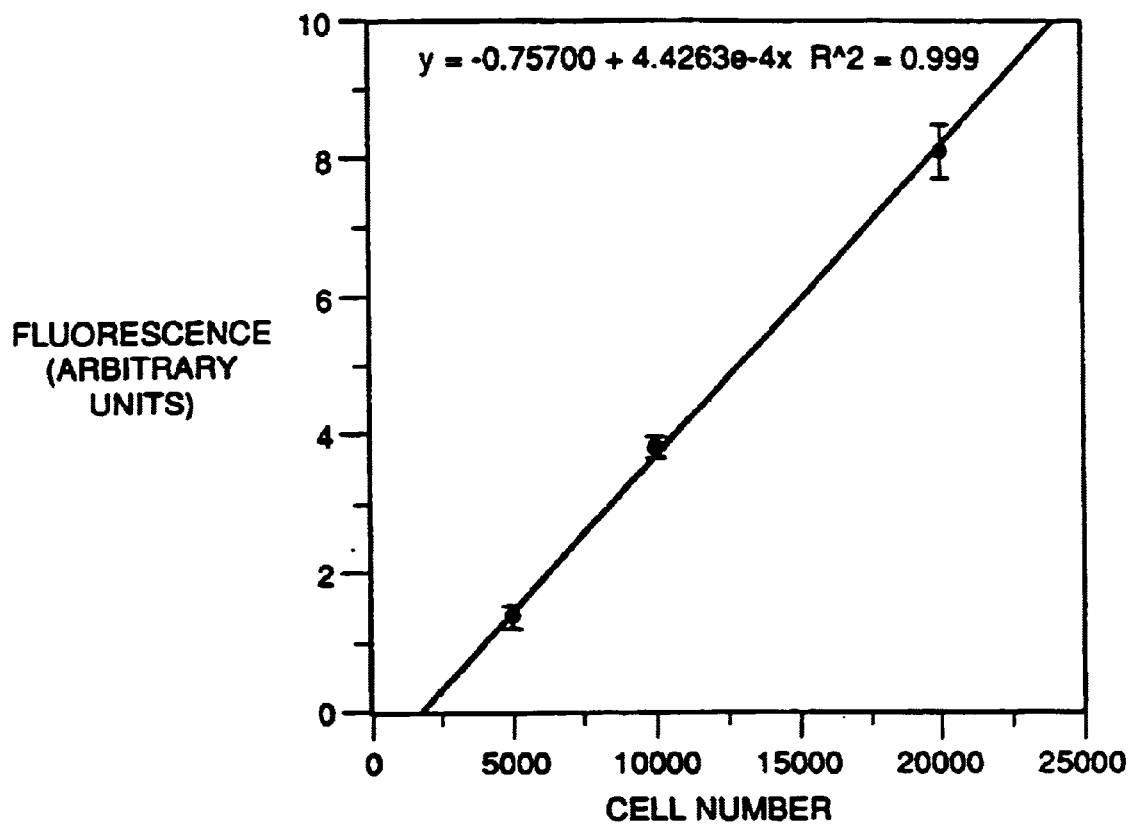
FIG. 13 is a graph illustrating that the relationship between cell number and relative fluorescence is linear.

To determine whether carboxy-terminal linear peptide derivatives of IGFs can promote the survival of cortical neuronal cells, dissociated cultures of embryonic rat cortex were prepared and assayed for the total number of viable cells present after incubation in the presence or absence of peptide. Cortices were dissected from E18 embryonic rats, dissociated by enzymatic digestion or mechanical dissociation and seeded at a density of $6.25 \times 10^4$ cells/cm² in defined insulin/serum-free media (Bottenstein and Sato. PNAS, 75:514–517, (1979)) in the presence or absence of 100 μM peptide. The total number of cells remaining after 4 days was assayed by incubation with the vital stain calcein-AM at 6 μM. This compound is taken up by all cells but can only be converted to a fluorescent derivative by live cells. The relative fluorescence values obtained reflect the total viable cell number. The relationship between cell number and relative fluorescence is linear (FIG. 13), indicating that this is a useful assay to measure relative differences in cell numbers. The carboxy-terminal linear peptide derivatives analyzed were derived from the amino acid regions 55–70 of IGF-I and comparable regions of IGF-III (SEQ ID NO:4) and the comparable region within IGF-II, amino acids 54–67 (SEQ ID NO:3). We found that peptides IGF-II(54–67) (SEQ ID NO:3), IGF-II(58–67) (SEQ ID NO:2) (Example 19), IGF-I(55–70) (SEQ ID NO:4) (Example 21), IGF-II (54–67; D-Y) (SEQ ID NO:45) (Example 24), IGF-II(58–67; D-Y) (SEQ ID NO:46) (Example 23), the amino acid sequence EPYCAPPAKSE (SEQ ID NO:5) (Example 22), and the amino acid sequence TYCAPAKSE (SEQ ID NO:1, Example 20) increased the total number of cells surviving within dissociated preparations of E18 cortical neuronal cultures relative to control cultures incubated without peptide (FIG. 14).

Figure 14A:
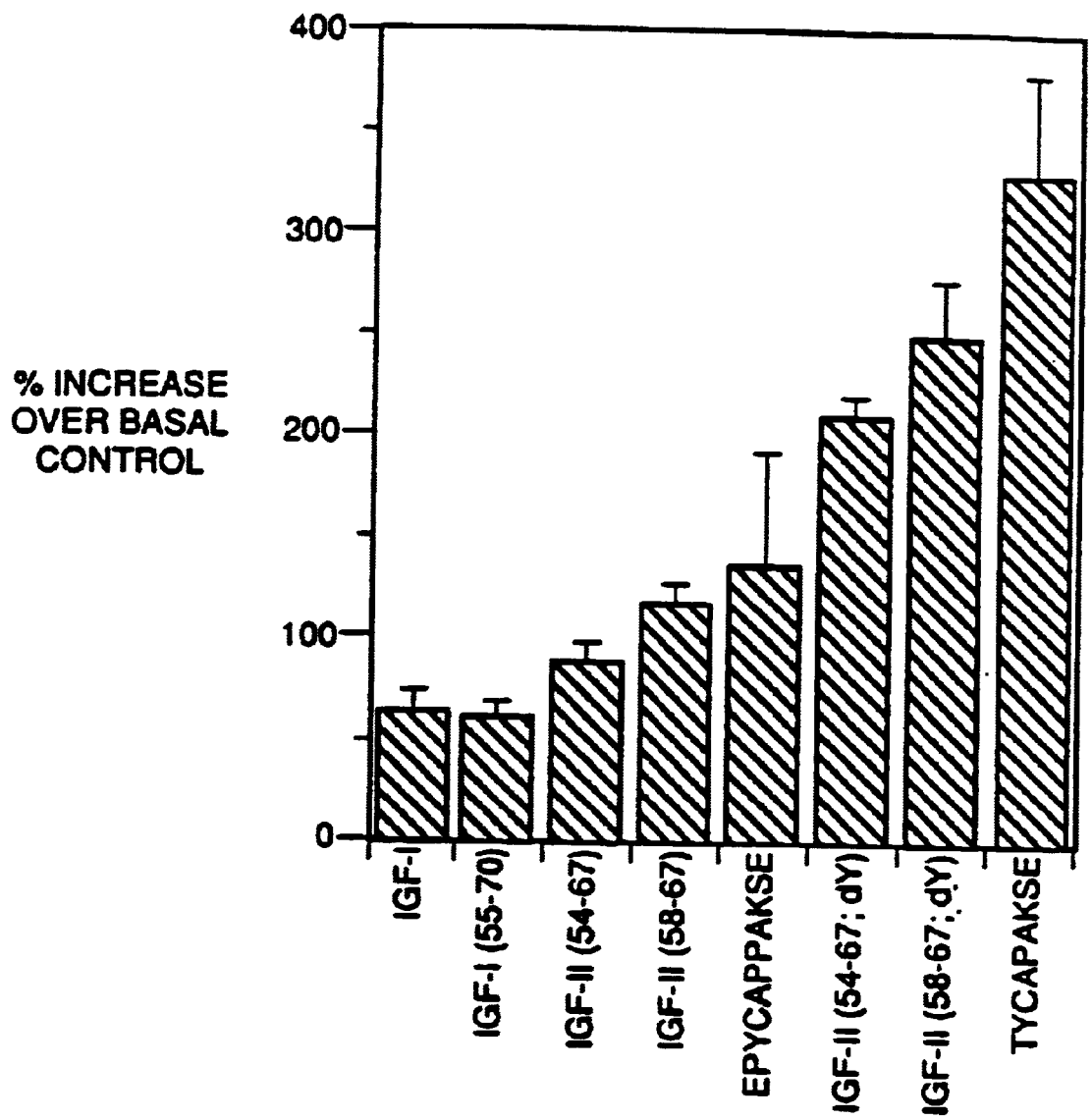
FIG. 14A is a graph illustrating the effect of carboxy-terminal IGF-I and IGF-II peptides, and functional derivatives thereof, on the total number of surviving cells.
Figure 14B:
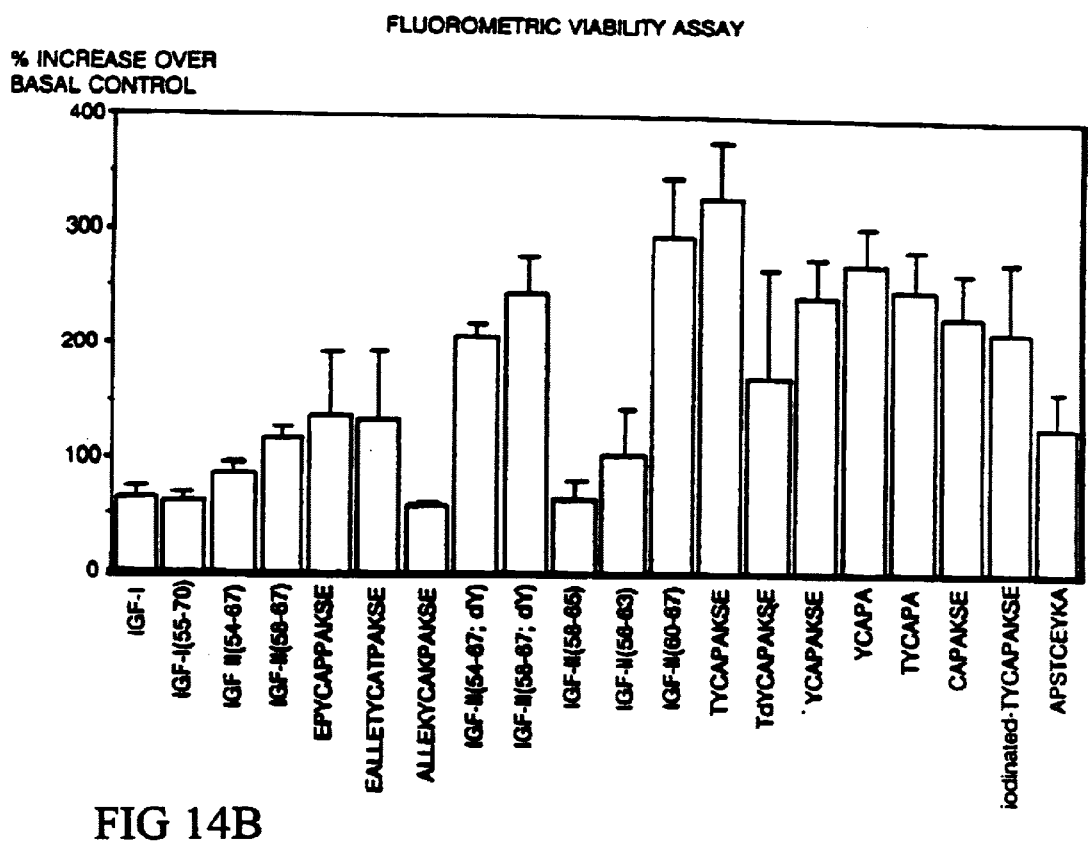
FIG. 14B is a graph illustrating the effect of carboxy-terminal IGF-I and IGF-II peptides, functional derivatives thereof, as well as a "scrambled" peptide, on the total number of surviving cells.

When the same procedure was repeated with a different set of peptides, we found that peptides EALLETYCAT- PAKSE (SEQ ID NO:36), ALLEKYCAKPAKSE (SEQ ID NO:37), IGF-II (58–65) (SEQ ID NO:51), IGF-II (56–63) (SEQ ID NO:52), IGF-II (60–67) (SEQ ID NO:53), TDY-CAPAKSE (SEQ ID NO:50), YCAPAKSE (SEQ ID NO:54), YCAPA (SEQ ID NO:55), TYCAPA (SEQ ID NO:56), CAPAKSE (SEQ ID NO:24), iodinated-TYCAPAKSE (SEQ ID NO:25), and APSTECYKA (SEQ ID NO:38) (see Tables 3 and 4) also increased the total number of cells surviving within dissociated preparations of E18 cortical neuronal cultures relative to control cultures incubated without peptide (FIG. 14a). All of the peptides showing cortical cell survival activity (FIG. 14 or 14a) also showed neurite outgrowth as described below (Example 18).

Figure 15:
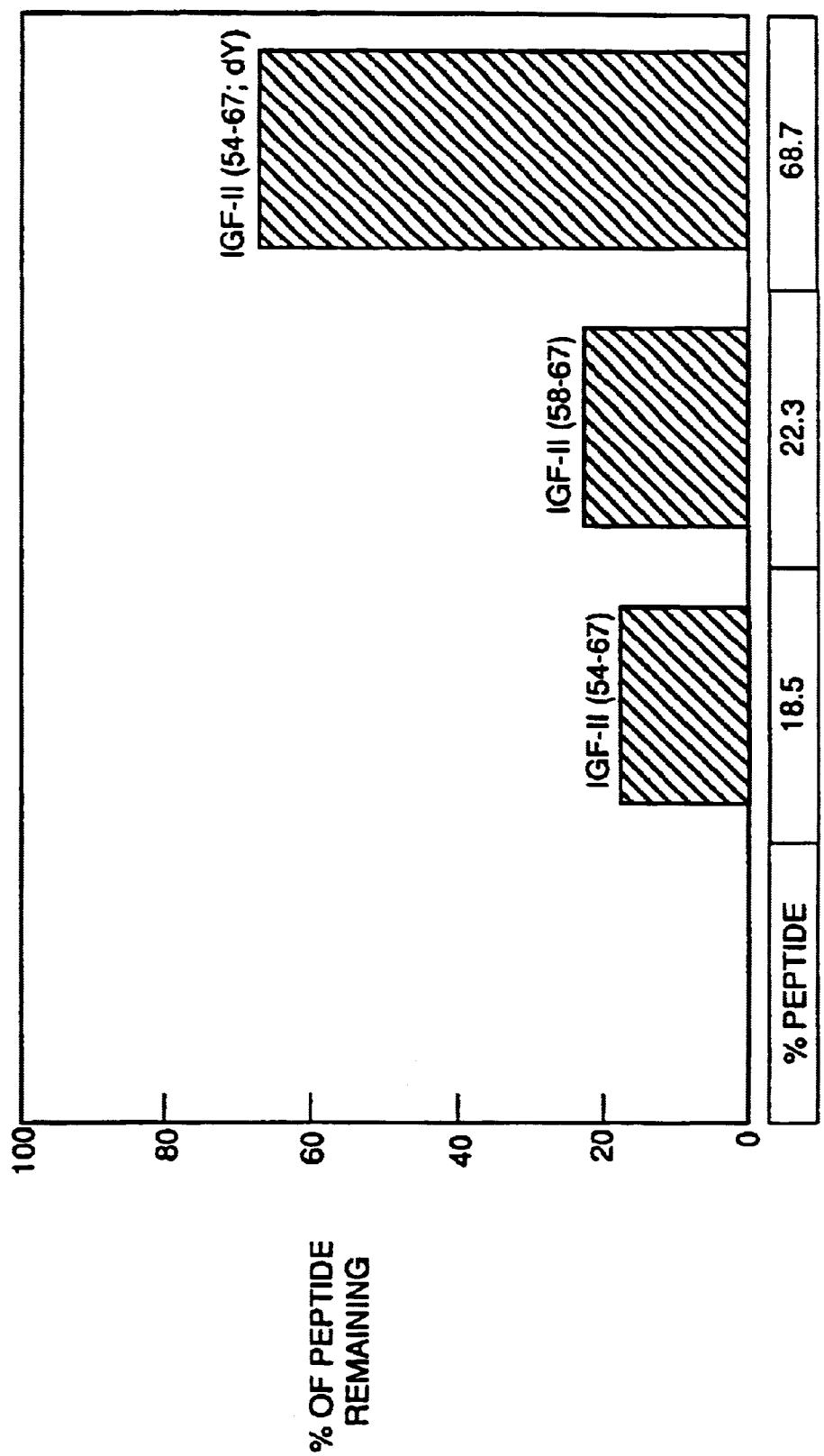
FIG. 15 is a graph illustrating that the D-Y modified peptide IGF-II (54–67) is stabilized against degradation when incubated with cells.

These findings are significant because they define a novel region within the IGFs, and specifically identify novel sequences that possess biological function. The peptides of Examples 22 and 23 are modified peptides containing the D isomer of tryosine (D-Y) at position 59 within IGF-II amino acids 54–67 or 58–67. These modifications were made to prevent peptide bond degradation due to enzymatic cleavage amino terminal to position 60 of IGF-II(54–67) and (58–67). Using a non-denaturing HPLC size exclusion chromatography technique the integrity of peptides IGF-II(54–67) and IGF-II(58–67) was analyzed before and after incubation with cells. FIG. 15 illustrates that the D-Y modified peptide IGF-II(54–67) (SEQ ID NO:45) is stabilized against degradation when incubated with cells.

EXAMPLE 17

Figure 16:
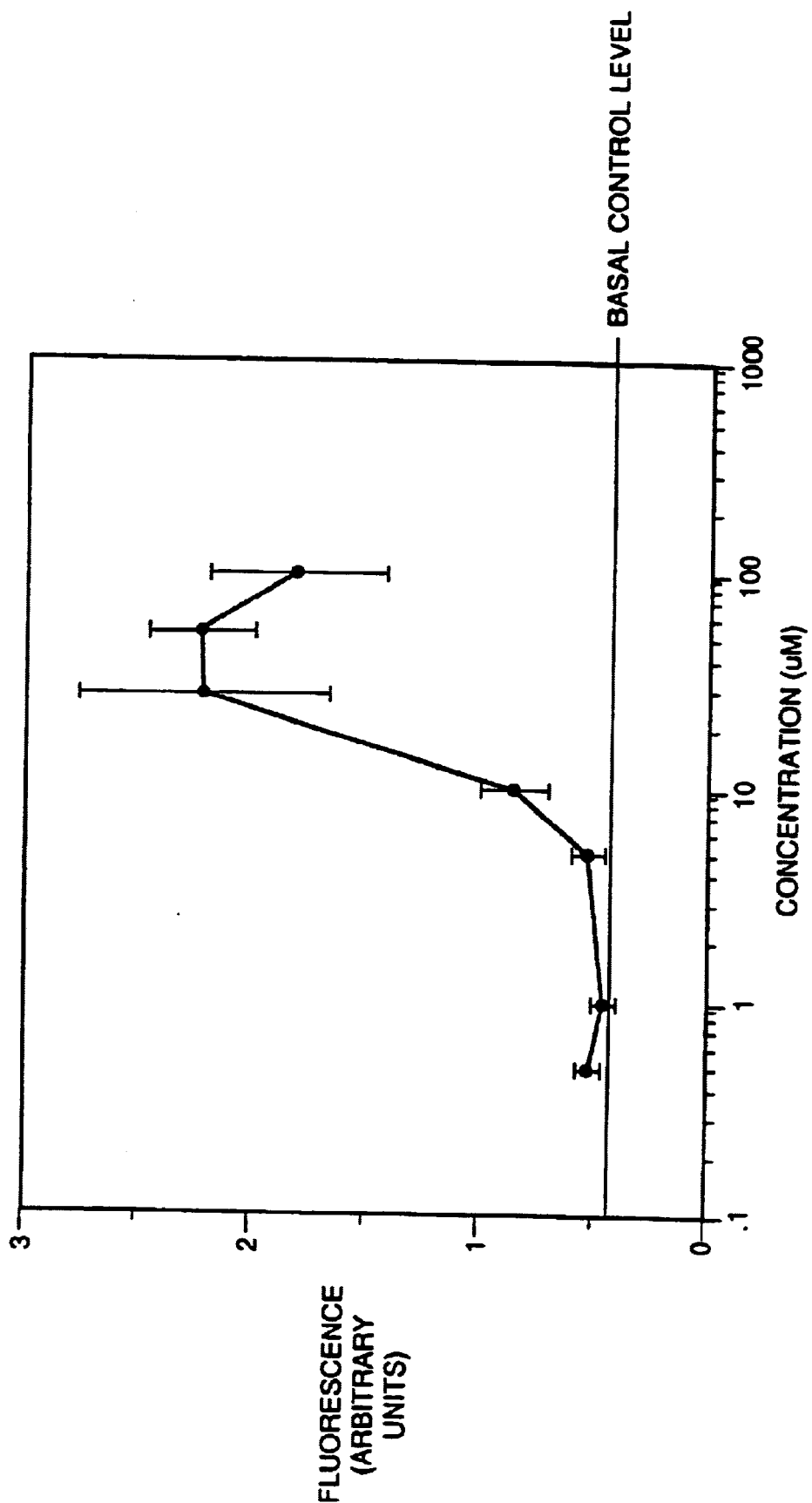
FIG. 16 is a graph illustrating the effect of peptide TYCAPAKSE on cortical neuronal cell survival.

To determine the potency of the carboxy terminal peptides we analyzed the ability of peptides to promote cell survival. We measured the total number of surviving cells within cortical neuronal cultures relative to basal control cultures. FIG. 16 illustrates the concentration-response relationship for peptide TYCAPAKSE (SEQ ID NO:1) and demonstrates that this peptide promotes cortical neuronal cell survival in a dose-dependent manner. All peptides examined are effective within the micromolar concentration range in the fluorometric viability assay.

EXAMPLE 18

Figure 17A:
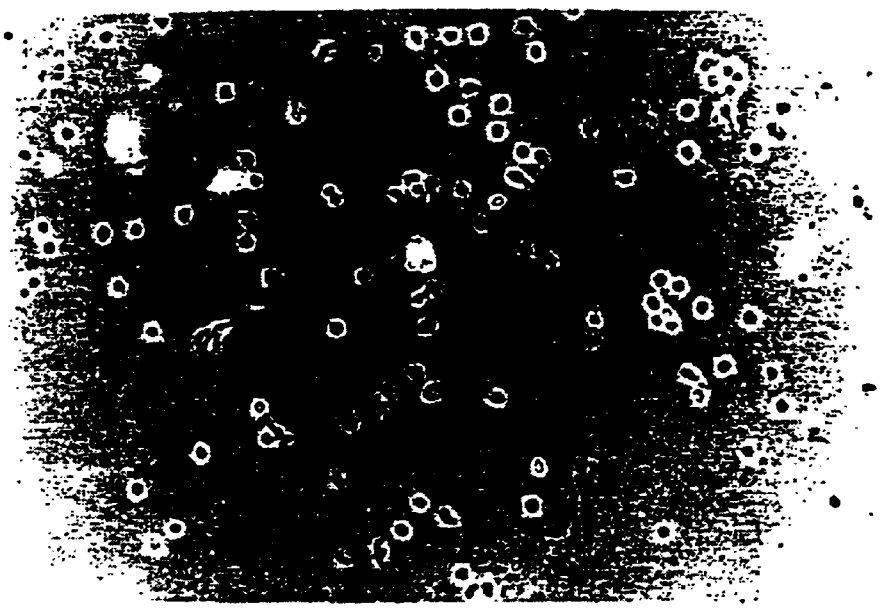
FIG. 17A illustrates neurite outgrowth in the absence of peptide TYCAPAKSE (SEQ ID NO:1).
Figure 17B:
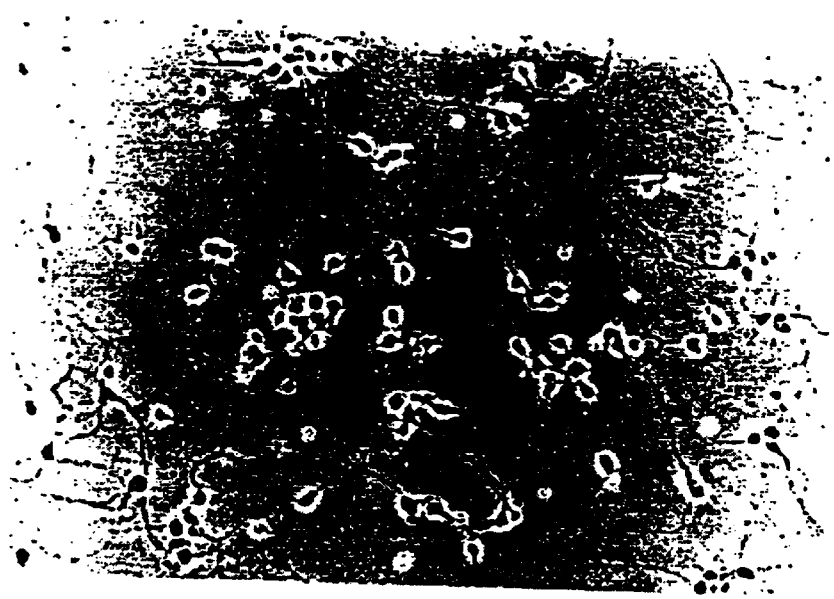
FIG. 17B illustrates the effect of peptide TYCAPAKSE (SEQ ID NO:1) on neurite outgrowth.

To determine whether carboxy-terminal linear peptides of IGFs could promote cortical neurite regeneration, dissociation preparations of E18 rat cortices were cultured in defined insulin/serum-free media in the presence or absence of 100 μM peptides: IGF-II(54–67) (SEQ ID NO:3), IGF-I(55–70) (SEQ ID NO:4), peptide TYCAPAKSE (SEQ ID NO:1), peptides EPYCAPPAKSE (SEQ ID NO:5), IGF-II(54–67; D-Y) (SEQ ID NO:45) and IGF-II(58–67) (SEQ ID NO:2). The cultures were observed 96 hours after peptide exposure and photomicrographs were taken. As illustrated in FIG. 17, peptide-treated cultures displayed more cells with neurite outgrowth than untreated basal control cultures. Similar neurite regenerative responses were observed with all the peptides of this Example. These results demonstrate that carboxy-terminal linear peptide derivatives of IGFs and a novel amino acid sequence not only have a survival promoting effect but also an axonal regenerative effect on cortical neurons.

EXAMPLE 19

The compound TYCATPAKSE (IGF-II(58–67)) (SEQ ID NO:2) was prepared by the solid phase method of peptide synthesis using a Milligen BioSearch Model 9600 Peptide Synthesizer. The general procedure is that described by Hudson (Hudson, J. Chem., 53:617–624 (1988)).

One gram of Fmoc-Glu(t-Butyl)-p-alkoxybenzyl alcohol resin (Milligen/Biosearch) was placed in the reaction vessel and was sequentially allowed to react with 1.5 mM solutions of 1) Fmoc-L-Serine-t-butyl ether
2) ε-t-butyloxycarbonyl-Fmoc-L-Lysine
3) Fmoc-Alanine
4) Fmoc-Proline
5) Fmoc-Threonine-t-butyl ether
6) Fmoc-Alanine
7) S-triphenylmethyl-Fmoc-Cysteine
8) Fmoc-Tyrosine-t-butyl ether
9) Fmoc-Threonine-t-butyl ether in 1:1 dimethylformamide (DMF)/dichloromethane (DCM) using benzotriazol-1-yloxytris(dimethylamino) phosphonium hexafluorophosphate (BOP) and 1-hydroxybenzotriazole (HOBT) as a coupling agent. After each coupling the resin was washed successively with DMF, then DMF/DCM. A solution of 30% of piperidine in 70% of a 1:1 solution of DMF and toluene was used to remove the Fmoc-group, and the resin was washed repeatedly with DMF/DCM. Finally, the crude peptide was removed from 1.41 g of the resin by treatment with 10 mL of a deblocking cocktail containing 90% trifluoroacetic acid, 5% thioanisole, 3% ethanedithiol and 2% anisole. The resulting solution was poured into 10 volumes of ether, and the precipitated solid was separated by filtration and washed with ether.

The resulting crude peptide weighed 0.350 gm. A 100 mg portion was dissolved in 0.5 mL of methanol containing 20 μL of 2-mercaptoethanol to suppress dimerization. The solution was injected in 15 portions into a Waters C8 Bondapak preparative column (25×100 mm) on a Hewlett Packard Model 1050 HPLC system using a solvent gradient of 5% to 60% (in 40 min) acetonitrile in water containing 0.1% trifluoroacetic acid at a flow rate of 9.0 ml per min. The eluted solvent was monitored by an ultraviolet detector at 215 nm.

The peak eluting at 10 min. was collected from a series of nine identical injections. The combined eluates were diluted with an equal volume of water and lyophilized to give 25 mg of purified TYCATPAKSE (SEQ ID NO:2).

The identity of the product was verified by fast atom bombardment mass spectrometry (FAB-MS).

M+H (Calculated) . . . 1070.32
M+H (Found) . . . 1070.00
Amino acid analysis:

|  | Calculated | Found |
| --- | --- | --- |
| Glutamic acid | 1.0 | 1.10 |
| Serine | 1.0 | 0.92 |
| Threonine | 2.0 | 2.04 |
| Alanine | 2.0 | 1.94 |
| Proline | 1.0 | 0.85 |
| Tyrosine | 1.0 | 0.87 |
| Lysine | 1.0 | 1.14 |
| Cysteine | 1.0 | (not determined) |
| Peptide content was calculated as 84.5% | | |

EXAMPLE 20

By a procedure similar to that in the preceeding example the peptide IGF-II(58–67 des Thr62) TYCAPAKSE, (SEQ ID NO:1) was prepared from 0.5 g of resin (same as used in example 1) and one mmole of the respective amino acid derivatives. From the resulting 125 mg of crude peptide, 95 mg was dissolved in 0.6 mL water containing 40 μL 2-mercaptoethanol. A Vydac C18 semipreparative column in the same HPLC system using a solvent gradient 5% to 60% (in 40 min) acetonitrile at a flow of 3.5 mL per minute was used. From a series of 10 identical injections the peak eluting at 9.5 min was collected and lyophilized to give 24.5 mg of the peptide, TYCAPAKSE (SEQ ID NO:1).

The identity of the product was verified by fast atom bombardment mass spectrometry (FAB-MS).

M+H (calculated) . . . 969.19
M+H (found) . . . 969.00
Amino acid analysis:

|  | Calculated | Found |
| --- | --- | --- |
| Glutamic acid | 1.0 | 1.07 |
| Serine | 1.0 | 1.01 |
| Threonine | 1.0 | 1.07 |
| Alanine | 2.0 | 2.21 |
| Proline | 1.0 | 1.08 |
| Tyrosine | 1.0 | 1.00 |
| Lysine | 1.0 | 0.82 |
| Cysteine | 1.0 | (not determined) |
| Peptide content was calculated as 82.0% | | |

EXAMPLE 21

The peptide RRLEMYCAPLKPAKSA (IGF I(55–70) (SEQ ID NO:4)) was prepared by the procedure described in the Example 19 from 0.5 gm of Fmoc-Ala-p-alkoxybenzyl resin (Milligen/Biosearch) and one mole of the respective amino acid derivatives. From the resulting 210 mg of crude peptide, 100 mg was used for purification in a solvent gradient of 15% to 25% (in 30 min) acetonitrile. The conditions and HPLC systems are the same as in example 2. The peak eluting at 14.5 min was collected to give 21 mg of the peptide RRLEMYCAPLKPASKA (SEQ ID NO:4).

The identity of the product was verified by fast atom bombardment mass spectrometry (FAB-MS).

M+H (calculated) 1834.47
M+H (found) 1834.00
Amino acid analysis:

|  | Calculated | Found |
| --- | --- | --- |
| Glutamic acid | 1.0 | 1.13 |
| Serine | 1.0 | 0.89 |
| Arginine | 2.0 | 2.27 |
| Alanine | 3.0 | 2.88 |
| Proline | 2.0 | 1.75 |
| Tyrosine | 1.0 | 0.90 |
| Methionine | 1.0 | 0.83 |
| Leucine | 2.0 | 2.03 |
| Lysine | 2.0 | 2.17 |
| Cysteine | 1.0 | (not determined) |
| Peptide content was calculated 71.4% | | |

EXAMPLE 22

By a procedure similar to that in Example 19 the peptide EPYCAPPAKSE (IGF II(57–67 with Pro at 58 and 62)) (SEQ ID NO:5) was prepared from 1.0 gram of the same resin and one mmole of the respective amino acid derivatives. From the resulting 110 mg of the crude peptide 80 mg was used for purification in a solvent gradient of 10% to 30% (in 40 min) acetonitrile. The conditions and HPLC systems are the same as in example 1. The peak eluting at 10.7 min was collected to give 8.3 mg of the peptide, EPYCAPPAKSE (SEQ ID NO:5).

The identity of the product was verified by fast atom bombardment mass spectrometry (FAB-MS).

M+H (calculated) 1191.33
M+H (found) 1192.00
Amino acid analysis:

|  | Calculated | Found |
| --- | --- | --- |
| Glutamic acid | 2.0 | 2.14 |
| Serine | 1.0 | 0.78 |
| Alanine | 2.0 | 2.13 |
| Proline | 3.0 | 3.01 |
| Tyrosine | 1.0 | 0.97 |
| Lysine | 1.0 | 1.09 |
| Cysteine | 1.0 | (not determined) |
| Peptide content was calculated as 73.3% | | |

EXAMPLE 23

The peptide TDYCATPAKSE (IGF II(58–67 with D-Tyr at 59) (SEQ ID NO:46)) was prepared by the procedure described in Example 19 from 1.0 gm of the same resin. Crude peptide (60 mg) was purified in a solvent gradient 5% to 30% (in 40 min) acetonitrile with the same conditions as in Example 2. The peak eluting at 17.3 min was collected to give 6.5 mg of the peptide, TDYCATPAKSE (SEQ ID NO:46).

The identity of the product was verified by fast atom bombardment mass spectrometry (FAB-MS).

M+H (calculated) 1070.32
M+H (found) 1071.00
Amino acid analysis:

|  | Calculated | Found |
| --- | --- | --- |
| Glutamic acid | 1.0 | 1.00 |
| Serine | 1.0 | 0.97 |
| Threonine | 2.0 | 2.02 |
| Alanine | 2.0 | 2.20 |
| Proline | 1.0 | 1.04 |
| Tyrosine | 1.0 | 0.97 |
| Lysine | 1.0 | 1.02 |
| Cysteine | 1.0 | (not determined) |
| Peptide content was calculated as 88.0% | | |

EXAMPLE 24

The peptide ALLETDYCATPAKSE (IGF II(54–67 with D-Tyr at 59) (SEQ ID NO:45)) was prepared from 0.43 gm of the resin from the synthesis in Example 23 was used to prepare this peptide. Crude peptide (100 mg) was purified in a solvent gradient 15% to 25% (in 40 min) acetonitrile in the same HPLC system as in Example 23. The peak eluting at 13.5 min was collected to give 18.9 mg of the peptide, ALLETDYCATPAKSE (SEQ ID NO:45).

The identity of the product was verified by fast atom bombardment mass spectrometry (FAB-MS).

M+H (calculated) 1497.0
M+H (found) 1469.5

Amino acid analysis:

|  | Calculated | Found |
|---|---|---|
| Glutamic acid | 2.0 | 2.08 |
| Serine | 1.0 | 0.94 |
| Threonine | 2.0 | 2.13 |
| Alanine | 3.0 | 3.12 |
| Proline | 1.0 | 0.95 |
| Tyrosine | 1.0 | 0.97 |
| Leucine | 2.0 | 2.08 |
| Lysine | 1.0 | 0.92 |
| Cysteine | 1.0 | (*not determined) |

Peptide content was calculated as 93.0%

EXAMPLE 25

By a procedure similar to that of Example 20, the peptide des Thr62-D-Tyr59 IGF-II(58–67), TD-YCAPAKSE may be prepared from 0.5 g of the same resin used in Example 1 and one mmole of the respective amino acid derivatives, with the exception that Fmoc-D-Tyrosine-t-butyl ether is substituted for Fmoc-Tyrosine-t-butyl ether. The resulting crude peptide may be purified by HPLC and characterized as TD-YCAPAKSE (SEQ ID NO:50).

EXAMPLE 25-A

Part 1:

Synthesis of CALLETYCATPAKSEC (SEQ ID NO:6)

The compound CALLETYCATPAKSEC (SEQ ID NO:6) was prepared by the solid phase method of peptide synthesis on a Milligen BioSearch Model 9600 Peptide Synthesizer.

0.5 gm (0.46 mM/gm) of Fmoc-Cys (S-triphenylmethyl)-p-alkoxybenzyl alcohol resin (Advanced ChemTech) was placed in the reaction vessel and was sequentially allowed to react with 1.0 mM solutions of
1) Fmoc-Glutamic acid-γ-t-butyl ester
2) Fmoc-Serine-t-butyl ether
3) ε-t-butyloxycarbonyl-Fmoc-Lysine
4) Fmoc-Alanine
5) Fmoc-Proline
6) Fmoc-Threonine-t-butyl ether
7) Fmoc-Alanine
8) S-acetamidomethyl-Fmoc-Cysteine
9) Fmoc-Tyrosine-t-butyl ether
10) Fmoc-Threonine-t-butyl ether
11) Fmoc-Glutamic acid-γ-t-butyl ester
12) Fmoc-Leucine
13) Fmoc-Leucine
14) Fmoc-Alanine
15) S-triphenylmethyl-Fmoc-Cysteine
in 1:1 DMF/DCM using BOP and HOBT as a coupling agent (see Example 19). Finally, the crude peptide CALLETYC(Acm)ATPAKSEC (SEQ ID NO:6) was removed from 0.91 gm of the resin by treatment with 10 mL of a deblocking cocktail containing 90% trifluoroacetic acid, 5% thioanisole, 3% ethanedithiol and 2% anisole. After 4.5 h of stirring the mixture was filtered and the filtrate was dried using argon and precipitated using anhydrous ether. The resulting crude peptide weighed 0.34 gm.

Part 2:

Cyclization of CALLETYC(Acm)ATPAKSEC (SEQ ID NO:6)

The crude peptide (0.3 gm) is dissolved in water (1000 mL) and the pH is adjusted to 8.4 with 50% ammonium hydroxide in water. A dilute solution (0.01 N) of potassium ferricyanide is added dropwise until a pale yellow color persists. After stirring for 2 h, the reaction is quenched by adjusting the solution to pH 4.6 with glacial acetic acid. The excess ferro- and ferricyanide ions are removed by passing through an anion-exchange column. The eluent is concentrated to 10 mL and the solution adjusted to pH 4.6. To remove the acetamidomethyl (Acm) protecting group from the internal Cys, a 0.2 M solution (4 mL) of mercury(II) acetate in 1:1 water/acetic acid is added and the reaction mixture is stirred for an hour. The resulting mixture is desalted and purified by HPLC as described above.

EXAMPLE 25-B

Synthesis of Cyclic TYCAPAKSE (SEQ ID NO:1)

The compound cyclic TYCAPAKSE (SEQ ID NO:1) was prepared by utilizing solid phase (Milligen BioSearch Model 9600 Peptide Synthesizer) and solution phase methods.

0.79 gram (0.97 mM/gm) of p-alkoxybenzyl alcohol resin (Bachem BioScience) was placed in the reaction vessel and was sequentially allowed to react with 3.0 mM solutions of
1) Fmoc-Glutamic acid-γ-benzyl ester
2) Fmoc-Serine-O-benzyl ether
3) ε-benzyloxycarbonyl-Fmoc-Lysine
4) Fmoc-Alanine
5) Fmoc-Proline
6) Fmoc-Alanine
7) S-acetamidomethyl-Fmoc-Cysteine
8) Fmoc-Tyrosine-O-benzyl ether
9) Fmoc-Threonine-O-benzyl ether
in 1:1 DMF/DCM using [2-(1H-benzotriazol-1-yl)-1,1,3,3-tetramethyluroniumtetrafluoroborate (TBTU) and HOBT as a coupling agent. Each of the coupling steps was carried out as described (Example 19). The crude peptide (0.84 g) was removed from 1.82 grams of the resin by treatment with a deblocking cocktail containing 15 mL of TFA, 10 mL of DCM and 0.5 mL of water.

The peptide was dissolved in 30 mL of DMF and added to a solution of 1000 mL DMF containing 2 mL of N-methylmorpholine and 2.5 mL of diphenylphosphorazide over a period of one hour. The solvent was evaporated after overnight stirring. The crude product was dissolved in ethyl acetate (200 mL), and the solution was washed with 2% citric acid, water and 3% sodium bicarbonate. The peptide obtained after evaporation was hydrogenated for an hour using 10% Pd on activated charcoal using ethyl acetate as the solvent. The Acm group was removed from the peptide using mercury (II) acetate and purified using HPLC as described above.

Treating Disorders by Application of Insulin-Like Growth Factors

EXAMPLE 26

Recombinant human IGF-I, IGF-II, and IGF-III, were obtained from commercial sources as indicated in Table I.

The activity of IGF-I, IGF-II and IGF-III was assayed on dissociated cultures of 14.5 day embryonic rat spinal cord neurons. The spinal cords were removed from embryos and dissociated in 0.05% trypsin in Dulbecco's Phosphate Buffered Saline (DPBS). Dissociated cells were seeded onto poly-1-ornithine substrates in 96 well microtiter plates at $2 \times 10^5$ cells/well in 200 µl of serum-free and insulin-free N2 medium (Bottenstein and Sato, 1979 supra) containing 0.05% bovine serum albumin. After a 48 hr incubation at 37° C. in a humidified atmosphere of 5% $CO_2$, 95% air, cultures were assayed for choline acetyltransferase activity according to a modification (McMananman et al., Dev. Bio., 25:311–320 (1988)) of the technique described by Fonnum (Fonnum, J. Neurochem. 24:405–409 (1975)).

Figure 18:
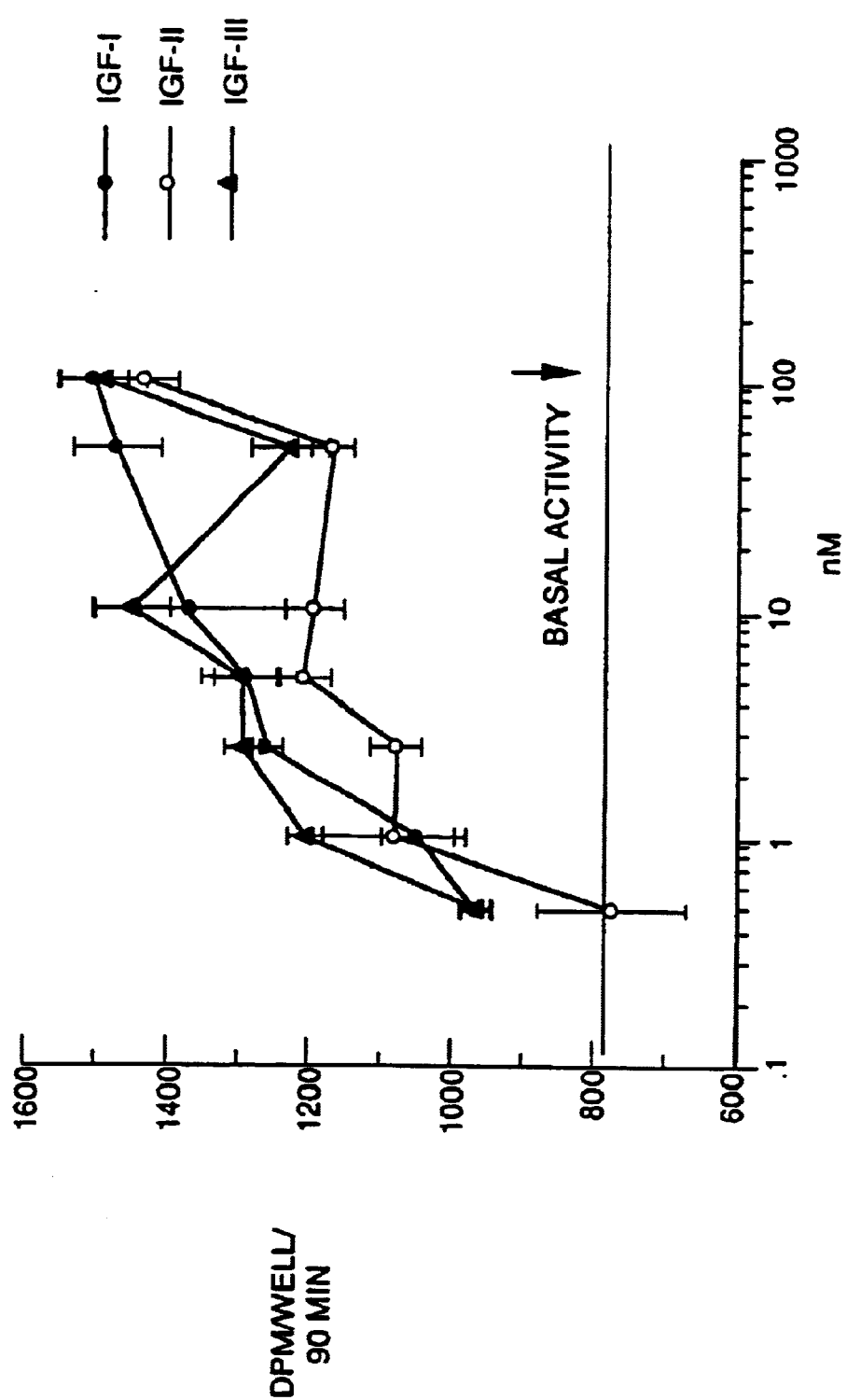
FIG. 18 is a graph illustrating the effect of IGF-I, IGF-II, and IGF-III on choline acetyltransferase activity in spinal cord cells cultured in the absence of serum.
Figure 19:
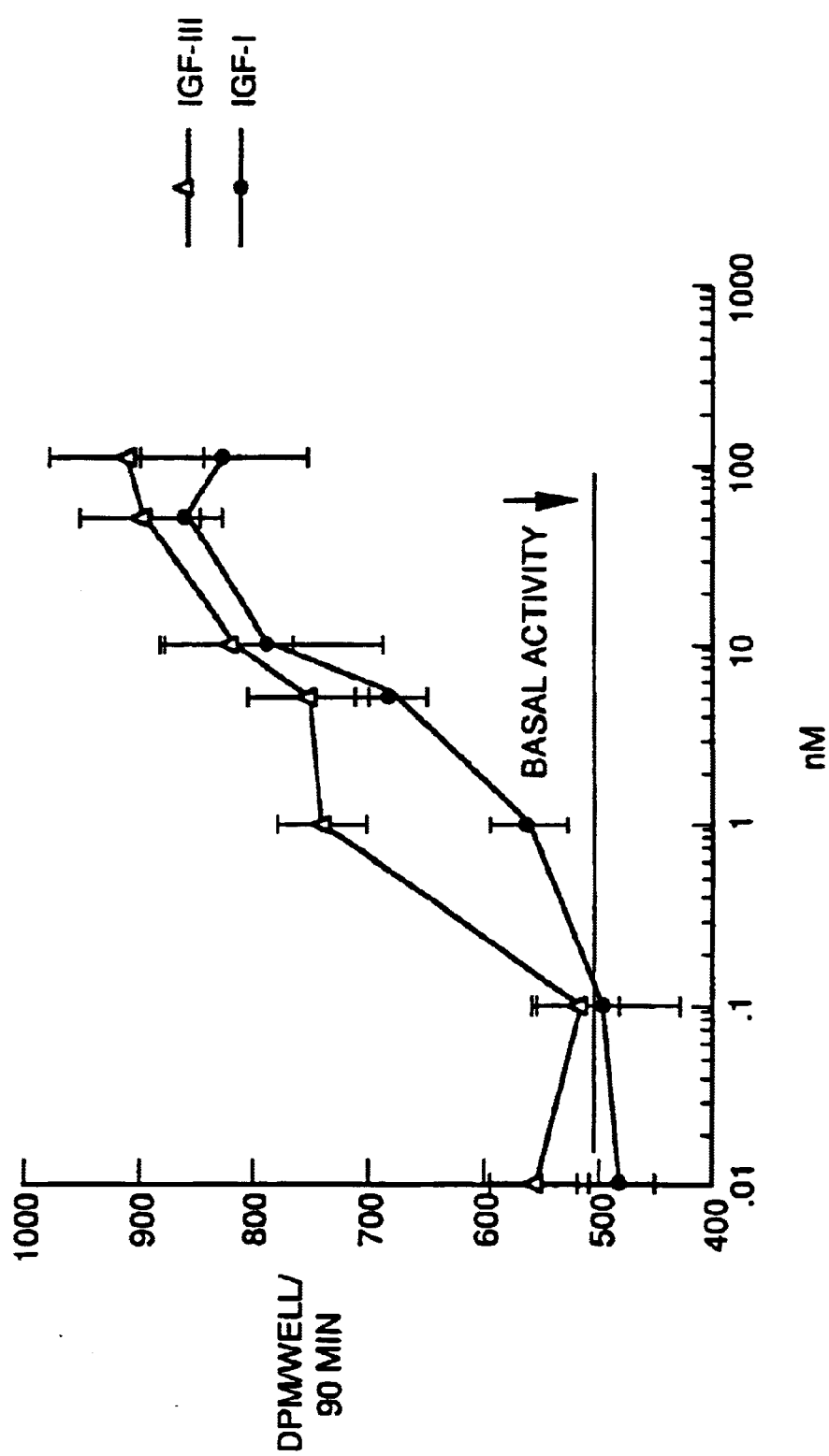
FIG. 19 is a graph illustrating the effect of IGF-I and IGF-II on cortical cell survival.

In this assay, IGF-I, IGF-II, and IGF-III were all found to produce a substantial, dose-dependent increase in choline acetyltransferase activity (FIG. 18). Under these serum-free conditions in which IGF binding protein concentration would be expected to be low, IGF-I and IGF-III have similar efficacy profiles, whereas IGF-II is slightly less potent (FIG. 18). IGF-III, which due to the absence of the 3 N-terminal amino acids found in IGF-I (glycine, proline and glutamate), does not bind substantially to IGF binding proteins found in serum, shows greater potency in increasing ChAT compared with IGF-I in serum containing medium (FIG. 19). These results provide further evidence that IGF-I, II, and III dramatically enhance the survival and/or neurotransmitter-synthesizing capability of spinal cord neurons.

EXAMPLE 27

The neuronal survival promoting activity of IGF-I and IGF-II was assayed on fetal rat cortical neuronal cultures. Cerebral cortices were removed from embryonic day 18 fetal rats. Cortices were minced and treated with neutral protease (Dispase, Collaborative Research) to yield dissociated cell preparations. Cells were plated at low density ($5 \times 10^3$ cells/well) onto poly-L-ornithine and laminin coated ½ area 96 well plates in 50 µl of serum and insulin-free N2 medium containing 0.05% BSA and 50 µM leucine. IGF-I or II were present from time of seeding. Control cultures received no growth factor. Cultures were incubated for 24 hr at 37° C. in an atmosphere of 5% $CO_2$, 95% air. After 24 hrs, [$^3$H]leucine was added in an additional 50 µl of modified N2 medium to a final concentration of 12.5 µCi/ml. Twenty-four hours after the addition of [$^3$H]leucine, cultures were harvested, protein precipitated on filters with 10% trichloroacetic acid, and dried filters counted in a liquid scintillation counter. The incorporation of [$^3$H]leucine into cells is an accurate reflection of cell survival, since incorporated [$^3$H] leucine counts correlated directly with the number of surviving cells as measured by microscopic counts of cells in identical cultures.

Figure 20:
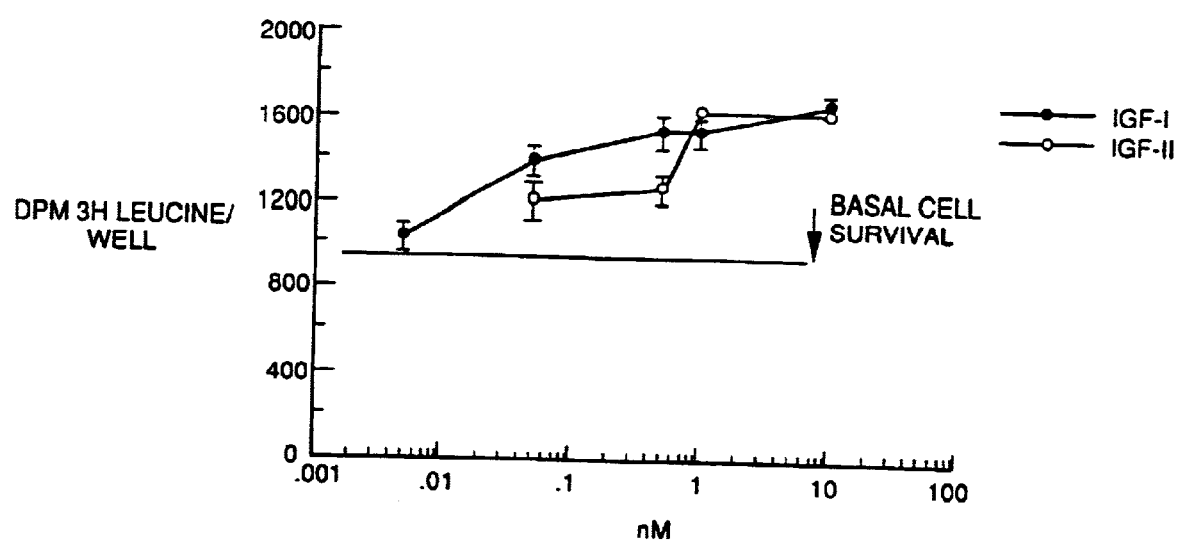
FIG. 20 is a graph illustrating the effect of IGF-I and IGF-II on cortical cell survival.

IGF-I and IGF-II both promoted the survival of cortical neurons with IGF-I being slightly more potent (FIG. 20).

EXAMPLE 28

In the spinal cord, as well as in other regions of the nervous system, neurons are over-produced during development, and undergo a process of naturally occurring cell death prior to parturitio and ends on E10 (reviewed in Oppenheim, R. W. 1991, *Annu Rev. Neurosci.* 14:453–501). During this period, approximately 50% of the motoneurons degenerate and die. Certain neurotrophic agents applied exogenously during this period prevent or retard this form of neuronal death (e.g., partially purified muscle extracts and ciliary neurotrophic factor reduce motor neuron death in chick embryos (McManaman et al., 1990, *Neuron* 4:891–898; Oppenheim et al. 1991, *Science* 251:1616–1617).

Figure 21:
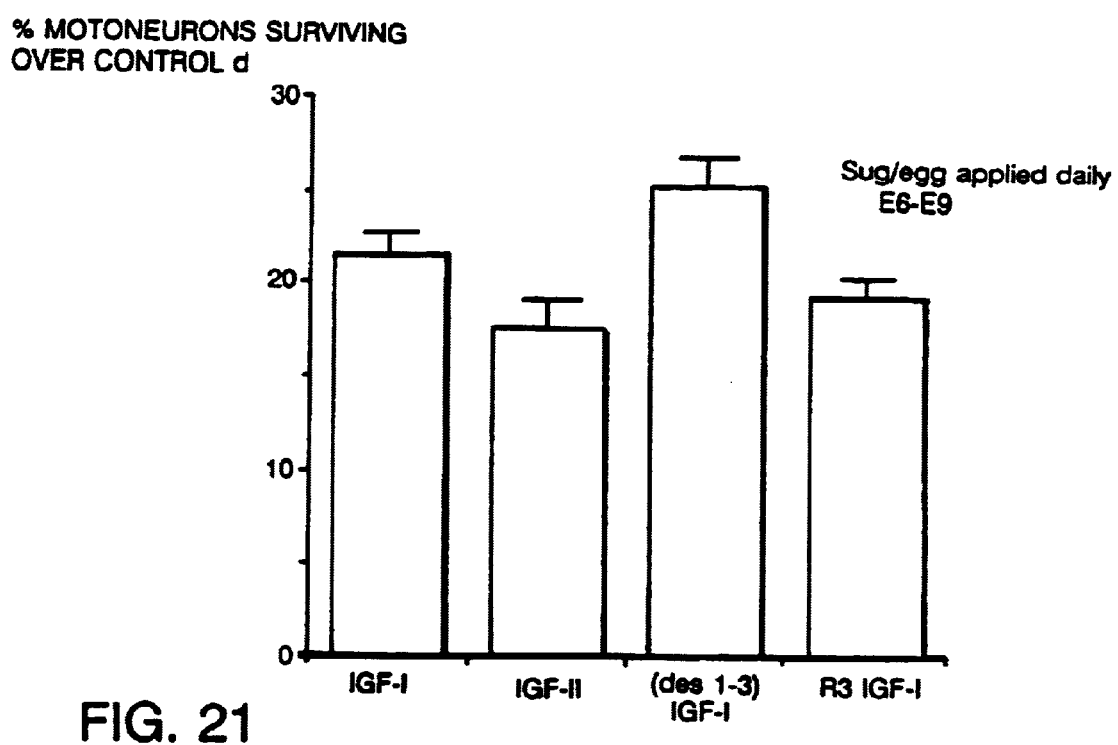
FIG. 21 is a graph illustrating the effect of IGF-I, (des 1–3)IGF-I, R3 IGF-I, and IGF-II in promoting motoneuron survival in ovo.

IGF-I, as well as several variants ({des 1–3} IGF-I, IGF-II, and $R^3$ IGF-I, an analog of IGF-I engineered molecularly by addition of a 13 amino acid extension peptide at the N-terminus and substitution of an Arg for the Glu at position 3 in the natural IGF-I sequence) partially prevented developmentally regulated motoneuron death in this model. The IGFs were administered daily onto chorioallantoic membrane (5 µg/egg in a volume of 50 µl) from embryonic day E6 to E9 through a small window cut into the shell of the egg. Control embryos received an equal volume of vehicle (phosphate buffered saline) alone. On E10, the embryos were removed, sacrificed and the spinal cords sectioned. Motoneurons (identified morphologically in silver-stained sections) were counted in serial sections from both treated and control embryos. The data represented in FIG. 21 demonstrate that applications of IGFs resulted in increased motoneuron survival from 7 to 25% over untreated, control embryos. The differences between effects produced by the different IGFs used were not statistically significant (Student t test P<0.0.5).

Other embodiments are within the following claims.

What is claimed is:

1. A method of enhancing the survival of central nervous system neuronal cells in a mammal, said cells being at risk of drying caused by injury or epilepsy, which method comprises administering to said mammal an effective amount of IGF-I or a functional derivative of IGF-I, wherein said effective amount is administered to the mammal intraventricularly into a lateral ventrical.

2. A method of enhancing the survival of central nervous system neuronal cells in a mammal, said cells being at risk of dying caused by injury or epilepsy, which method comprises administering to said mammal an effective amount of IGF-I.

3. The method of claim 2 wherein said cells risk of dying is caused by injury.

4. The method of claim 2 wherein said cells risk of dying is caused by epilepsy.

5. The method of claim 2 wherein said effective amount of IGF-I is accompanied by an effective amount of IGF-II.

6. The method of claim 2 wherein said effective amount is from 0.01 mg/kg to 100 mg/kg of body weight per day.

7. The method of claim 2 wherein said effective amount is administered to the mammal intraventricularly into a lateral ventrical.

8. A method of therapeutically enhancing the survival of central nervous system neuronal cells in a mammal, said cells being at risk of dying caused by injury or epilepsy, which method comprises administering to said mammal a pharmaceutical or therapeutic composition comprising an effective amount of IGF-I.

\* \* \* \* \*

UNITED STATES PATENT AND TRADEMARK OFFICE
CERTIFICATE OF CORRECTION

PATENT NO. : 6,693,076 B1
DATED : February 17, 2004
INVENTOR(S) : Michael E. Lewis et al.

It is certified that error appears in the above-identified patent and that said Letters Patent is hereby corrected as shown below:

Title page,
Item [56], References Cited, OTHER PUBLICATIONS,
"Daughaday et al," please delete "Ribonuycleic" and insert -- Ribonucleic -- therefor.
"Fellows et al.," please delete "Neruons" and insert -- Neurons -- therefor.
"McManaman et al.," please delete "Wieght" and insert -- Weight -- therefor.
"McManaman et al.," please delete "ot" and insert -- to -- therefor.
"McMorris et al.," please delete "Nucleotrides" and insert -- Nucleotides -- therefor.
"Maly et al.," please delete "factor I" and insert -- Factor I -- therefor.
"Rinehart et al.," please delete "decarxoylase" and insert -- decarboxylase -- therefor.
"Silver," please delete "Astoglial" and insert -- Astroglial -- therefor.
"*Principles of Neural Science*," please delete "Prentic" and insert -- Prentice -- therefor.
"McGreer et al.," please delete "McGreer" and insert -- McGeer -- therefor.
"Gluckman et al.," please delete "of IGF-1 in the resuce" and insert -- for IGF-1 in the rescue -- therefor.

Column 1,
Line 56, please delete "No. 227,269" and insert -- No. 227,619 -- therefor.

Column 2,
Line 6, please delete "carcinostratic" and insert -- carcinostatic -- therefor.
Line 36, please delete "increase" and insert -- increases -- therefor.

Column 6,
Line 4, please delete "polypeptide" and insert -- polypeptides -- therefor.

Column 7,
Line 54, please delete "peptid" and insert -- peptide -- therefor.

Column 8,
Line 42, please delete "fragment of" and insert -- fragment or -- therefor.

Column 9,
Line 28, please delete "peptides" and insert -- peptidases -- therefor.

Column 10,
Line 62, please delete "molecules" and insert -- molecule -- therefor.

Column 11,
Line 17, please delete "increases" and insert -- increase-- therefore
Line 19, please delete "enhance" and insert -- enhancer -- therefor.

UNITED STATES PATENT AND TRADEMARK OFFICE
CERTIFICATE OF CORRECTION

PATENT NO. : 6,693,076 B1
DATED : February 17, 2004
INVENTOR(S) : Michael E. Lewis et al.

It is certified that error appears in the above-identified patent and that said Letters Patent is hereby corrected as shown below:

Column 13,
Line 63, please delete "aralkoxy-carbonyl" and insert -- aralkyloxy-carbonyl-- therefore
Line 64, please delete "alkyloxycarbon" and insert -- alkyloxycarbonyl -- therefor.

Column 14,
Line 55, please delete "aralkoxy" and insert -- aralkyloxy -- therefor.

Column 15,
Line 15, please delete "5-50" and insert -- 5-40 -- therefor.

Column 20,
Line 3, please delete "1-25" and insert -- 11-25 -- therefor.

Column 24,
Line 16, please delete "49" from the third column and delete "(11)" from the fourth column
Line 17, please insert -- 49 -- in the third column and --(11) -- in the fourth column.

Column 59,
Line 43, please delete "drying" and insert -- dying -- therefor.

Signed and Sealed this

Twenty-first Day of September, 2004

JON W. DUDAS
*Director of the United States Patent and Trademark Office*

SEQUENCE LISTING (1) GENERAL INFORMATION:

(iii) NUMBER OF SEQUENCES: 56

(2) INFORMATION FOR SEQ ID NO: 1:

(i) SEQUENCE CHARACTERISTICS:
        (A) LENGTH: 9
        (B) TYPE: amino acid
        (C) STRANDEDNESS:
        (D) TOPOLOGY: linear (xi) SEQUENCE DESCRIPTION: SEQ ID NO: 1:

Thr Tyr Cys Ala Pro Ala Lys Ser Glu
1             5

(2) INFORMATION FOR SEQ ID NO: 2:

(i) SEQUENCE CHARACTERISTICS:
        (A) LENGTH: 10
        (B) TYPE: amino acid (C) STRANDEDNESS:
          (D) TOPOLOGY: linear (xi) SEQUENCE DESCRIPTION: SEQ ID NO: 2:

Thr Tyr Cys Ala Thr Pro Ala Lys Ser Glu
1               5                   10

(2) INFORMATION FOR SEQ ID NO: 3:

(i) SEQUENCE CHARACTERISTICS:
          (A) LENGTH: 14
          (B) TYPE: amino acid
          (C) STRANDEDNESS:
          (D) TOPOLOGY: linear (xi) SEQUENCE DESCRIPTION: SEQ ID NO: 3:

Ala Leu Leu Glu Thr Tyr Cys Ala Thr Pro Ala Lys Ser Glu
1               5                   10

(2) INFORMATION FOR SEQ ID NO: 4:

(i) SEQUENCE CHARACTERISTICS:
          (A) LENGTH: 16
          (B) TYPE: amino acid
          (C) STRANDEDNESS:
          (D) TOPOLOGY: linear (xi) SEQUENCE DESCRIPTION: SEQ ID NO: 4:

Arg Arg Leu Glu Met Tyr Cys Ala Pro Leu Lys Pro Ala Lys
1               5                   10

Ser Ala
15

(2) INFORMATION FOR SEQ ID NO: 5:

(i) SEQUENCE CHARACTERISTICS:
          (A) LENGTH: 11
          (B) TYPE: amino acid
          (C) STRANDEDNESS:
          (D) TOPOLOGY: linear (xi) SEQUENCE DESCRIPTION: SEQ ID NO: 5:

Glu Pro Tyr Cys Ala Pro Pro Ala Lys Ser Glu
1               5                   10

(2) INFORMATION FOR SEQ ID NO: 6:

(i) SEQUENCE CHARACTERISTICS:
          (A) LENGTH: 16
          (B) TYPE: amino acid
          (C) STRANDEDNESS:
          (D) TOPOLOGY: linear (xi) SEQUENCE DESCRIPTION: SEQ ID NO: 6:

Cys Ala Leu Leu Glu Thr Tyr Cys Ala Thr Pro Ala Lys Ser Glu Cys
1               5                   10                  15

(2) INFORMATION FOR SEQ ID NO: 7:

(i) SEQUENCE CHARACTERISTICS:
          (A) LENGTH: 12
          (B) TYPE: amino acid
          (C) STRANDEDNESS:
          (D) TOPOLOGY: linear (xi) SEQUENCE DESCRIPTION: SEQ ID NO: 7:

Cys Thr Tyr Cys Ala Thr Pro Ala Lys Ser Glu Cys (2) INFORMATION FOR SEQ ID NO: 8:

(i) SEQUENCE CHARACTERISTICS:
        (A) LENGTH: 13
        (B) TYPE: amino acid
        (C) STRANDEDNESS:
        (D) TOPOLOGY: linear (xi) SEQUENCE DESCRIPTION: SEQ ID NO: 8:

```
Cys Glu Pro Tyr Cys Ala Pro Pro Ala Lys Ser Glu Cys
1               5                   10
```

(2) INFORMATION FOR SEQ ID NO: 9:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 9:

```
Cys Thr Tyr Cys Ala Pro Ala Lys Ser Glu Cys
1               5                   10
```

(2) INFORMATION FOR SEQ ID NO: 10:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 10:

```
Cys Thr Tyr Thr Ala Pro Ala Lys Ser Glu Cys
1               5                   10
```

(2) INFORMATION FOR SEQ ID NO: 11:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 11:

```
Cys Ala Leu Leu Glu Thr Tyr Ala Thr Pro Ala Lys Ser Glu Cys
1               5                   10                  15
```

(2) INFORMATION FOR SEQ ID NO: 12:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQ ID NO: 12:

```
Cys Arg Arg Leu Glu Met Tyr Cys Ala Pro Leu Lys Pro Ala Lys Ser
1               5                   10                  15

Ala Cys
```

(2) INFORMATION FOR SEQ ID NO: 13:

(i) SEQUENCE CHARACTERISTICS:
        (A) LENGTH: 14

(B) TYPE: amino acid
        (C) STRANDEDNESS:
        (D) TOPOLOGY: linear (xi) SEQUENCE DESCRIPTION: SEQ ID NO: 13:

Cys Gly Tyr Gly Ser Ser Ser Arg Arg Ala Pro Gln Thr Cys
1               5                   10

(2) INFORMATION FOR SEQ ID NO: 14:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 14:

Cys Tyr Phe Asn Lys Pro Thr Gly Tyr Gly Cys
1               5                   10

(2) INFORMATION FOR SEQ ID NO: 15:

(i) SEQUENCE CHARACTERISTICS:
        (A) LENGTH: 20
        (B) TYPE: amino acid
        (C) STRANDEDNESS:
        (D) TOPOLOGY: linear (xi) SEQUENCE DESCRIPTION: SEQ ID NO: 15:

Cys Tyr Phe Asn Lys Pro Thr Gly Tyr Gly Ser Ser Ser Arg Arg Ala
1               5                   10                  15

Pro Gln Thr Cys
            20

(2) INFORMATION FOR SEQ ID NO: 16:

(i) SEQUENCE CHARACTERISTICS:
        (A) LENGTH: 12
        (B) TYPE: amino acid
        (C) STRANDEDNESS:
        (D) TOPOLOGY: linear (xi) SEQUENCE DESCRIPTION: SEQ ID NO: 16:

Cys Lys Pro Thr Gly Tyr Gly Ser Ser Ser Arg Cys
1               5                   10

(2) INFORMATION FOR SEQ ID NO: 17:

(i) SEQUENCE CHARACTERISTICS:
        (A) LENGTH: 70
        (B) TYPE: amino acid
        (C) STRANDEDNESS:
        (D) TOPOLOGY: linear (xi) SEQUENCE DESCRIPTION: SEQ ID NO: 17:

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala
65                  70

(2) INFORMATION FOR SEQ ID NO: 18:

(i) SEQUENCE CHARACTERISTICS:
        (A) LENGTH: 13
        (B) TYPE: amino acid
        (C) STRANDEDNESS:
        (D) TOPOLOGY: linear (xi) SEQUENCE DESCRIPTION: SEQ ID NO: 18:

```
Cys Gly Cys Glu Leu Val Asp Ala Leu Gln Phe Val Cys
1               5                   10
```

(2) INFORMATION FOR SEQ ID NO: 19:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 19:

```
Cys Asp Leu Arg Arg Leu Glu Met Tyr Cys
1               5                   10
```

(2) INFORMATION FOR SEQ ID NO: 20:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 20:

```
Cys Cys Phe Arg Ser Cys Asp Leu Arg Arg Leu Glu Met Tyr Cys
1               5                   10                  15
```

(2) INFORMATION FOR SEQ ID NO: 21:

(i) SEQUENCE CHARACTERISTICS:
        (A) LENGTH: 19
        (B) TYPE: amino acid
        (C) STRANDEDNESS:
        (D) TOPOLOGY: linear (xi) SEQUENCE DESCRIPTION: SEQ ID NO: 21:

```
Cys Asp Leu Arg Arg Leu Glu Met Tyr Cys Cys Pro Leu Lys Pro Ala
1               5                   10                  15

Lys Ser Glu
```

(2) INFORMATION FOR SEQ ID NO: 22:

(i) SEQUENCE CHARACTERISTICS:
        (A) LENGTH: 6
        (B) TYPE: amino acid
        (C) STRANDEDNESS:
        (D) TOPOLOGY: linear (xi) SEQUENCE DESCRIPTION: SEQ ID NO: 22:

```
Cys Cys Phe Arg Ser Cys
1               5
```

(2) INFORMATION FOR SEQ ID NO: 23:

(i) SEQUENCE CHARACTERISTICS:
        (A) LENGTH: 5
        (B) TYPE: amino acid

```
            (C) STRANDEDNESS:
            (D) TOPOLOGY: linear (xi) SEQUENCE DESCRIPTION: SEQ ID NO: 23:

Cys Phe Arg Ser Cys
1               5

(2) INFORMATION FOR SEQ ID NO: 24:

(i) SEQUENCE CHARACTERISTICS:
            (A) LENGTH: 7
            (B) TYPE: amino acid
            (C) STRANDEDNESS:
            (D) TOPOLOGY: linear (xi) SEQUENCE DESCRIPTION: SEQ ID NO: 24:

Cys Ala Pro Ala Lys Ser Glu
1               5

(2) INFORMATION FOR SEQ ID NO: 25:

(i) SEQUENCE CHARACTERISTICS:
            (A) LENGTH: 9
            (B) TYPE: amino acid
            (C) STRANDEDNESS:
            (D) TOPOLOGY: linear (ix) FEATURE:
            (D) OTHER INFORMATION: Xaa represents an iodinated tyrosine.

(xi) SEQUENCE DESCRIPTION: SEQ ID NO: 25:

Thr Xaa Cys Ala Pro Ala Lys Ser Glu
1               5

(2) INFORMATION FOR SEQ ID NO: 26:

(i) SEQUENCE CHARACTERISTICS:
            (A) LENGTH: 7
            (B) TYPE: amino acid
            (C) STRANDEDNESS:
            (D) TOPOLOGY: linear (xi) SEQUENCE DESCRIPTION: SEQ ID NO: 26:

Cys Gly Pro Glu Thr Leu Cys
1               5

(2) INFORMATION FOR SEQ ID NO: 27:

(i) SEQUENCE CHARACTERISTICS:
            (A) LENGTH: 19
            (B) TYPE: amino acid
            (C) STRANDEDNESS:
            (D) TOPOLOGY: linear (xi) SEQUENCE DESCRIPTION: SEQ ID NO: 27:

Cys Gly Tyr Gly Ser Ser Ser Arg Arg Cys Pro Gln Thr Gly Ile Val
1               5                   10                  15

Asp Glu Cys (2) INFORMATION FOR SEQ ID NO: 28:

(i) SEQUENCE CHARACTERISTICS:
            (A) LENGTH: 13
            (B) TYPE: amino acid
            (C) STRANDEDNESS:
            (D) TOPOLOGY: linear (xi) SEQUENCE DESCRIPTION: SEQ ID NO: 28:
```

```
Cys Gly Asp Arg Gly Phe Tyr Phe Asn Lys Pro Thr Cys
1               5                   10
```

(2) INFORMATION FOR SEQ ID NO: 29:

(i) SEQUENCE CHARACTERISTICS:
        (A) LENGTH: 11
        (B) TYPE: amino acid
        (C) STRANDEDNESS:
        (D) TOPOLOGY: linear (xi) SEQUENCE DESCRIPTION: SEQ ID NO: 29:

```
Cys Cys Pro Leu Lys Pro Ala Lys Ser Ala Cys
1               5                   10
```

(2) INFORMATION FOR SEQ ID NO: 30:

(i) SEQUENCE CHARACTERISTICS:
        (A) LENGTH: 19
        (B) TYPE: amino acid
        (C) STRANDEDNESS:
        (D) TOPOLOGY: linear (xi) SEQUENCE DESCRIPTION: SEQ ID NO: 30:

```
Cys Asp Leu Arg Arg Leu Glu Met Tyr Ala Pro Leu Lys Pro Ala
1               5                   10                  15

Lys Ser Ala Cys
```

(2) INFORMATION FOR SEQ ID NO: 31:

(i) SEQUENCE CHARACTERISTICS:
        (A) LENGTH: 67
        (B) TYPE: amino acid
        (C) STRANDEDNESS:
        (D) TOPOLOGY: linear (xi) SEQUENCE DESCRIPTION: SEQ ID NO: 31:

```
Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65
```

(2) INFORMATION FOR SEQ ID NO: 32:

(i) SEQUENCE CHARACTERISTICS:
        (A) LENGTH: 13
        (B) TYPE: amino acid
        (C) STRANDEDNESS:
        (D) TOPOLOGY: linear (xi) SEQUENCE DESCRIPTION: SEQ ID NO: 32:

```
Cys Gly Gly Glu Leu Val Asp Thr Leu Gln Phe Val Cys
1               5                   10
```

(2) INFORMATION FOR SEQ ID NO: 33:

(i) SEQUENCE CHARACTERISTICS:
        (A) LENGTH: 10

```
            (B) TYPE: amino acid
            (C) STRANDEDNESS:
            (D) TOPOLOGY: linear (xi) SEQUENCE DESCRIPTION: SEQ ID NO: 33:

Cys Asp Leu Cys Leu Leu Glu Thr Tyr Cys
1               5                   10

(2) INFORMATION FOR SEQ ID NO: 34:

(i) SEQUENCE CHARACTERISTICS:
            (A) LENGTH: 16
            (B) TYPE: amino acid
            (C) STRANDEDNESS:
            (D) TOPOLOGY: linear (xi) SEQUENCE DESCRIPTION: SEQ ID NO: 34:

Cys Cys Phe Arg Ser Cys Asp Asp Leu Ala Leu Leu Glu Thr Tyr Cys
1               5                   10                  15

(2) INFORMATION FOR SEQ ID NO: 35:

(i) SEQUENCE CHARACTERISTICS:
            (A) LENGTH: 17
            (B) TYPE: amino acid
            (C) STRANDEDNESS:
            (D) TOPOLOGY: linear (xi) SEQUENCE DESCRIPTION: SEQ ID NO: 35:

Cys Asp Leu Cys Leu Leu Glu Thr Tyr Cys Ala Thr Pro Ala Lys Ser
1               5                   10                  15
Glu (2) INFORMATION FOR SEQ ID NO: 36:

(i) SEQUENCE CHARACTERISTICS:
            (A) LENGTH: 15
            (B) TYPE: amino acid
            (C) STRANDEDNESS:
            (D) TOPOLOGY: linear (xi) SEQUENCE DESCRIPTION: SEQ ID NO: 36:

Glu Ala Leu Leu Glu Thr Tyr Cys Ala Thr Pro Ala Lys Ser Glu
1               5                   10                  15

(2) INFORMATION FOR SEQ ID NO: 37:

(i) SEQUENCE CHARACTERISTICS:
            (A) LENGTH: 14
            (B) TYPE: amino acid
            (C) STRANDEDNESS:
            (D) TOPOLOGY: linear (xi) SEQUENCE DESCRIPTION: SEQ ID NO: 37:

Ala Leu Leu Glu Lys Tyr Cys Ala Lys Pro Ala Lys Ser Glu
1               5                   10

(2) INFORMATION FOR SEQ ID NO: 38:

(i) SEQUENCE CHARACTERISTICS:
            (A) LENGTH: 9
            (B) TYPE: amino acid
            (C) STRANDEDNESS:
            (D) TOPOLOGY: linear (xi) SEQUENCE DESCRIPTION: SEQ ID NO: 38:

Ala Pro Ser Thr Cys Glu Tyr Lys Ala
```

```
1               5
```

(2) INFORMATION FOR SEQ ID NO: 39:

(i) SEQUENCE CHARACTERISTICS:
        (A) LENGTH: 15
        (B) TYPE: amino acid
        (C) STRANDEDNESS:
        (D) TOPOLOGY: linear (xi) SEQUENCE DESCRIPTION: SEQ ID NO: 39:

```
Cys Cys Phe Arg Ser Cys Asp Leu Cys Leu Leu Glu Thr Tyr Cys
1               5                   10                  15
```

(2) INFORMATION FOR SEQ ID NO: 40:

(i) SEQUENCE CHARACTERISTICS:
        (A) LENGTH: 10
        (B) TYPE: amino acid
        (C) STRANDEDNESS:
        (D) TOPOLOGY: linear (xi) SEQUENCE DESCRIPTION: SEQ ID NO: 40:

```
Cys Cys Tyr Arg Pro Ser Glu Thr Leu Cys
1               5                   10
```

(2) INFORMATION FOR SEQ ID NO: 41:

(i) SEQUENCE CHARACTERISTICS:
        (A) LENGTH: 18
        (B) TYPE: amino acid
        (C) STRANDEDNESS:
        (D) TOPOLOGY: linear (xi) SEQUENCE DESCRIPTION: SEQ ID NO: 41:

```
Cys Arg Pro Cys Ser Arg Val Ser Arg Arg Ser Arg Gly Ile Val Glu Glu
1               5                   10                  15
Cys
```

(2) INFORMATION FOR SEQ ID NO: 42:

(i) SEQUENCE CHARACTERISTICS:
        (A) LENGTH: 12
        (B) TYPE: amino acid
        (C) STRANDEDNESS:
        (D) TOPOLOGY: linear (xi) SEQUENCE DESCRIPTION: SEQ ID NO: 42:

```
Cys Gly Asp Arg Gly Phe Tyr Phe Ser Arg Pro Cys
1               5                   10
```

(2) INFORMATION FOR SEQ ID NO: 43:

(i) SEQUENCE CHARACTERISTICS:
        (A) LENGTH: 9
        (B) TYPE: amino acid
        (C) STRANDEDNESS:
        (D) TOPOLOGY: linear (xi) SEQUENCE DESCRIPTION: SEQ ID NO: 43:

```
Cys Cys Thr Pro Ala Lys Ser Glu Cys
1               5
```

(2) INFORMATION FOR SEQ ID NO: 44:

(i) SEQUENCE CHARACTERISTICS:
        (A) LENGTH: 16

(B) TYPE: amino acid
        (C) STRANDEDNESS:
        (D) TOPOLOGY: linear (xi) SEQUENCE DESCRIPTION: SEQ ID NO: 44:

Cys Asp Leu Cys Leu Leu Glu Thr Ala Thr Pro Ala Lys Ser Glu Cys
1               5                   10                  15

(2) INFORMATION FOR SEQ ID NO: 45:

(i) SEQUENCE CHARACTERISTICS:
        (A) LENGTH: 14
        (B) TYPE: amino acid
        (C) STRANDEDNESS:
        (D) TOPOLOGY: linear (ix) FEATURE:
        (D) OTHER INFORMATION: Xaa represents the D-isomer of
            tyrosine.

(xi) SEQUENCE DESCRIPTION: SEQ ID NO: 45:

Ala Leu Leu Glu Thr Xaa Cys Ala Thr Pro Ala Lys Ser Glu
1               5                   10

(2) INFORMATION FOR SEQ ID NO: 46:

(i) SEQUENCE CHARACTERISTICS:
        (A) LENGTH: 10
        (B) TYPE: amino acid
        (C) STRANDEDNESS:
        (D) TOPOLOGY: linear (ix) FEATURE:
        (D) OTHER INFORMATION: Xaa represents the D-isomer of
            tyrosine.

(xi) SEQUENCE DESCRIPTION: SEQ ID NO: 46:

Thr Xaa Cys Ala Thr Pro Ala Lys Ser Glu
1               5                   10

(2) INFORMATION FOR SEQ ID NO: 47:

(i) SEQUENCE CHARACTERISTICS:
        (A) LENGTH: 16
        (B) TYPE: amino acid
        (C) STRANDEDNESS:
        (D) TOPOLOGY: linear (ix) FEATURE:
        (D) OTHER INFORMATION: Xaa represents the D-isomer of
            tyrosine.

(xi) SEQUENCE DESCRIPTION: SEQ ID NO: 47:

Cys Ala Leu Leu Glu Thr Xaa Cys Ala Thr Pro Ala Lys Ser Glu Cys
1               5                   10                  15

(2) INFORMATION FOR SEQ ID NO: 48:

(i) SEQUENCE CHARACTERISTICS:
        (A) LENGTH: 12
        (B) TYPE: amino acid
        (C) STRANDEDNESS:
        (D) TOPOLOGY: linear (ix) FEATURE:
        (D) OTHER INFORMATION: Xaa represents the D-isomer of
            tyrosine.

(xi) SEQUENCE DESCRIPTION: SEQ ID NO: 48:

Cys Thr Xaa Cys Ala Thr Pro Ala Lys Ser Glu Cys (2) INFORMATION FOR SEQ ID NO: 49:

(i) SEQUENCE CHARACTERISTICS:
        (A) LENGTH: 11
        (B) TYPE: amino acid
        (C) STRANDEDNESS:
        (D) TOPOLOGY: linear (ix) FEATURE:
        (D) OTHER INFORMATION: Xaa represents the D-isomer of
            tyrosine.

(xi) SEQUENCE DESCRIPTION: SEQ ID NO: 49:

Cys Thr Xaa Cys Ala Pro Ala Lys Ser Glu Cys
1               5                   10

(2) INFORMATION FOR SEQ ID NO: 50:

(i) SEQUENCE CHARACTERISTICS:
        (A) LENGTH: 9
        (B) TYPE: amino acid
        (C) STRANDEDNESS:
        (D) TOPOLOGY: linear (ix) FEATURE:
        (D) OTHER INFORMATION: Xaa represents the D-isomer of
            tyrosine.

(xi) SEQUENCE DESCRIPTION: SEQ ID NO: 50:

Thr Xaa Cys Ala Pro Ala Lys Ser Glu
1               5

(2) INFORMATION FOR SEQ ID NO: 51:

(i) SEQUENCE CHARACTERISTICS:
        (A) LENGTH: 8
        (B) TYPE: amino acid
        (C) STRANDEDNESS:
        (D) TOPOLOGY: linear (xi) SEQUENCE DESCRIPTION: SEQ ID NO: 51:

Thr Tyr Cys Ala Thr Pro Ala Lys
1               5

(2) INFORMATION FOR SEQ ID NO: 52:

(i) SEQUENCE CHARACTERISTICS:
        (A) LENGTH: 8
        (B) TYPE: amino acid
        (C) STRANDEDNESS:
        (D) TOPOLOGY: linear (xi) SEQUENCE DESCRIPTION: SEQ ID NO: 52:

Leu Glu Thr Tyr Cys Ala Thr Pro
1               5

(2) INFORMATION FOR SEQ ID NO: 53:

(i) SEQUENCE CHARACTERISTICS:
        (A) LENGTH: 8
        (B) TYPE: amino acid
        (C) STRANDEDNESS:
        (D) TOPOLOGY: linear (xi) SEQUENCE DESCRIPTION: SEQ ID NO: 53:

Cys Ala Thr Pro Ala Lys Ser Glu
1               5

-continued (2) INFORMATION FOR SEQ ID NO: 54:

(i) SEQUENCE CHARACTERISTICS:
        (A) LENGTH: 8
        (B) TYPE: amino acid
        (C) STRANDEDNESS:
        (D) TOPOLOGY: linear (xi) SEQUENCE DESCRIPTION: SEQ ID NO: 54:

Tyr Cys Ala Pro Ala Lys Ser Glu
1          5

(2) INFORMATION FOR SEQ ID NO: 55:

(i) SEQUENCE CHARACTERISTICS:
        (A) LENGTH: 5
        (B) TYPE: amino acid
        (C) STRANDEDNESS:
        (D) TOPOLOGY: linear (xi) SEQUENCE DESCRIPTION: SEQ ID NO: 55:

Tyr Cys Ala Pro Ala
1          5

(2) INFORMATION FOR SEQ ID NO: 56:

(i) SEQUENCE CHARACTERISTICS:
        (A) LENGTH: 6
        (B) TYPE: amino acid
        (C) STRANDEDNESS:
        (D) TOPOLOGY: linear (xi) SEQUENCE DESCRIPTION: SEQ ID NO: 56:

Thr Tyr Cys Ala Pro Ala
1          5